(12) United States Patent
Chern et al.

(10) Patent No.: US 9,302,992 B2
(45) Date of Patent: Apr. 5, 2016

(54) MULTIFUNCTIONAL QUINOLINE DERIVATIVES AS ANTI-NEURODEGENERATIVE AGENTS

(71) Applicant: ANNJI PHARMACEUTICAL CO., LTD., Taipei (TW)

(72) Inventors: Ji-Wang Chern, Taipei (TW); Chen-Wei Huang, Taipei (TW); Pei-Teh Chang, Taipei (TW); Rahul Subhash Talekar, Taipei (TW)

(73) Assignee: ANNJI PHARMACEUTICAL CO., LTD., Taipei (TW)

( * ) Notice: Subject to any disclaimer, the term of this patent is extended or adjusted under 35 U.S.C. 154(b) by 219 days.

(21) Appl. No.: 13/855,311

(22) Filed: Apr. 2, 2013

(65) Prior Publication Data
US 2014/0296251 A1 Oct. 2, 2014

(51) Int. Cl.
*C07D 215/26* (2006.01)
*C07D 215/28* (2006.01)

(52) U.S. Cl.
CPC ............ *C07D 215/26* (2013.01); *C07D 215/28* (2013.01)

(58) Field of Classification Search
CPC .............................. C07D 215/26; C07D 215/28
See application file for complete search history.

(56) References Cited

U.S. PATENT DOCUMENTS

| 3,682,927 | A * | 8/1972 | Carissimi et al. ............. 546/159 |
| 6,127,360 | A | 10/2000 | Timmerman et al. |
| 7,009,053 | B2 | 3/2006 | Kim et al. |
| 7,034,182 | B2 * | 4/2006 | Fang et al. .................... 564/147 |
| 7,439,243 | B2 | 10/2008 | Johnson et al. |

(Continued)

FOREIGN PATENT DOCUMENTS

| CN | 102526052 A | 7/2012 |
| WO | 94/10164 A1 | 5/1994 |

(Continued)

OTHER PUBLICATIONS

Cannon, "Synthesis of certain tricyclic quinoline derivatives as potential antiamebal agents", Journal of Heterocyclic Chemistry (1967), 4(2), 259-61.*
Sachin, "An efficient synthesis of ([18F]fluoropropyl)quinoline-5,8-diones by rapid radiofluorinationeoxidative demethylation", Tetrahedron, 67 (2011), pp. 1763-1767.*
PCT International Search Report for PCT/US2013/034960.
Talekar et al. Nonreductive deiodination of ortho-Iodo-Hydroxiated arenes using tertiary amines. J. Org. Chem. 2005, 70, 8590-8593.

Chia E. W. et al., "Synthesis and anti-inflammatory structure-activity relationships of thiazine-quinoline-quinones: Inhibitors of the neutrophil respiratory burst in a model of acute gouty arthritis", Bioorganic & Medicinal Chemistry, 2008, vol. 16, pp. 9432-9442.

*Primary Examiner* — Sreeni Padmanabhan
*Assistant Examiner* — Sahar Javanmard
(74) *Attorney, Agent, or Firm* — Hsiu-Ming Saunders; Intellectual Property Connections, Inc.

(57) ABSTRACT

Novel quinoline derivatives are disclosed. Also disclosed are synthesis and use thereof for treating neurodegenerative diseases. In one aspect, the invention relates to a compound of Formula (I) or a pharmaceutically acceptable salt thereof:

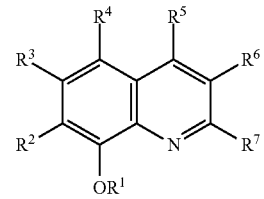

Formula (I)

(I) wherein
$R^1$ is hydrogen, $(C_1-C_8)$alkyl, $(C_1-C_8)$alkylene$(C_3-C_8)$cycloalkyl, $(C_1-C_8)$haloalkyl, or $(C_1-C_8)$alkylene$(C_6-C_{20})$aryl;
$R^2$ is hydrogen or halogen;
$R^3$ is hydrogen, halogen, $(C_1-C_8)$alkyl, or $(C_1-C_8)$alkoxy;
$R^4$ is hydrogen, halogen, $(C_1-C_8)$alkyl, $(C_1-C_8)$alkoxy, or $(C_1-C_8)$haloalkyl;
$R^5$ is hydrogen or $(C_1-C_{20})$alkanol;
$R^6$ is hydrogen; and
$R^7$ is $(C_1-C_{20})$alkanol, $(C_1-C_8)$alkylene $(C_3-C_8)$heterocyclyl$(C_1-C_{20})$alkanol, $(C_1-C_8)$alkylene $(C_3-C_8)$heterocyclyl$(C_1-C_{20})$alkyl, $(C_1-C_8)$alkylene$(C_1-C_6)$alkylamino $(C_1-C_6)$alkynyl, $(C_1-C_8)$alkyleneamino$(C_1-C_{20})$alkanol, or $(C_1-C_8)$alkyleneamino$(C_1-C_{20})$alkanol$(C_1-C_8)$alkylene substituted $(C_3-C_{20})$heteroaryl;
(II) or wherein:
$R^1$, $R^2$, $R^3$, $R^4$ and $R^6$ are each defined in (I) above;
$R^5$ is $(C_1-C_{20})$alkanol; and
$R^7$ is hydrogen, $(C_1-C_{20})$alkanol, $(C_1-C_8)$alkylene $(C_3-C_8)$heterocyclyl$(C_1-C_{20})$alkanol, $(C_1-C_8)$alkylene $(C_3-C_8)$heterocyclyl$(C_1-C_{20})$alkyl, $(C_1-C_8)$alkylene$(C_1-C_6)$alkylamino$(C_1-C_6)$alkynyl, $(C_1-C_8)$alkyleneamino$(C_1-C_{20})$alkanol, or $(C_1-C_8)$alkyleneamino$(C_1-C_{20})$alkanol $(C_1-C_8)$alkylene substituted $(C_3-C_{20})$heteroaryl.

19 Claims, 2 Drawing Sheets

(56) References Cited

U.S. PATENT DOCUMENTS 7,452,888 B2 11/2008 Ahmed et al.
2005/0165052 A1 7/2005 Fakhfakh et al.
2006/0089380 A1 4/2006 Barnham et al.

FOREIGN PATENT DOCUMENTS

| WO | 2004/007461 A1 | 1/2004 |
| WO | 2004/076386 A2 | 9/2004 |
| WO | 2011/150156 A2 | 12/2011 |

* cited by examiner

MULTIFUNCTIONAL QUINOLINE DERIVATIVES AS ANTI-NEURODEGENERATIVE AGENTS

BACKGROUND OF THE INVENTION

U.S. Pat. Nos. 7,439,243 and 7,452,888 describe a series of quinoline derivatives useful for the treatment of CNS disorders, including Alzheimer's disease. U.S. Pat. No. 7,009,053 describe a series of quinoline derivatives useful for treatment of Alzheimer's disease, Huntington's disease, Parkinson's disease, amyotrophic lateral sclerosis, stroke, ischemia, traumatic brain injury, spinal cord injury or osteoarthritis.

SUMMARY OF THE INVENTION

In one aspect, the invention relates to a compound of Formula (I) or a pharmaceutically acceptable salt, a solvate or hydrate, a prodrug, or a metabolite thereof:

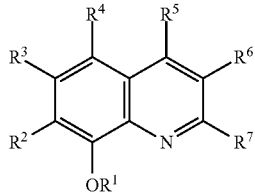

Formula (I)

wherein
$R^1$ is hydrogen, $(C_1-C_8)$alkyl, $(C_1-C_8)$alkylene$(C_3-C_8)$cycloalkyl, $(C_1-C_8)$haloalkyl, or $(C_1-C_8)$alkylene$(C_6-C_{20})$aryl;
$R^2$ is a hydrogen or halogen;
$R^3$ is hydrogen, halogen, $(C_1-C_8)$alkyl, or $(C_1-C_8)$alkoxy;
$R^4$ is hydrogen, halogen, $(C_1-C_8)$alkyl, $(C_1-C_8)$alkoxy, or $(C_1-C_8)$haloalkyl;
$R^5$ is hydrogen or $(C_1-C_{20})$alkanol;
$R^6$ is hydrogen; and
$R^7$ is hydrogen, $(C_1-C_{20})$alkanol, $(C_1-C_8)$alkylene $(C_3-C_8)$heterocyclyl$(C_1-C_{20})$alkanol, $(C_1-C_8)$alkylene $(C_3-C_8)$heterocyclyl$(C_1-C_{20})$alkyl, $(C_1-C_8)$alkylene$(C_1-C_6)$alkylamino$(C_1-C_6)$alkynyl, $(C_1-C_8)$alkyleneamino$(C_1-C_{20})$alkanol, or $(C_1-C_8)$alkyleneamino$(C_1-C_{20})$alkanol$(C_1-C_8)$alkylene substituted $(C_3-C_{20})$heteroaryl.

In another aspect, the invention relates to a method for preparing the compound as aforementioned, the method comprising:
(1) reacting the compound of Formula (II)

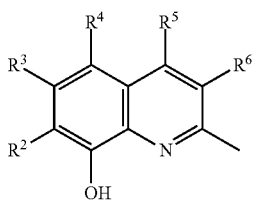

Formula (II)

wherein:
$R^2, R^3, R^4, R^5$, and $R^6$ are each independently hydrogen; or
$R^2, R^4, R^5$, and $R^6$ are each independently hydrogen and $R^3$ is $CH_3$; or
$R^2, R^3, R^5$, and $R^6$ are each independently hydrogen and $R^4$ is $CH_3$, F, Cl, or Br; or
$R^2, R^5, R^6$ are each independently hydrogen, $R^3$ is $OCH_3$, and $R^4$ is Cl; or
$R^2, R^4$ is Cl and $R^3, R^5, R^6$ are each independently hydrogen,
with benzyl bromide, methyl iodide, ethyl iodide, 2-bromopropane, or methylenecyclopropyl bromide in a basic solution at about room temperature to about 80° C. to obtain the compound of Formula (III)

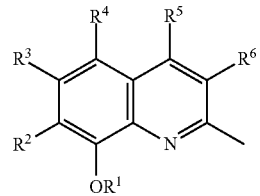

Formula (III)

wherein:
$R^1$ is $CH_3$, $CH_2CH_3$, $CH(CH_3)_2$, $CH_2CH(CH_3)_2$, or benzyl; and
$R^2, R^3, R^4, R^5$, and $R^6$ are each independently hydrogen; or
$R^2, R^4, R^5$, and $R^6$ are each independently hydrogen and $R^3$ is $CH_3$; or
$R^2, R^3, R^5$, and $R^6$ are each independently hydrogen and $R^4$ is $CH_3$, F, Cl, or Br; or
$R^2, R^5, R^6$ are each independently hydrogen, $R^3$ is $OCH_3$, and $R^4$ is Cl; or
$R^2, R^4$ is Cl and $R^3, R^5, R^6$ are each independently hydrogen;
(2) reacting the compound of Formula (III) with lithium bis(trimethylsilyl)amide and a bromo$(C_1-C_{20})$alkanol in tetrahydrofuran at 0° C. to obtain the compound of Formula (I)

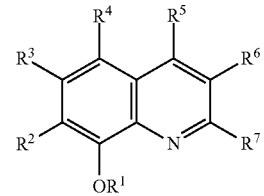

Formula (I)

wherein:
$R^1$ is $CH_3$, $CH_2CH_3$, $CH(CH_3)_2$, $CH_2CH(CH_3)_2$, or benzyl;
$R^2, R^3, R^4, R^5$, and $R^6$ are each independently hydrogen; or
$R^2, R^4, R^5$, and $R^6$ are each independently hydrogen and $R^3$ is $CH_3$; or
$R^2, R^3, R^5$, and $R^6$ are each independently hydrogen and $R^4$ is $CH_3$, F, Cl, or Br; or
$R^2, R^5, R^6$ are each independently hydrogen, $R^3$ is $OCH_3$, and $R^4$ is Cl; or $R^3$ is Cl, and $R^4$ is $OCH_3$ or
$R^2, R^4$ is Cl and $R^3, R^5, R^6$ are each independently hydrogen; and
$R^7$ is $(CH_2)_9OH$, $(CH_2)_{10}OH$, $(CH_2)_{11}OH$, $(CH_2)_{12}OH$, $(CH_2)_{13}OH$, or $(CH_2)_{15}OH$,
(3) reacting the compound of Formula (I), wherein $R^1$ is benzyl, with hydrogen gas under pressure with palladium on carbon at room temperature in methanol or with boron trichloride in dichloromethane at 0° C. to obtain the compound of Formula (I)

Formula (I)

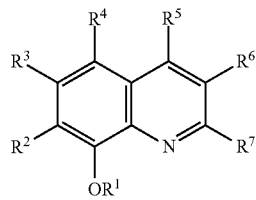

$R^1$, $R^2$, $R^3$, $R^4$, $R^5$, and $R^6$ are each independently hydrogen; or $R^1$, $R^2$, $R^4$, $R^5$, and $R^6$ are each independently hydrogen and $R^3$ is $CH_3$; or $R^1$, $R^2$, $R^3$, $R^5$, and $R^6$ are each independently hydrogen and $R^4$ is $CH_3$, F, Cl, or Br; or $R^1$, $R^2$, $R^5$, $R^6$ are each independently hydrogen, $R^3$ is $OCH_3$, and $R^4$ is Cl; or $R^2$, $R^4$ is Cl and $R^1$, $R^3$, $R^5$, $R^6$ are each independently hydrogen; and $R^7$ is $(CH_2)_9OH$, $(CH_2)_{10}OH$, $(CH_2)_{11}OH$, $(CH_2)_{12}OH$, $(CH_2)_{13}OH$, or $(CH_2)_{15}OH$; or (4) reacting the compound of Formula (I), wherein $R^1$, $R^2$, $R^3$, $R^4$, $R^5$, and $R^6$ are each independently hydrogen and $R^7$ is $(CH_2)_{11}OH$, with N-chlorosuccinimide in methylene chloride at room temperature to afford the compound of Formula (I), wherein $R^1$, $R^3$, $R^5$, and $R^6$ are each independently hydrogen, $R^2$ and $R^4$ are each independently chlorine, and $R^7$ $(CH_2)_{11}OH$; or (5) reacting the compound of Formula (I), wherein $R^1$ is methyl, $R^2$, $R^3$, $R^4$, $R^5$, and $R^6$ are each independently hydrogen and $R^7$ is $(CH_2)_{11}OH$, $(CH_2)_{12}OH$ or $(CH_2)_{13}OH$ with concentrated hydrochloric acid, $ICl_3$, and glacial acetic acid to afford the compound of Formula (I), wherein $R^1$ is methyl $R^2$, $R^3$, $R^5$, and $R^6$ are each independently hydrogen, $R^4$ is Cl, and $R^7$ is $(CH_2)_{10}OH$, $(CH_2)_{11}OH$, $(CH_2)_{12}OH$, $(CH_2)_{13}OH$, $(CH_2)_{15}OH$, $(CH_2)_{10}OCOCH_3$, $(CH_2)_{11}OCOCH_3$, $(CH_2)_{12}OCOCH_3$, or $(CH_2)_{13}OCOCH_3$; or (6) reacting 2-aminophenol with methylvinyl ketone in hydrochloric acid to obtain the compound of Formula (INT-1), Formula (INT-1)

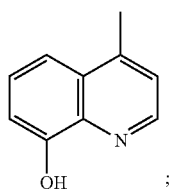

(7) reacting the compound of Formula (INT-1) with methyl iodide, ethyl iodide, 2-bromopropane, methylenecyclopropyl bromide, or benzyl bromide in basic solution to afford the compound of Formula (III), Formula (III)

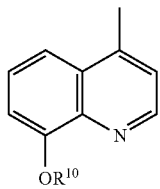

wherein $R^{10}$ is methyl, ethyl, 2-propyl, methylenecyclopropyl, or benzyl;

(8) reacting the compound of Formula (III), wherein $R^{10}$ is methyl, ethyl, 2-propyl, methylenecyclopropyl, or benzyl, with lithium bis(trimethylsilyl)amide and 10-bromo-1-decanol or 11-bromo-1-undecanol in tetrahydrofuran at 0° C. to obtain the compound of Formula (I), wherein $R^1$ is methyl, ethyl, 2-propyl, methylenecyclopropyl or benzyl; $R^2$, $R^3$, $R^4$, $R^6$, and $R^7$ are each independently hydrogen; and $R^5$ is $(CH_2)_{11}OH$ or $(CH_2)_{12}OH$;

(9) reacting the compound of Formula (I), wherein $R^1$ is benzyl; $R^2$, $R^3$, $R^4$, $R^6$, and $R^7$ are each independently hydrogen; and $R^5$ is $(CH_2)_{11}OH$ or $(CH_2)_{12}OH$, with hydrogen gas under pressure with palladium on carbon at room temperature in methanol to obtain the compound of Formula (I), wherein $R^1$ is hydrogen; $R^2$, $R^3$, $R^4$, $R^6$, and $R^7$ are each independently hydrogen; and $R^5$ is $(CH_2)_{11}OH$ or $(CH_2)_{12}OH$; or

(10) reacting 2-trifluoromethoxyaniline with crotonaldehyde to obtain 2-methyl-8-trifluoromethoxyquinoline, which is treated with lithium bis(trimethylsilyl)amide and a bromo $(C_1-C_{20})$alkanol in tetrahydrofuran at 0° C. to obtain the compound of Formula (I), wherein $R^1$ is trifluoromethyl; $R^2$, $R^3$, $R^4$, $R^5$, and $R^6$ are each independently hydrogen; and $R^7$ is $(CH_2)_{10}OH$, $(CH_2)_{11}OH$, $(CH_2)_{12}OH$, $(CH_2)_{13}OH$, or $(CH_2)_{15}OH$; or

(11) reacting an 8-hydroxy-2-methylquinoline compound of Formula (IV), wherein $R^1$ is hydrogen, methyl, ethyl 2-propyl, or methylenecyclopropyl, Formula (V)

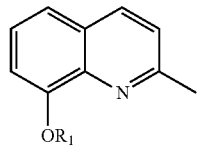

with selenium dioxide in dioxide at elevated temperature to afford a compound of Formula (VI), $R^1$ is hydrogen, methyl, ethyl, 2-propyl, or methylenecyclopropyl; and Formula (VI)

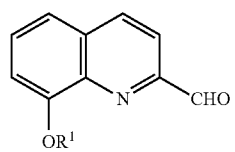

(12) reacting the compound of Formula (VI), wherein $R^1$ is hydrogen, methyl, ethyl, 2-propyl, or methylenecyclopropyl, with N-methylpropagylamine to obtain a compound of Formula (I), wherein $R^1$ is hydrogen, $CH_3$, $CH_2CH_3$, $CH_2CH(CH_3)_2$, $CH_2CH(CH_2)_2$, or $CH(CH_3)_2$, $R^2$, $R^3$, $R^4$, $R^5$, and $R^6$ are each independently hydrogen; and $R^7$ is $CH_2N(CH_3)CH_2C\equiv CH$; or

(13) reacting the compound of Formula (VI), $R^1$ is hydrogen, methyl, ethyl, 2-propyl, or methylenecyclopropyl, with 2(piperazin-1-yl)ethanol to obtain a compound of Formula (I), wherein $R^1$ is hydrogen, $CH_3$, $CH_2CH_3$, $CH_2CH(CH_3)_2$, $CH_2CH(CH_2)_2$, or $CH(CH_3)_2$, $R^2$, $R^3$, $R^4$, $R^5$, and $R^6$ are each independently hydrogen; and $R^7$ is $CH_2(N(CH_2CH_2)_2N)CH_2CH_2OH$; or reacting compound of Formula (VI) with an amino($C_1$-$C_{20}$)alkanol to obtain a compound of Formula (I), wherein $R^1$ is hydrogen, $CH_3$, $CH_2CH_3$, $CH_2CH(CH_3)_2$, $CH_2CH(CH_2)_2$, or $CH(CH_3)_2$; $R^2$, $R^3$, $R^4$, $R^5$, and $R^6$ are each independently hydrogen; and $R^7$ is $CH_2NH(CH_2)_8OH$, or $CH_2N((CH_2)_6OH)CH_2$(8-methoxyquinolin-2-yl).

In another aspect, the invention relates to a composition comprising a therapeutically effective amount of the compound as aforementioned, or a pharmaceutically acceptable salt, a solvate or hydrate, a prodrug, or a metabolite thereof, and a pharmaceutically acceptable diluent or carrier.

In another aspect, the invention relates to a method of treating a neurodegenerative disease, comprising administering to a subject in need thereof a therapeutically effective amount of a compound as aforementioned, or a pharmaceutically acceptable salt, a solvate or hydrate, a prodrug, or a metabolite thereof, and a pharmaceutically acceptable vehicle or carrier.

Further in another aspect, the invention relates to a composition comprising a compound as aforementioned, or a pharmaceutically acceptable salt, a solvate or hydrate, a prodrug, or a metabolite thereof, and a pharmaceutically acceptable diluent or carrier for use in treating a neurodegenerative disease.

Yet in another aspect, the invention relates to a use of a compound as aforementioned in the manufacture of a medicament for treating a neurodegenerative disease. In one embodiment, the medicament is for treating Alzheimer's disease.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Figure 1A:
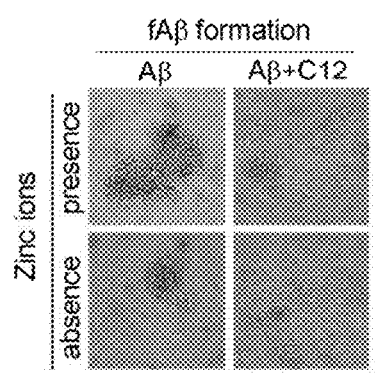
FIGS. 1A-B show morphological analysis of the effects of compound C12 on fAβ formation and dissociation of fAβs in the presence or absence of zinc ions.

The singular forms "a," "an," and "the" include plural reference unless the context clearly dictates otherwise.

A dash ("-") that is not between two letters or symbols is used to indicate a point of attachment for a moiety or substituent. For example, the moiety —$CONH_2$ is attached through the carbon atom.

The term "amino" refers to —$NH_2$. The amino group can be optionally substituted as defined herein for the term "substituted." The term "alkylamino" refers to —$NR_2$, wherein at least one R is alkyl and the second R is alkyl or hydrogen. The term "acylamino" refers to $N(R)C(=O)R$, wherein each R is independently hydrogen, alkyl, or aryl.

The term "alkyl" refers to a $C_1$-$C_{18}$ hydrocarbon containing normal, secondary, tertiary or cyclic carbon atoms. Examples are methyl, ethyl, 1-propyl, 2-propyl, 1-butyl, 2-methyl-1-propyl (iso-butyl, —$CH_2CH(CH_3)_2$), 2-butyl (sec-butyl, —$CH(CH_3)CH_2CH_3$), 2-methyl-2-propyl (tert-butyl, —$C(CH_3)_3$), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl. The alkyl can be a monovalent hydrocarbon radical, as described and exemplified above, or it can be a divalent hydrocarbon radical (i.e., alkylene). The alkyl can optionally be substituted with one or more alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyanato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl or hydroxy. The alkyl can optionally be interrupted with one or more non-peroxide oxy (—O—), thio (—S—), amino (—N(H)—), methylene dioxy (—$OCH_2O$—), carbonyl (—C(=O)—), carboxy (—C(=O)—), carbonyldioxy (—OC(=O)O—), carboxylato (—OC(=O)—), imino (C=NH), sulfinyl (SO) or sulfonyl ($SO_2$). Additionally, the alkyl can optionally be at least partially unsaturated, thereby providing an alkenyl.

The term, "alkylene" refers to a saturated, branched or straight chain or cyclic hydrocarbon radical of 1-18 carbon atoms, and having two monovalent radical centers derived by the removal of two hydrogen atoms from the same or different carbon atoms of a parent alkane. Typical alkylene radicals include, but are not limited to: methylene (—$CH_2$—) 1,2-ethylene (—$CH_2CH_2$—), 1,3-propylene (—$CH_2CH_2CH_2$—), 1,4-butylene (—$CH_2CH_2CH_2CH_2$—), and the like. The alkylene can optionally be substituted with one or more alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl or hydroxy. Additionally, the alkylene can optionally be interrupted with one or more non-peroxide oxy (—O—), thio (—S—), amino (—N(H)—), methylene dioxy (—OCH$_2$O—), carbonyl (—C(=O)—), carboxy (—C(=O)O—) carbonyldioxy (—OC(=O)O—), carboxylato (—OC(=O)—), imine (C=NH), sulfinyl (SO) or sulfonyl (SO$_2$). Moreover, the alkylene can optionally be at least partially unsaturated, thereby providing an alkenylene.

The term "alkynyl" refers to a monoradical branched or unbranched hydrocarbon chain, having a point of complete unsaturated (i.e., a carbon-carbon, sp triple bond). In one embodiment, the alkynyl group can have from 2 to 10 carbon atoms, or 2 to 6 carbon atoms. In another embodiment, the alkynyl group can have from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, 1-octynyl and the like. The alkynyl can be unsubstituted or substituted.

The term "alkoxy" refers to the group alkyl-O—, where alkyl is defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can optionally be substituted with one or more halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy.

The term "alkanol" refers to a compound of a general formula ROH, where R is alkyl, as defined herein.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like. The aryl can optionally be a divalent radical, thereby providing an arylene. The aryl can optionally be substituted with one or more alkyl alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

The term "carbocycle" refers to a saturated, unsaturated or aromatic ring having 3 to 8 carbon atoms as a monocyclic, 7 to 12 carbon atoms as a bicycle, and up to about 30 carbon atoms as a poly cycle. Monocyclic carbocycles typically have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. The carbocycle can be optionally substituted as described above for alkyl groups.

When a substituent is specified to be an atom or atoms of specified identity, "or a bond", a configuration is referred to when the substituent is "a bond" that the groups that are immediately adjacent to the specified substituent are directly connected to each other by a chemically feasible bonding configuration.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. The cycloalkyl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy. The cycloalkyl can optionally be at least partially unsaturated, thereby providing a cycloalkenyl. Additionally, the cycloalkyl can optionally be a divalent radical, thereby providing a cycloalkylene.

The term "an effective amount" refers to an amount sufficient to effect beneficial or desired results. Determination of an effective amount for a given administration is well within the ordinary skill in the pharmaceutical arts.

The term "halo" refers to fluoro, chloro, bromo, and iodo. Similarly, the term "halogen" refers to fluorine, chlorine, bromine, and iodine.

The term "haloalkyl" refers to alkyl substituted by 1-4 halo groups, which may be the same or different. Representative haloalkyl groups include trifluoromethyl, 3-fluorododecyl, 12,12,12-trifluorododecyl, 2-bromooctyl, 3-bromo-6-chloroheptyl, and the like.

The term "heteroaryl" is a monocyclic, bicyclic, or tricyclic ring system containing one, two, or three aromatic rings and containing at least one nitrogen, oxygen, or sulfur atom in an aromatic ring, and which can be unsubstituted or substituted. The heteroaryl can optionally be a divalent radical, thereby providing a heteroarylene. Examples of heteroaryl groups include, but are not limited to, 2H-pyrrolyl, 3H-indolyl, 4H-quinolizinyl, 4H-carbazolyl, acridinyl, benzo[b]thienyl, benzothiazolyl, β-carbolinyl, carbazolyl, chromenyl, cinnaolinyl, dibenzo[b,d]furanyl, furazanyl, furyl, imidazolyl, imidizolyl, indazolyl, indolisinyl, indolyl, isobenzofuranyl, isoindoyl, isoquinolyl, isothiazolyl, isoxazolyl, naphthyridinyl, naptho[2,3-b], oxazolyl, perimidinyl, phenathridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group non-peroxide oxygen, sulfur, and N(Z) wherein Z is absent or is H, O, alkyl, phenyl, or benzyl. In another embodiment heteroaryl denotes an ortho-fused bicyclic heterocycle of about eight to ten ring atoms derived therefrom, particularly a benz-derivative or one derived by fusing a propylene, or tetramethylene diradical thereto.

The heteroaryl can optionally be substituted with one or more alkyl alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy.

The term "heterocycle" or "heterocyclyl" refers to a saturated or partially unsaturated ring system, containing at least one heteroatom selected from the group oxygen, nitrogen, and sulfur, and optionally substituted with alkyl, or C(=O)$OR^b$, wherein $R^b$ is hydrogen or alkyl. Typically heterocycle is a monocyclic, bicyclic, or tricyclic group containing one or more heteroatoms selected from the group oxygen, nitrogen, and sulfur. A heterocycle group also can contain an oxo group (=O) attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine. The heterocycle can optionally be a divalent radical, thereby providing a heterocyclene. The heterocycle can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "hydrate" refers to the complex where the solvent molecule is water.

The terms "individual," "host," "subject," and "patient" are used interchangeably, and refer to a mammal, including, but not limited to, primates, including simians and humans.

The term "metabolite" refers to any compound of the Formula (I) produced in vivo or in vitro from the parent drug, or its prodrugs.

The pharmaceutically acceptable salts of the compounds described herein can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two: generally, nonaqueous media like ether, ethyl acetate, ethanol, isopropanol, or acetonitrile are preferred. Lists of many suitable salts are found in *Remington: The Science and Practice of Pharmacy*, $21^{st}$ edition, Lippincott Williams & Wilkins, (2005).

Pharmaceutically acceptable prodrugs refer to a compound that is metabolized, for example hydrolyzed or oxidized, in the host to form a compound of the Formula (I). Typical examples of prodrugs include compounds that have biologically labile protecting groups on a functional moiety of the active compound. Prodrugs include compounds that can be oxidized, reduced, animated, deaminated, hydroxylated, dehydroxylated, hydrolyzed, dehydrolyzed, alkylated, dealkylated, acylated, deacylated, phosphorylated, dephosphorylated to produce the active compound.

The prodrug can be readily prepared from the compounds of Formula (I) using methods known in the art. See, e.g. See Notari, R. E., "Theory and Practice of Prodrug Kinetics," *Methods in Enzymology*, 112:309 323 (1985); Bodor, N., "Novel Approaches in Prodrug Design," *Drugs of the Future*, 6(3): 165 182 (1981); and Bundgaard, H., "Design of Prodrugs: Bioreversible-Derivatives for Various Functional Groups and Chemical Entities," in Design of Prodrugs (H. Bundgaard, ed.), Elsevier, N.Y. (1985); Burger's Medicinal Chemistry and Drug Chemistry, Fifth Ed., Vol. 1, pp. 172 178, 949 982(1995).

The term "solvate" refers to a complex of variable stoichiometry formed by a solute (in this invention, a compound of Formula I, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid.

The phrase "room temperature" refers to a temperature in the range of about 20° C. to about 30° C.

The term "substituted" is intended to indicate that one or more hydrogens on the atom indicated is replaced with a selection from the indicated group(s), provided that the indicated atom's normal valency is not exceeded, and that the substitution results in a stable compound. Suitable indicated groups include, e.g., alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, acyloxy, alkoxycarbonyl, amino, imino, alkylamino, acylamino, nitro, trifluoromethyl, trifluoromethoxy, carboxy, carboxyalkyl, keto, thioxo, alkylthio, alkylsulfonyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyanato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy. When a substituent is oxo (i.e., =O) or thioxo (i.e., =S) group, then two hydrogens on the atom are replaced.

The terms "treating" or "treat" or "treatment" refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease.

The invention relates to multi functional quinoline derivatives having following properties: metal chelation, clearance of reactive oxygen species, anti-aggregation, neurite outgrowth and neuron proliferation, They are useful for treating neurondegenerative disease involving neuronal toxicity or dysfunction induced by oxidative stress and other disorders associated with misfolding protein aggregation, in animal model, quinoline derivatives (B3 or C12) at 1 to 100 mg/kg, preferable 1 to 10 mg/kg, i.p. daily) were found to improve memory of mice without causing significant toxicity.

In one aspect, the invention relates to a compound of Formula (I) or a pharmaceutically acceptable salt, a solvate or hydrate, a prodrug, or a metabolite thereof:

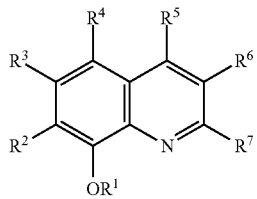

Formula (I)

wherein
$R^1$ is hydrogen, $(C_1-C_8)$alkyl, $(C_1-C_8)$alkylene$(C_3-C_8)$cycloalkyl, $(C_1-C_8)$haloalkyl, or $(C_1-C_8)$alkylene$(C_6-C_{20})$aryl;
$R^2$ is hydrogen or halogen;
$R^3$ is hydrogen, halogen, $(C_1-C_8)$alkyl, or $(C_1-C_8)$alkoxy;
$R^4$ is hydrogen, halogen, $(C_1-C_8)$alkyl, $(C_1-C_8)$alkoxy, or $(C_1-C_8)$haloalkyl;
$R^5$ is hydrogen $(C_1-C_{20})$alkanol;
$R^6$ is hydrogen; and
$R^7$ is hydrogen, $(C_1-C_{20})$alkanol, $(C_1-C_8)$alkylene $(C_3-C_8)$heterocyclyl$(C_1-C_{20})$alkanol, $(C_1-C_8)$alkylene $(C_3-C_8)$heterocyclyl$(C_1-C_{20})$alkyl, $(C_1-C_8)$alkylene$(C_1-C_6)$alkylamino $(C_1-C_6)$alkynyl, $(C_1-C_8)$alkyleneamino$(C_1-C_{20})$alkanol, or $(C_1-C_8)$alkyleneamino$(C_1-C_{20})$alkanol$(C_1-C_8)$alkylene substituted $(C_3-C_{20})$heteroaryl.

In one embodiment of the invention, wherein
$R^1$ is hydrogen, $CH_3$, $CH_2CH_3$, $CH(CH_3)_2$, $CH_2CH(CH_3)_2$, $CF_3$, or benzyl;
$R^2$ is hydrogen, F, or Cl;
$R^3$ is hydrogen, F, Cl, $CH_3$, or $OCH_3$;
$R^4$ is hydrogen, F, Cl, Br, $CH_3$, $OCH_3$, or $CF_3$;
$R^5$ is hydrogen, $(CH_2)_{11}OH$, or $(CH_2)_{12}OH$;
$R^6$ is hydrogen; and
$R^7$ is hydrogen, $(CH_2)_9OH$, $(CH_2)_{10}OH$, $(CH_2)_{11}OH$, $(CH_2)_{12}OH$, $(CH_2)_{13}OH$, $(CH_2)_{14}OH$, $(CH_2)_{15}OH$, $CH_2(N(CH_2CH_2)_2N)CH_2CH_2OH$, $CH_2(N(CH_2CH_2)_2N)CH_2CH_3$, $CH_2N(CH_3)CH_2C\equiv CH$, $CH_2NH(CH_2)_8OH$, or $CH_2N((CH_2)_6OH)CH_2$(8-methoxyquinolin-2-yl).

In another embodiment of the invention, wherein
$R^1$ is hydrogen, $CH_3$, $CH_2CH_3$, $CH(CH_3)_2$, $CH_2CH(CH_3)_2$, $CH_2CH(CH_2)_2$, $CF_3$, or benzyl;
$R^2$, $R^3$, $R^4$, $R^5$, and $R^6$ are each independently hydrogen; and
$R^7$ is $(CH_2)_9OH$, $(CH_2)_{10}OH$, $(CH_2)_{11}OH$, $(CH_2)_{12}OH$, $(CH_2)_{13}OH$, $(CH_2)_{14}OH$, $(CH_2)_{15}OH$, $CH_2(N(CH_2CH_2)_2N)CH_2CH_2OH$, or $CH_2N(CH_3)CH_2C\equiv CH$.

In another embodiment of the invention, wherein
$R^1$ is hydrogen, $CH_3$, $CH_2CH_3$, $CH_2CH(CH_3)_2$, $CH_2CH(CH_2)_2$, or $CH(CH_3)_2$;
$R^2$, $R^3$, $R^5$, and $R^6$ are each independently hydrogen;
$R^4$ is $CH_3$, F, Cl, Br, $CF_3$, or $OCH_3$; and
$R^7$ is $(CH_2)_9OH$, $(CH_2)_{10}OH$, $(CH_2)_{11}OH$, $(CH_2)_{12}OH$, $(CH_2)_{13}OH$, $(CH_2)_{15}OH$, $(CH_2)_{10}OCOCH_3$, $(CH_2)_{11}OCOCH_3$, $(CH_2)_{12}OCOCH_3$, $(CH_2)_{13}OCOCH_3$, $CH_2NH(CH_2)_8OH$, $CH_2(N(CH_2CH_2)_2N)CH_2CH_2OH$, $CH_2(N(CH_2CH_2)_2N)CH_2CH_3$, or $CH_2N(CH_3)CH_2C\equiv CH$.

In another embodiment of the invention, wherein
$R^1$ is hydrogen, $CH_3$, $CH_2CH_3$, $CH(CH_2)_2$, or $CH_2CH(CH_2)_2$;
$R^2$, $R^4$ are each independently Cl;
$R^3$, $R^5$, and $R^6$ are each independently hydrogen; and
$R^7$ is $(CH_2)_{11}OH$, $CH_2NH(CH_2)_8OH$, or $CH_2N(CH_3)CH_2C\equiv CH$.

In another embodiment of the invention, wherein
$R^1$ is hydrogen, $CH_3$, $CH_2CH_3$, $CH_2CH(CH_3)_2$, $CH_2CH(CH_2)_2$, $CH(CH_3)_2$, or benzyl;
$R^2$, $R^3$, $R^4$, $R^6$, and $R^7$ are each independently hydrogen; and
$R^5$ is $(CH_2)_{11}OH$ or $(CH_2)_{12}OH$.

In another embodiment of the invention wherein
$R^1$ is $CH_3$;
$R^2$, $R^5$, and $R^6$ are each independently hydrogen;
$R^3$ and $R^4$ are each independently $OCH_3$ or Cl; and
$R^7$ is $(CH_2)_{11}OH$.

In another embodiment of the invention, the compound is selected from the group consisting of 9-(8-(benzyloxy)quinolin-2-yl)nonan-1-ol, 10-(8-(benzyloxy)quinolin-2-yl)decan-1-ol, 11-(8-(benzyloxy)quinolin-2-yl)undecan-1-ol, 12-(8-(benzyloxy)quinolin-2-yl)dodecan-1-ol, 13-(8-(benzyloxy)quinolin-2-yl)tridecan-1-ol, 14-((8-(benzyloxy)quinolin-2-yl)tetradecan-1-ol, 15-(8-(benzyloxy)quinolin-2-yl) pentadecan-1-ol, 11-(8-(benzyloxy)-5-methylquinolin-2-yl) undecan-1-ol, 11-(8-(benzyloxy)-6-methylquinolin-2-yl) undecan-1-ol, 11-(8-(benzyloxy)-5-fluoroquinolin-2-yl) undecan-1-ol, 11-(8-(benzyloxy)-5-chloroquinolin-2-yl) undecan-1-ol, 2-(9-hydroxynonyl)quinolin-8-ol, 2-(10-hydroxydecyl)quinolin-8-ol, 2-(11-hydroxyundecyl) quinolin-8-ol, 2-(12-hydroxydodecyl)quinolin-8-ol, 2-(13-hydroxytridecyl)quinolin-8-ol, 2-(14-(hydroxytetradecyl)

quinolin-8-ol, 2-(15-hydroxypentadecyl)quinolin-8-ol, 2-(11-hydroxyundecyl)-5-methylquinolin-8-ol, 2-(11-hydroxyundecyl)-6-methylquinolin-8-ol, 5-chloro-2-(11-hydroxyundecyl)quinolin-8-ol, 9-(8-methoxyquinolin-2-yl)nonan-1-ol, 10-(8-methoxyquinolin-2-yl)decan-1-ol, 11-(8-methoxyquinolin-2-yl)undecan-1-ol, 12-(8-methoxyquinolin-2-yl)dodecan-1-ol, 13-(8-methoxyquinolin-2-yl)tridecan-1-ol, 14-((8-methoxyquinolin-2-yl)tetradecan-1-ol, 15-(8-methoxyquinolin-2-yl)pentadecan-1-ol, 11-(8-methoxy-5-methylquinolin-2-yl)undecan-1-ol, 11-(5-fluoro-8-methoxyquinolin-2-yl)undecan-1-ol, 12-(5-fluoro-8-methoxyquinolin-2-yl)dodecan-1-ol, 9-(5-chloro-8-methoxyquinolin-2-yl)nonan-1-ol, 11-(5-chloro-8-methoxyquinolin-2-yl)undecan-1-ol, 15-(5-chloro-8-methoxyquinolin-2-yl)pentadecan-1-ol, 11-(5-bromo-8-methoxyquinolin-2-yl)undecan-1-ol, 11-(8-methoxy-5-(trifluoromethyl)quinolin-2-yl)undecan-1-ol, 11-(5,8-dimethoxyquinolin-2-yl)undecan-1-ol, 11-(8-methoxy-6-methylquinolin-2-yl)undecan-1-ol, 11-(6-fluoro-8-methoxyquinolin-2-yl)undecan-1-ol, 11-(6-chloro-8-methoxyquinolin-2-yl)undecan-1-ol, 11-(7-fluoro-8-methoxyquinolin-2-yl)undecan-1-ol, 11-(7-chloro-8-methoxyquinolin-2-yl)undecan-1-ol, 11-(5-chloro-6,8-dimethoxyquinolin-2-yl)undecan-1-ol, 11-(6-chloro-5,8-dimethoxyquinolin-2-yl)undecan-1-ol, 11-(5,7-dichloro-8-methoxyquinolin-2-yl)undecan-1-ol, 9-(8-ethoxyquinolin-2-yl)nonan-1-ol, 10-(8-ethoxyquinolin-2-yl)decan-1-ol, 11-(8-ethoxyquinolin-2-yl)undecan-1-ol, 12-(8-ethoxyquinolin-2-yl)dodecan-1-ol, 13-(8-ethoxyquinolin-2-yl)tridecan-1-ol, 14-((8-ethoxyquinolin-2-yl)tetradecan-1-ol, 15-(8-ethoxyquinolin-2-yl)pentadecan-1-ol, 11-(8-ethoxy-5-methylquinolin-2-yl)undecan-1-ol, 11-(8-ethoxy-5-fluoroquinolin-2-yl)undecan-1-ol, 9-(5-chloro-8-ethoxyquinolin-2-yl)nonan-1-ol, 11-(5-chloro-8-ethoxyquinolin-2-yl)undecan-1-ol, 15-(5-chloro-8-ethoxyquinolin-2-yl)pentadecan-1-ol, 11-(5-bromo-8-ethoxyquinolin-2-yl)undecan-1-ol, 11-(5,7-dichloro-8-ethoxyquinolin-2-yl)undecan-1-ol, 9-(8-isopropoxyquinolin-2-yl)nonan-1-ol, 10-(8-isopropoxyquinolin-2-yl)decan-1-ol, 11-(8-isopropoxyquinolin-2-yl)undecan-1-ol, 12-(8-isopropoxyquinolin-2-yl)dodecan-1-ol, 13-(8-isopropoxyquinolin-2-yl)tridecan-1-ol, 14-((8-isopropoxyquinolin-2-yl)tetradecan-1-ol, 15-(8-isopropoxyquinolin-2-yl)pentadecan-1-ol, 11-(8-isopropoxy-5-methylquinolin-2-yl)undecan-1-ol, 11-(5-fluoro-8 isopropoxyquinolin-2-yl)undecan-1-ol, 9-(5-chloro-8-isopropoxyquinolin-2-yl)nonan-1-ol, 11-(5-chloro-8-isopropoxyquinolin-2-yl)undecan-1-ol, 15-(5-chloro-8-isopropoxyquinolin-2-yl)pentadecan-1-ol, 11-(5-bromo-8-isopropoxyquinolin-2-yl)undecan-1-ol, 15-(5-chloro-8-isopropoxyquinolin-2-yl)pentadecan-1-ol, 11-(5-bromo-8-isopropoxyquinolin-2-yl)undecan-1-ol, 11-(5,7-dichloro-8-isopropoxyquinolin-2-yl)undecan-1-ol, 9-(8-(cyclopropylmethoxy)quinolin-2-yl)nonan-1-ol, 10-(8-(cyclopropylmethoxy)quinolin-2-yl)decan-1-ol, 11-(8-(cyclopropylmethoxy)quinolin-2-yl)undecan-1-ol, 12-(8-(cyclopropylmethoxy)quinolin-2-yl)dodecan-1-ol, 13-(8-cyclopropylmethoxy)quinolin-2-yl)tridecan-1-ol, 14-((8-cyclopropylmethoxy)quinolin-2-yl)tetradecan-1-ol, 15-(8-(cyclopropylmethoxy)quinolin-2-yl)pentadecan-1-ol, 11-(8-(cyclopropylmethoxy)-5-methylquinolin-2-yl)undecan-1-ol, 11-(8-(cyclopropylmethoxy)-5-fluoroquinolin-2-yl)undecan-1-ol, 9-(5-chloro-8-(cyclopropylmethoxy)quinolin-2-yl)nonan-1-ol, 11-(5-chloro-8-(cyclopropylmethoxy)quinolin-2-yl)undecan-1-ol, 15-(5-chloro-8-(cyclopropylmethoxy)quinolin-2-yl)pentadecan-1-ol, 11-(5-bromo-8-(cyclopropylmethoxy)quinolin-2-yl)undecan-1-ol, 11-(5,7-dichloro-8-(cyclopropylmethoxy)quinolin-2-yl)undecan-1-ol, 5,7-dichloro-2-(11-hydroxyundecyl)quinolin-8-ol, 10-(5-chloro-8-methoxyquinolin-2-yl)decan-1-ol, acetic acid 10-(5-chloro-8-methoxyquinolin-2-yl)decyl ester, 11-(5-chloro-8-methoxyquinolin-2-yl)undecan-1-ol, acetic acid 11-(5-chloro-8-methoxyquinolin-2-yl)undecyl ester, 12-(5-chloro-8-methoxyquinolin-2-yl)dodecan-1-ol, acetic acid 12-(5-chloro-8-methoxyquinolin-2-yl)dodecyl ester, 13-(5-chloro-8-methoxyquinolin-2-yl)tridecan-1-ol, acetic acid 13-(5-chloro-8-methoxyquinolin-2-yl)tridecyl ester, 11-(8-methoxyquinolin-4-(-yl)undecan-1-ol, 11-(8-ethoxyquinolin-4-(-yl)undecan-1-ol, 11-(8-isopropoxyquinolin-4-(-yl)undecan-1-ol, 11-(8-(cyclopropylmethoxy)quinolin-4-(-yl)undecan-1-ol, 11-(8-(benzyloxy)quinolin-4-(-yl)undecan-1-ol, 12-(8-(benzyloxy)quinolin-4-(-yl)dodecan-1-ol, 4-((11-hydroxyundecyl)quinolin-8-ol, 4-((12-hydroxydodecyl)quinolin-8-ol, 9-(8-(trifluoromethoxy)quinolin-2-yl)nonan-1-ol, 11-(8-(trifluoromethoxy)quinolin-2-yl)undecan-1-ol, 14-((8-(trifluoromethoxy)quinolin-2-yl)tetradecan-1-ol, 15-(8-trifluoromethoxy)quinolin-2-yl)pentadecan-1-ol, 2-((4-((2-hydroxyethyl)piperazin-1-yl)methyl)quinolin-8-ol, 2-(4-(((5-chloro-8-methoxyquinolin-2-yl)methyl)piperazin-1-yl)ethanol, 2-(4-(((5-chloro-8-ethoxyquinolin-2-yl)methyl)piperazin-1-yl)ethanol, 2-(4-(((5-chloro-8-isopropoxyquinolin-2-yl)methyl)piperazin-1-yl)ethanol, 2-(4-(((5-chloro-8-(cyclopropylmethoxy)quinolin-2-yl)methyl)piperazin-1-yl)ethane, 2-(4-(((5,7-dichloro-8-methoxyquinolin-2-yl)methyl)piperazin-1-yl)ethanol, 2-(4-(((5,7-dichloro-8-(cyclopropylmethoxy)quinolin-2-yl)methyl)piperazin-1-yl)ethanol, 2-((methyl(prop-2-ynyl)amino)methyl)quinolin-8-ol, 5-chloro-2((methyl(prop-2-ynyl)amino)methyl)quinolin-8-ol, N((5-chloro-8-methoxyquinolin-2-yl)methyl)-N-methylprop-2-yn-1-amine, N((5-chloro-8-ethoxyquinolin-2-yl)methyl)-N-methylprop-2-yn-1-amine, N((5-chloro-8-isopropoxyquinolin-2-yl)methyl)-N-methylprop-2-yn-1-amine, N((5-chloro-8-(cyclopropylmethoxy)quinolin-2-yl)methyl)-N-methylprop-2-yn-1-amine, N((5,7-dichloro-8-methoxyquinolin-2-yl)methyl)-N-methylprop-2-yn-1-amine, N((5,7-dichloro-8-(cyclopropylmethoxy)quinolin-2-yl)methyl)-N-methoxyprop-2-yn-1-amine, 8-((5-chloro-8-methoxyquinolin-2-yl)methylamino)octan-1-ol, 8-((5-chloro-8-ethoxyquinolin-2-yl)methylamino)octan-1-ol, 8-((5-chloro-8-isopropoxyquinolin-2-yl)methylamino)octan-1-ol, 8-((5-chloro-8-(cyclopropylmethoxy)quinolin-2-yl)methylamino)octan-1-ol, 8-((5,7-dichloro-8-methoxyquinolin-2-yl)methylamino)octan-1-ol, 8-((5,7-dichloro-8-(cyclopropylmethoxy)quinolin-2-yl)methylamino)octan-1-ol, and 6-(bis((8-methoxyquinolin-2-yl)methyl)amino)hexan-1-ol.

In another aspect, the invention relates to a composition comprising a compound as aforementioned, or a pharmaceutically, acceptable salt, a solvate or hydrate, a prodrug, or a metabolite thereof and a pharmaceutically acceptable diluent or carrier for use in treating a neurodegenerative disease.

In one embodiment of the invention, the neurodegenerative disease is selected from the group consisting of Alzheimer's disease, amyotrophic lateral sclerosis (ALS), cataract, cognitive disorder, cerebral ischaemia stroke, cerebral palsy, stroke, haemorrhagic stroke, Creutzfeldt-Jacob disease, spongiform encephalopathy, Mad Cow disease, dementia, depression, Down's syndrome, epilepsy, post-traumatic epilepsy, frontotemporal dementia, Gilles de la Tourette's syndrome, Hallerboden-Spatz disease, Huntington's disease, Lewy body disease, Parkinson's disease, cognitive impairment, learning deficit, macular degeneration, memory deficit, multiple sclerosis, multiple system atrophy, motor neuron disease. Pick's disease, progressive supranuclear palsy, pseudo dementia, retinopathy, senile dementia, schizophrenia transient anoxial induced neurodegeneration, pain, brain traumatic injury, and spinal cord injury.

CHEMISTRY

Example 1

Preparation of (8-benzyloxyquinolin-2-yl) and (8-hydroxyquinolin-2-yl)alkyl alcohol

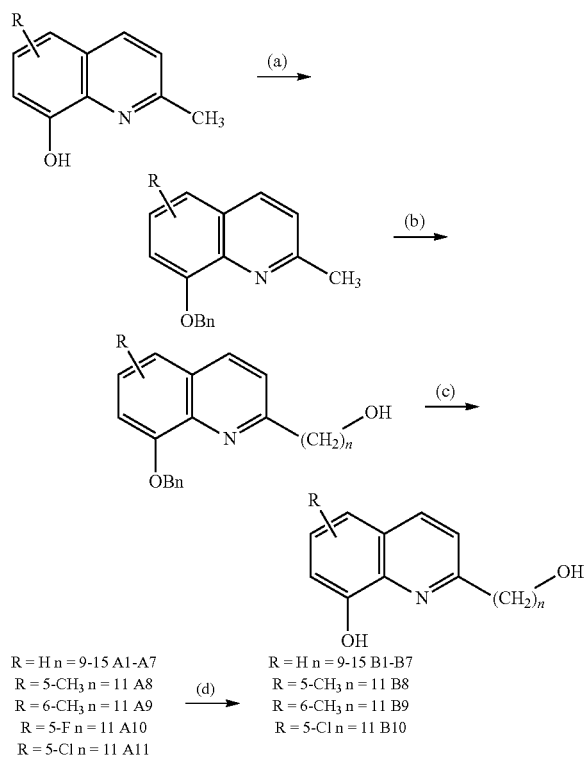

Reagents and Conditions:
(a) BnBr, KOH, EtOH, reflux, 15 h.; (b) 1) LHMDS, THF, 0° C., 1 h.; 2) Br(CH$_2$)$_{n-1}$OH, rt, 16-36 h.; (c) H$_2$, Pd/C, MeOH, rt, 6 to 10 h.; (d) BCl$_3$, CH$_2$Cl$_2$, 0° C. to rt, 3 h.

Method:

The benzylation was performed as described by G. Serratrice et al. [*Tetrahedron,* 1996, 52, 4659-4672]. Benzyl bromide (6.45 g, 37.7 mmol) was added to a stirred solution of 2-methylquinaldine (5.0 g, 31.4 mmol) and KOH (1.95 g, 34.8 mmol) in 60 ml EtOH under reflux condition. After 15 h, the reaction mixture was filtered and filtrate removed in vacuo. The residue was purified by flash column chromatography with Hex/EA (6:1) and recrystallized in Hexane to give intermediate. LHMDS (2.2 to 2.5 equiv.) was treated with a stirred solution of (1 equiv.) in 20 ml THF at 0° C. for 1 h. Corresponding Br(CH$_2$)$_{n-1}$OH (1.0 to 1.2 equiv.) was added to a reaction mixture and the temperature was recovered to room temperature (RT) for further 15 to 36 h. The solvent was removed under a reduced pressure. The brown oily residue was purified by flash column chromatography with Hex/EA (3:1 to 2:1) or DCM/EA (15:1 to 9:1) and recrystallized by Hexane/EA to afford series of compounds A. Removal of benzyl group of series of compounds A was carried out in the presence of 10% Pd/C under hydrogen at RT for 6-10 h. The reaction mixture was filtered off and the filtrate purified by flash column chromatography by Hex/EA (4:1 to 3:1) to give series compound of B. To a stirred solution of A11 (0.65 g, 1.4 mmol) in 20 ml CH$_2$Cl$_2$ was added 1M BCl$_3$ (2.8 ml, 2.8 mmol) at an ice bath for 3 h. The reaction mixture was poured into an ice bath and extracted by 50 ml CH$_2$Cl$_2$. The organic layer was concentrated in vacuum and residue purified by flash column chromatography (EA) to afford the product (0.31 g, 60%).

9-(8-benzyloxy)quinolin-2-yl)nonan-1-ol (A1)

Yield (YD): 53%. $^1$H NMR (400 MHz, d4-MeOD) δ8.15 (d, J=8.4 Hz, 1H), 7.52 (d, J=6.8 Hz, 2H), 7.31~7.41 (m, 5H), 7.29 (d, J=2.0 Hz, 1H), 7.15 (dd, J=7.6, 2.0 Hz, 1H), 5.40 (s, 2H), 3.52 (t, J=6.8 Hz, 2H), 3.00 (t, J=8.0 Hz, 2H), 1.80 (quin, J=6.8 Hz, 2H), 1.50 (t, J=7.2 Hz, 2H), 1.28-1.42 (br, 11H); MS. m/z 400.0, [M+Na]$^+$.

10-(8-benzyloxy)quinolin-2-yl)decan-1-ol (A2)

YD: 41%. $^1$H NMR (400 MHz, d4-MeOD) δ8.14 (d, J=8.4 Hz, 1H), 7.52 (d, J=7.6 Hz, 2H), 7.32-7.42 (m, 5H), 7.28 (t, J=7.2 Hz, 1H), 7.14 (dd, J=7.6, 1.2 Hz, 1H), 5.38 (s, 2H), 3.51 (t, J=6.8 Hz, 2H), 2.98 (t, J=8.0 Hz, 2H), 1.79 (quin, J=7.2 Hz, 2H), 1.49 (t, J=6.8 Hz, 2H), 1.29-1.40 (br, 13H); MS. m/z 414.0, [M+Na]$^+$.

11-(8-(benzyloxy)quinolin-2-yl)undecan-1-ol (A3)

YD: 42%. $^1$H NMR (400 MHz, CDCl$_3$) δ8.02 (d, J=8.4 Hz, 1H), 7.53 (d, J=7.2 Hz, 2H), 7.27-7.39 (m, 6H), 7.02 (d, J=7.6 Hz, 1H), 5.46 (s, 2H), 3.63 (t, J=6.8 Hz, 2H), 3.05 (t, J=8 Hz, 2H), 1.84 (q, J=7.6 Hz, 3H), 1.56 (t, J=7.2 Hz, 2H), 1.29-1.46 (m, 12H); MS. m/z 428.3, [M+Na]$^+$.

12-(8-(benzyloxy)quinolin-2-yl)dodecan-1-ol (A4)

YD: 44%. $^1$H NMR (400 MHz, d4-MeOD) δ8.13 (d, J=8.4 Hz, 1H), 7.52 (d, J=7.6 Hz, 2H), 7.31-7.40 (m, 5H), 7.26 (d, J=7.6 Hz, 1H), 7.13 (dd, J=7.6, 0.8 Hz, 1H), 5.37 (s, 2H), 3.51 (t, J=6.8 Hz, 2H), 2.98 (t, J=7.6 Hz, 2H), 1.78 (quin, 7.2 Hz, 2H), 1.49 (quin, J=7.2 Hz, 2H), 1.25-1.41 (m, 17H); MS. m/z 442.3, [M+Na]$^+$.

13-(8-(benzyloxy)quinolin-2-yl)tridecan-1-ol (A5)

YD: 40%. $^1$H NMR (400 MHz, CDCl$_3$) δ7.95 (d, J=8.4 Hz, 1H), 7.45 (d, J=7.6 Hz, 2H), 7.19-7.30 (m, 5H), 6.93 (d, J=7.6 Hz, 1H), 5.40 (s, 2H), 3.55 (t, J=6.8 Hz, 2H), 2.99 (t, J=7.6 Hz, 2H), 1.77 (quin, J=7.6 Hz, 2H), 1.46 (t, J=6.8 Hz, 2H), 1.19-1.38 (br, 19H); MS. m/z 456.3, [M+Na]$^+$.

14-(8-benzyloxy)quinolin-2-yl)tetradecan-1-ol (A6)

YD: 51%. $^1$H NMR (400 MHz, d4-MeOD) δ8.14 (d, J=8.4 Hz, 1H), 7.52 (d, J=7.2 Hz, 2H), 7.33-7.42 (m, 5H), 7.28 (t, J=7.2 Hz, 1H), 7.14 (d, J=6.8 Hz, 1H), 5.38 (s, 2H), 3.52 (t, J=6.4 Hz, 2H), 2.98 (t, J=8.0 Hz, 2H), 1.50 (quin, J=6.8 Hz, 2H), 1.47 (t, J=6.8 Hz, 2H), 1.22-1.4 (br, 21H); MS. m/z 447.3, [M+H]$^+$.

15-(8-(benzyloxy)quinolin-2-yl)pentadecan-1-ol (A7)

YD: 42%. $^1$H NMR (400 MHz, d4-MeOD) δ 8.15 (d, J=8.4 Hz, 1H), 7.53 (d, J=7.2 Hz, 2H), 7.35-7.43 (m, 5H), 7.28-7.33 (m, 1H), 7.15 (dd, J=7.6, 1.6 Hz, 1H), 5.39 (s, 2H), 3.52 (t, J=6.8 Hz, 2H), 2.99 (t, J=8.0 Hz, 2H), 1.79 (quin, J=6.8 Hz, 2H), 1.51 (quin, J=6.8 Hz, 2H), 1.22-1.41 (br, 23H); MS. m/z 462.3, [M+H]$^+$.

11-(8-(benzyloxy)-5-methylquinolin-2-yl)undecan-1-ol (A8)

YD: 47%. $^1$H NMR (400 MHz, d4-MeOD) δ 8.30 (d, J=8.4 Hz, 1H), 7.52 (d, J=7.2 Hz, 2H), 7.44 (d, J=8.8 Hz, 1H), 7.26-7.36 (m, 3H), 7.17 (d, J=8.0 Hz, 2H), 7.02 (d, J=8.0 Hz, 2H), 5.36 (s, 2H), 3.52 (t, J=6.4 Hz, 2H), 3.00 (t, J=7.6 Hz, 2H), 2.55 (s, 3H), 1.80 (quin, J=7.2 Hz, 2H), 1.50 (quin, J=6.8 Hz, 2H), 1.28-1.41 (m, 15H); MS. m/z 420.3, [M+H]$^+$.

11-(8-(benzyloxy)-6-methylquinolin-2-yl)undecan-1-ol (A9)

YD: 40%. $^1$H NMR (400 MHz, d4-MeOD) δ 8.03 (d, J=8.4 Hz, 1H), 7.53 (d, J=7.2 Hz, 2H), 7.33-7.37 (m, 3H), 7.26-7.30 (m, 1H), 7.16 (s, 1H), 7.00 (d, J=1.2 Hz, 2H), 5.36 (s, 2H), 3.51 (t, J=6.8 Hz, 2H), 2.95 (t, J=7.6 Hz, 2H), 2.40 (s, 3H), 1.76 (q, J=7.6 Hz, 2H), 1.56 (t, J=7.2 Hz, 2H), 1.29-1.46 (m, 15H); MS. m/z 442.3, [M+Na]$^+$.

11-(8-benzyloxy)-5-fluoroquinolin-2-yl)undecan-1-ol (A10)

YD: 43%. $^1$H NMR (400 MHz, CDCl$_3$) δ 8.28 (d, J=8.8 Hz, 1H), 7.51 (d, J=7.2 Hz, 2H), 7.33-7.40 (m, 3H), 7.28 (t, J=8.0 Hz, 1H), 6.89~6.98 (m, 2H), 5.42 (s, 2H), 3.61 (t, J=6.4 Hz, 2H), 3.07 (t, J=8 Hz, 2H), 1.83 (q, J=7.6 Hz, 2H), 1.51-1.54 (m, 2H), 1.21-1.45 (m, 15H); MS. m/z 446.2, [M+Na]$^+$.

11-(8-(benzyloxy)-5-chloroquinolin-2-yl)undecan-1-ol (A11)

YD: 43%. $^1$H NMR (400 MHz, d4-MeOD) δ 8.48 (d, J=8.8 Hz, 1H), 7.52-7.57 (m, 3H), 7.46 (d, J=8.4 Hz, 1H), 7.35~7.39 (m, 2H), 7.31 (d, J=7.2 Hz, 1H), 7.14 (d, J=8.4 Hz, 1H), 5.40 (s, 2H), 3.52 (t, J=6.8 Hz, 2H), 3.03 (t, J=7.6 Hz, 2H), 1.81 (quin, J=7.2 Hz, 2H), 1.49 (t, J=6.8 Hz, 2H), 1.28-1.41 (m, 15H); MS. m/z 462.2, [M+Na]$^+$.

2-(9-hydroxynonyl)quinolin-8-ol (B1)

YD: 85%. $^1$H NMR (400 MHz, d4-MeOD) δ 7.86 (d, J=8.4 Hz, 1H), 7.22 (t, J=7.6 Hz, 1H), 7.03-7.13 (m, 3H), 3.50 (t, J=6.8 Hz, 2H), 2.75 (t, J=8.0 Hz, 2H), 1.58 (quin, J=6.8 Hz, 2H), 1.44 (quin, J=6.8 Hz, 2H), 1.10-1.20 (m, 11H); HRMS (ESI): Calcd for [C$_{18}$H$_{25}$NO$_2$—Na]$^+$: 310.1778. Found: 310.1779.

2-(10-hydroxydecyl)quinolin-8-ol (B2)

YD: 85%. $^1$H NMR (400 MHz, CDCl$_3$) δ 8.01 (d, J=8.4 Hz, 1H), 7.35 (t, J=6.8 Hz, 1H), 7.26-7.28 (m, 2H), 7.11 (d, J=7.2 Hz, 1H), 3.60 (t, J=6.4 Hz, 2H), 2.92 (t, J=7.6 Hz, 2H), 1.79 (quin, J=6.8 Hz, 2H), 1.53 (quin, J=6.8 Hz, 2H), 1.27-1.33 (br, 14H); MS. m/z 302.2, [M+H]$^+$.

2-(11-hydroxyundecyl)quinolin-8-ol (B3)

YD: 77%. $^1$H NMR (400 MHz, CDCl$_3$) δ 8.04 (d, J=8.4 Hz, 1H), 7.38 (t, J=7.8 Hz, 1H), 7.27-7.31 (m, 2H), 7.14 (dd, J=1.2, 7.6 Hz, 1H), 3.64 (t, J=6.8 Hz, 2H), 2.95 (t, J=7.8 Hz, 2H), 1.83 (quin, J=7.8 Hz, 2H), 1.55 (m, 2H), 1.28-1.36 (br, 17H); $^1$MS. m/z 316.2, [M+H]$^+$.

2-(12-hydroxydodecyl)quinolin-8-ol (B4)

YD: 76%. $^1$H NMR (400 MHz, CDCl$_3$) δ 8.03 (d, J=8.4 Hz, 1H), 7.36 (t, J=8 Hz, 1H), 7.25-7.30 (m, 2H), 7.13 (d, J=7.6 Hz, 1H), 3.62 (t, J=6.4 Hz, 2H), 2.94 (t, J=7.6 Hz, 2H), 1.81 (quin, J=7.6 Hz, 2H), 1.54 (quin, J=6.8 Hz, 2H), 1.29-1.38 (br, 18H); MS. m/z 330.3, [M+H]$^+$.

2-(13-hydroxytridecyl)quinolin-8-ol (B5)

YD: 84%. $^1$H NMR (400 MHz, CDCl$_3$) δ 8.03 (d, J=8.4 Hz, 1H), 7.36 (t, J=7.6 Hz, 1H), 7.26-7.30 (m, 2H), 7.13 (d, J=7.6 Hz, 1H), 3.62 (t, J=6.8 Hz, 2H), 2.95 (t, J=7.6 Hz, 2H), 1.81 (quin, J=7.2 Hz, 2H), 1.54 (quin, J=6.8 Hz, 2H), 1.25-1.34 (br, 20H); MS. m/z 344.3, [M+H]$^+$.

2-(14-hydroxytetradecyl)quinolin-8-ol (B6)

YD: 87%. $^1$H NMR (400 MHz, CDCl$_3$) δ 8.02 (d, J=8.8 Hz, 1H), 7.36 (t, J=7.6 Hz, 1H), 7.25-7.29 (m, 2H), 7.12 (d, J=7.2 Hz, 1H), 3.61 (t, J=6.4 Hz, 2H), 2.94 (t, J=7.6 Hz, 2H), 1.80 (quin, J=7.2 Hz, 2H), 1.54 (quin, J=6.8 Hz, 2H), 1.24-1.34 (br, 24H); MS. m/z 358.3, [M+H]$^+$.

2-(15-hydroxypentadecyl)quinolin-8-ol (B7)

YD: 83%. $^1$H NMR (400 MHz, CDCl$_3$) δ 8.04 (d, J=8.4 Hz, 1H), 7.35 (t, J=7.6 Hz, 1H), 7.26-7.29 (m, 2H), 7.13 (d, J=7.2 Hz, 1H), 3.62 (t, J=6.8 Hz, 2H), 2.95 (t, J=7.6 Hz, 2H), 1.80 (quin, J=7.2 Hz, 2H), 1.54 (quin, J=6.8 Hz, 2H), 1.24-1.37 (br, 24H); MS. m/z 372.3, [M+H]$^+$.

2-(11-hydroxyundecyl)-5-methylquinolin-8-ol (B8)

YD: 83%. $^1$H NMR (400 MHz, d4-MeOD) δ 8.26 (d, J=8.4 Hz, 1H), 7.39 (d, J=8.8 Hz, 1H), 7.15 (d, J=7.2 Hz, 1H), 6.93 (d, J=3.2 Hz, 1H), 3.52 (t, J=6.4 Hz, 2H), 2.95 (t, J=8.0 Hz, 2H), 2.53 (s, 3H), 1.81 (quin, J=7.2 Hz, 2H), 1.48 (quin, J=6.8 Hz, 2H), 1.13-1.37 (m, 15H); MS. m/z 330.3, [M+H]$^+$.

2-(11-hydroxyundecyl)-6-methylquinolin-8-ol (B9)

YD: 83%. $^1$H NMR (400 MHz, d4-MeOD) δ 7.99 (d, J=8.4 Hz, 1H), 7.29 (d, J=8.8 Hz, 1H), 7.06 (s, 1H), 6.91 (s, 1H), 3.51 (t, J=6.4 Hz, 2H), 2.90 (t, J=8.0 Hz, 2H) 2.41 (s, 3H), 1.77 (quin, J=6.4 Hz, 2H), 1.49 (quin, J=6.8 Hz, 2H), 1.25-1.37 (m, 19H); MS. m/z 352.2, [M+Na]$^+$.

5-chloro-2-(11-hydroxyundecyl)quinolin-8-ol (B10)

$^1$H NMR (400 MHz, d4-MeOD) δ 8.39 (d, J=8.8 Hz, 1H), 7.49 (d, J=8.8 Hz, 1H), 7.41 (d, J=8.4 Hz, 1H), 7.01 (d, J=8.0 Hz, 1H), 3.51 (t, J=6.4 Hz, 2H), 2.98 (t, J=8.0 Hz, 2H), 1.81

(quin, J=7.2 Hz, 2H), 1.50 (quin, J=6.8 Hz, 2H), 1.27-1.35 (m, 15H); MS. m/z 350.2, [M+H]⁺.

Example 2

Preparation of (8-methoxyquinol-2-yl)alkyl alcohols

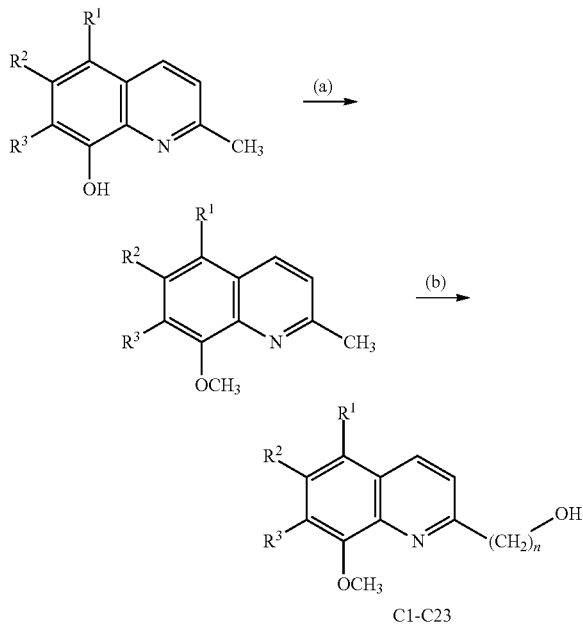

Reagents and Conditions:
(a) MeI, K₂CO₃, acetone, r.t, 10 h.; (b) 1) LHMDS, THF, 0° C., 1 h.; 2) Br(CH₂)$_{n-1}$OH, rt, 12-30 h.

Method:
Methyl iodide (10.8 g, 76.3 mmol) was added to a stirred solution of 2-methylquinaldine (1.0 g, 6.3 mmol) and K₂CO₃ (5.0 g, 36.2 mmol) in 30 ml acetone at RT for 10 h. The reaction mixture was filtered and filtrate removed under a reduced pressure. The residue was purified by flash column chromatography with Hex/EA (3:1) and recrystallized with Hexane/EA to give 8-methoxy-2-methylquinoline as intermediates. LHMDS (2.2 to 2.5 equiv.) was treated with a stirred solution of intermediate (1 equiv.) in THF at 0° C. for 1 h. Corresponding Br(CH₂)$_{n-1}$OH (1.0 to 1.2 equiv.) was added to a reaction mixture and recover to RT for further 12 to 30 h. The solvent was removed under a reduced pressure. The brown oily residue was purified by flash column chromatography with Hex/EA or DCM/EA and recrystallized by Hex/EA to afford series of compounds C.

9-(8-methoxyquinolin-2-yl)nonan-1-ol (C1)

YD: 50%. ¹H NMR (400 MHz, CDCl₃) δ 8.05 (d, J=8.4 Hz, 1H), 7.33-7.42 (m, 3H), 7.04 (d, J=6.8 Hz, 1H), 4.08 (s, 3H), 3.62 (t, J=6.4 Hz, 2H), 3.07 (t, J=7.6 Hz, 2H), 1.79 (br, 2H), 1.53 (br, 2H), 1.30-1.42 (br, 11H); MS. m/z 324.0, [M+Na]⁺.

10-(8-methoxyquinolin-2-yl)decan-1-ol (C2)

YD: 38%. ¹H NMR (400 MHz, CDCl₃) δ 8.01 (d, J=8.4 Hz, 1H), 7.36 (t, J=7.6 Hz, 1H), 7.30-7.33 (m, 2H), 7.00 (d, J=7.6 Hz, 1H), 4.05 (s, 3H), 3.60 (t, J=6.8 Hz, 2H), 3.01 (t, J=7.6 Hz, 2H), 1.79 (quin, J=8 Hz, 2H), 1.52 (quin, J=6.8 Hz, 2H), 1.30-1.43 (br, 12H); MS. m/z 316.2, [M+H]⁺.

11-(8-methoxyquinolin-2-yl)undecan-1-ol (C3)

YD: 42%. ¹H NMR (400 MHz, CDCl₃) δ 8.02 (d, J=8.8 Hz, 1H), 7.38 (t, J=7.8 Hz, 1H), 7.31-7.34 (m, 2H), 7.15 (d, J=7.2 Hz, 1H), 4.06 (s, 3H), 3.61 (t, J=6.8 Hz, 2H), 3.02 (t, J=7.8 Hz, 2H), 1.79 (quin, J=7.6 Hz, 2H), 1.54 (quin, J=6.8 Hz, 2H), 1.31-1.42 (br, 15H); MS. m/z 352.2, [M+Na]⁺.

12-(8-methoxyquinolin-2-yl)dodecan-1-ol (C4)

YD: 38%. ¹H NMR (400 MHz, CDCl₃) δ 8.01 (d, J=8.8 Hz, 1H), 7.35 (t, J=7.6 Hz, 1H), 7.30-7.32 (m, 2H), 7.01 (d, J=7.2 Hz, 1H), 4.05 (s, 3H), 3.61 (t, J=6.4 Hz, 2H), 3.01 (t, J=8 Hz, 2H), 1.78 (quin, J=7.6 Hz, 2H), 1.36-1.41 (m, 2H), 1.24-1.33 (br, 16H); MS. m/z 344.3, [M+H]⁺.

13-(8-methoxyquinolin-2-yl)tridecan-1-ol (C5)

YD: 38%. ¹H NMR (400 MHz, CDCl₃) δ 8.01 (d, J=8.4 Hz, 1H), 7.37 (t, J=7.6 Hz, 1H), 7.30-7.33 (m, 2H), 7.01 (d, J=7.6 Hz, 1H), 4.05 (s, 3H), 3.61 (t, J=7.2 Hz, 2H), 3.01 (t, J=8 Hz, 2H), 1.80 (quin, J=7.6 Hz, 2H), 1.54 (quin, J=6.8 Hz, 2H), 1.36-1.43 (br, 19H); MS. m/z 358.3, [M+H]⁺.

14-(8-methoxyquinolin-2-yl)tetradecan-1-ol (C6)

YD: 38%. ¹H NMR (400 MHz, CDCl₃) δ 8.02 (d, J=8.4 Hz, 1H), 7.31-7.38 (m, 3H), 7.01 (d, J=7.2 Hz, 1H), 4.06 (s, 3H), 3.61 (t, J=6.8 Hz, 2H), 3.02 (t, J=8 Hz, 2H), 1.79 (quin, J=7.6 Hz, 2H), 1.54 (quin, J=6.8 Hz, 2H), 1.23-1.40 (br, 21H); MS. m/z 394.3, [M+Na]⁺.

15-(8-methoxyquinolin-2-yl)pentadecan-1-ol (C7)

YD: 31%. ¹H NMR (400 MHz, CDCl₃) δ 8.01 (d, J=8.4 Hz, 1H), 7.31-7.39 (m, 3H), 7.01 (d, J=7.2 Hz, 1H), 4.06 (s, 3H), 3.63 (t, J=6.8 Hz, 2H), 3.02 (t, J=8 Hz, 2H), 1.79 (quin, J=7.6 Hz, 2H), 1.54 (quin, J=6.8 Hz, 2H), 1.32-1.43 (br, 23H); MS. m/z 408.3, [M+H]⁺.

11-(8-methoxy-5-methylquinolin-2-yl)undecan-1-ol (C8)

YD: 30%. ¹H NMR (400 MHz, d4-MeOD) δ 8.29 (d, J=8.4 Hz, 1H), 7.43 (d, J=8.8 Hz, 1H), 7.24 (dd, J=8.0, 0.8 Hz, 1H), 7.01 (d, J=8.0 Hz, 1H), 4.00 (s, 3H), 3.51 (t, J=6.8 Hz, 2H), 2.97 (t, J=8.0 Hz, 2H), 2.56 (s, 3H), 1.76 (quin, J=7.6 Hz, 2H), 1.50 (quin, J=7.2 Hz, 2H), 1.27-1.40 (br, 15H); MS. m/z 366.2, [M+Na]⁺.

11-(5-fluoro-8-methoxyquinolin-2-yl)undecan-1-ol (C9)

¹H NMR (400 MHz, d4-MeOD) δ 8.34 (d, J=8.8 Hz, 1H), 7.51 (d, J=8.8 Hz, 1H), 7.15 (d, J=7.2 Hz, 1H), 6.93 (d, J=3.2 Hz, 1H), 4.02 (s, 3H), 3.52 (t, J=6.8 Hz, 2H), 2.95 (t, J=8.0 Hz, 2H), 1.81 (quin, J=7.2 Hz, 2H), 1.48 (quin, J=6.8 Hz, 2H), 1.13-1.37 (m, 15H); MS. m/z 370.2, [M+Na]⁺.

12-(5-fluoro-8-methoxyquinolin-2-yl)dodecan-1-ol (C10)

YD: 38%. ¹H NMR (400 MHz, d4-MeOD) δ 8.36 (d, J=8.8 Hz, 1H), 7.52 (d, J=8.8 Hz, 1H), 7.17 (d, J=8.8 Hz, 1H), 7.08

(dd, J=8.4, 4.8 Hz, 1H), 4.04 (s, 3H), 3.53 (t, J=6.8 Hz, 2H), 3.00 (t, J=8.0 Hz, 2H), 1.78 (quin, J=7.2 Hz, 2H), 1.51 (quin, J=7.2 Hz, 2H), 1.28-1.42 (m, 17H); MS. m/z 384.2, [M+Na]$^+$.

9-(5-chloro-8-methoxyquinolin-2-yl)nonan-1-ol (C11)

YD: 38%. $^1$H NMR (400 MHz, d4-MeOD) δ8.47 (d, J=8.8 Hz, 1H), 7.55 (d, J=8.8 Hz, 1H), 7.52 (d, J=8.4 Hz, 1H), 7.11 (d, J=8.8 Hz, 1H), 4.04 (s, 3H), 3.51 (t, J=6.8 Hz, 2H), 3.00 (t, J=8.0 Hz, 2H), 1.77 (quin, J=7.6 Hz, 2H), 1.50 (quin, J=6.8 Hz, 2H), 1.30-1.37 (m, 11H); MS. m/z 336.2, [M+H]$^+$.

11-(5-chloro-8-methoxyquinolin-2-yl)undecan-1-ol (C12)

YD: 35%. $^1$H NMR (400 MHz, d4-MeOD) δ8.46 (d, J=8.4 Hz, 1H), 7.54 (d, J=8.8 Hz, 1H), 7.51 (d, J=8.4 Hz, 1H), 7.10 (d, J=8.4 Hz, 1H), 4.04 (s, 3H), 3.51 (t, J=6.8 Hz, 2H), 2.99 (t, J=8.0 Hz, 2H), 1.76 (quin, J=7.6 Hz, 2H), 1.49 (quin, J=6.8 Hz, 2H), 1.27-1.38 (br, 15H); MS. m/z 386.2, [M+Na]$^+$.

15-(5-chloro-8-methoxyquinolin-2-yl)pentadecan-1-ol (C13)

YD: 39%. $^1$H NMR (400 MHz, d4-MeOD+CDCl$_3$) δ8.44 (d, J=8.4 Hz, 1H), 7.47 (d, J=8.4 Hz, 1H), 7.46 (d, J=8.4 Hz, 1H), 7.01 (dd, J=8.4, 4.0 Hz, 1H), 4.03 (s, 3H), 3.52 (t, J=6.8 Hz, 2H), 2.99 (t, J=8.0 Hz, 2H), 1.76 (quin, J=7.6 Hz, 2H), 1.50 (quin, J=6.8 Hz, 2H), 1.22-1.38 (m, 23H); MS. m/z 442.3, [M+Na]$^+$.

11-(5-bromo-8-methoxyquinolin-2-yl)undecan-1-ol (C14)

YD: 46%. $^1$H NMR (400 MHz, CDCl$_3$) δ8.40 (d, J=8.4 Hz, 1H), 7.65 (d, J=8.4 Hz, 1H), 7.44 (d, J=8.8 Hz, 1H), 6.91 (d, J=8.4 Hz, 1H), 4.06 (s, 3H), 3.63 (t, J=6.8 Hz, 2H), 3.07 (t, J=8.0 Hz, 2H), 1.79 (quin, J=7.6 Hz, 2H), 1.55 (quin, J=6.8 Hz, 2H), 1.30-1.45 (br, 15H); MS. m/z 430.2, [M+Na]$^+$.

11-(8-methoxy-5-(trifluoromethyl)quinolin-2-yl)undecan-1-ol (C15)

YD: 36%. $^1$H NMR (400 MHz, d4-MeOD+CDCl$_3$) δ8.40 (dq, J=10.4, 1.6 Hz, 1H), 7.86 (d, J=8.4 Hz, 1H), 7.58 (d, J=8.8 Hz, 1H), 7.20 (d, J=8.0 Hz, 1H), 4.11 (s, 3H), 3.51 (t, J=6.8 Hz, 2H), 3.00 (t, J=8.0 Hz, 2H), 1.78 (quin, J=7.6 Hz, 2H), 1.50 (quin, J=6.8 Hz, 2H), 1.27-1.43 (m, 15H); MS. m/z 420.2, [M+Na]$^+$.

11-(5,8-dimethoxyquinolin-2-yl)undecan-1-ol (C16)

YD: 31%; $^1$H NMR (400 MHz, d4-MeOD) δ8.46 (d, J=8.4 Hz, 1H), 7.38 (d, J=8.4 Hz, 1H), 7.03 (d, J=8.4 Hz, 1H), 6.82 (d, J=8.4 Hz, 1H), 3.98 (s, 3H), 3.94 (s, 3H), 3.51 (t, J=6.8 Hz, 2H), 2.95 (t, J=8.0 Hz, 2H), 1.73 (quin, J=7.6 Hz, 2H), 1.50 (quin, J=6.8 Hz, 2H), 1.27-1.35 (br, 15H); MS. m/z 360.2, [M+H]$^+$.

11-(8-methoxy-6-methylquinolin-2-yl)undecan-1-ol (C17)

YD: 41%. $^1$H NMR (400 MHz, CDCl$_3$) δ7.96 (d, J=8.4 Hz, 1H), 7.30 (t, J=8.4 Hz, 1H), 7.12 (s, 1H), 6.87 (s, 1H), 4.06 (s, 3H), 3.63 (t, J=6.8 Hz, 2H), 3.05 (t, J=7.6 Hz, 2H), 2.50 (s, 3H), 1.79 (quin, J=8.0 Hz, 2H), 1.55 (quin, J=6.8 Hz, 2H), 1.27-1.41 (br, 15H); MS. m/z 366.2, [M+Na]$^+$.

11-(6-fluoro-8-methoxyquinolin-2-yl)undecan-1-ol (C18)

YD: 41%; $^1$H NMR (400 MHz, d4-MeOD) δ8.12 (d, J=8.4 Hz, 1H), 7.44 (d, J=8.8 Hz, 1H), 7.07 (dd, J=9.2, 2.4 Hz, 1H), 7.01 (dd, J=10.8, 2.8 Hz, 1H), 4.06 (s, 3H), 3.52 (t, J=6.8 Hz, 2H), 2.95 (t, J=8.0 Hz, 2H), 1.75 (quin, J=7.6 Hz, 2H), 1.48 (quin, J=7.2 Hz, 2H), 1.19-1.35 (m, 15H); MS. m/z 348.2, [M+H]$^+$.

11-(6-chloro-8-methoxyquinolin-2-yl)undecan-1-ol (C19)

YD: 39%; $^1$H NMR (400 MHz, d4-MeOD) δ8.11 (d, J=8.4 Hz, 1H), 7.44-7.47 (m, 2H), 7.13 (d, J=2.0 Hz, 1H), 4.05 (s, 3H), 3.52 (t, J=6.8 Hz, 2H), 2.96 (t, J=8.0 Hz, 2H), 1.76 (quin, J=7.2 Hz, 2H), 1.50 (quin, J=6.8 Hz, 2H), 1.28-1.36 (br, 15H); MS. m/z 360.2, [M+H]$^+$.

11-(7-fluoro-8-methoxyquinolin-2-yl)undecan-1-ol (C20)

YD: 32%; $^1$H NMR (400 MHz, d4-MeOD) δ8.20 (d, J=8.8 Hz, 1H), 7.60 (dd, J=8.8, 5.6 Hz, 1H), 7.39 (dd, J=8.8, 1.6 Hz, 1H), 7.01 (d, J=8.8 Hz, 1H), 4.13 (d, J=1.2 Hz, 3H), 3.52 (t, J=6.8 Hz, 2H), 2.99 (t, J=7.6 Hz, 2H), 1.80 (quin, J=7.6 Hz, 2H), 1.48 (quin, J=7.2 Hz, 2H), 1.29-1.42 (m, 15H); MS. m/z 348.2, [M+H]$^+$.

11-(7-chloro-8-methoxyquinolin-2-yl)undecan-1-ol (C21)

YD: 17%; $^1$H NMR (400 MHz, d4-MeOD) δ8.20 (d, J=8.4 Hz, 1H), 7.60 (d, J=8.8 Hz, 1H), 7.50 (d, J=8.8 Hz, 1H), 7.42 (d, J=8.4 Hz, 1H), 4.08 (s, 3H), 3.52 (t, J=6.8 Hz, 2H), 2.99 (t, J=7.6 Hz, 2H), 1.82 (quin, J=7.2 Hz, 2H), 1.50 (quin, J=6.8 Hz, 2H), 1.28-1.42 (br, 15H); MS. m/z 360.2, [M+H]$^+$.

11-(5-chloro-6,8-dimethoxyquinolin-2-yl)undecan-1-ol (C22)

YD: 32%; $^1$H NMR (400 MHz, d4-MeOD) δ8.40 (d, J=8.8 Hz, 1H), 7.46 (d, J=8.8 Hz, 1H), 7.07 (s, 1H), 4.08 (s, 3H), 4.02 (s, 3H), 3.51 (t, J=6.8 Hz, 2H), 2.94 (t, J=7.6 Hz, 2H), 1.74 (quin, J=7.6 Hz, 2H), 1.50 (quin, J=6.8 Hz, 2H), 1.27-1.34 (br, 15H); MS. m/z 394.2, [M+H]$^+$.

11-(6-chloro-5,8-dimethoxyquinolin-2-yl)undecan-1-ol (C23)

YD: 35%; $^1$H NMR (400 MHz, d4-MeOD) δ8.38 (d, J=8.8 Hz, 1H), 7.51 (d, J=8.4 Hz, 1H), 7.12 (s, 1H), 4.02 (s, 3H), 3.94 (s, 3H), 3.52 (t, J=6.4 Hz, 2H), 2.97 (t, J=7.6 Hz, 2H), 1.74 (quin, J=7.6 Hz, 2H), 1.50 (quin, J=6.8 Hz, 2H), 1.34-1.41 (br, 15H); MS. m/z 394.2, [M+H]$^+$.

11-(5,7-dichloro-8-methoxyquinolin-2-yl)undecan-1-ol (C24)

YD: 40%. $^1$H NMR (400 MHz, CDCl$_3$) δ8.40 (d, J=8.4 Hz, 1H), 7.59 (d, J=8.0 Hz, 1H), 7.56 (s, 1H), 7.39 (d, J=8.8 Hz, 1H), 4.19 (s, 3H), 3.63 (t, J=6.8 Hz, 2H), 3.04 (t, J=7.6

2H), 1.84 (quin, 7.2 Hz, 2H), 1.55 (quin, J=6.8 Hz, 2H), 1.27-1.40 (br, 15H); MS. m/z 420.2, [M+Na]⁺.

Example 3

Preparation of (8-ethoxyquinol-2-yl) and (8-Isopropoxyquinol-2-yl)alkyl alcohols

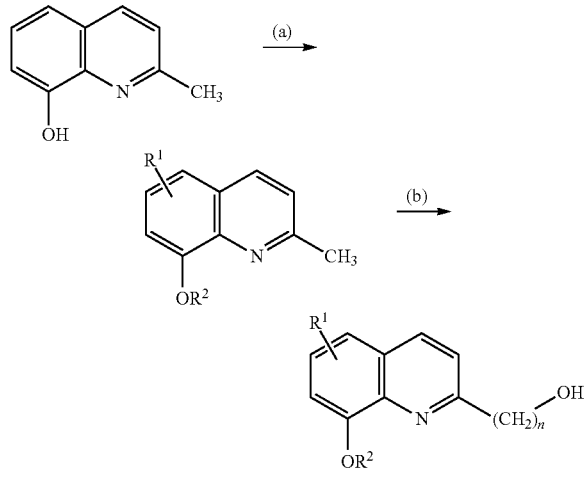

D1-D14 (R² = Et)
E1-E14 (R² = iPr)

Reagents and Conditions:
(a) Ethyl iodide or 2-bromopropane, K₂CO₃, DMF, 60° C., 14 h.; (b) 1) LHMDS, THF, 0° C., 1 h.; 2) Br(CH₂)ₙ₋₁OH, RT, 12-30 h.

Method:
Ethyl iodide (3.9 g, 25.0 mmol) or 2-bromopropane (2.4 g, 19.2 mmol) was added to a stirred solution of 2-methylquinaldine (3.0 g, 18.8 mmol) and K₂CO₃ (6.5 g 47 mmol; 5.2 g, 37.6 mmol) in 30 ml DMF at 60° C. for 14 h. The reaction mixture was quenched by H₂O (200 ml) and extracted with EtOAc (50 ml×2). The organic layer was concentrated by evaporation in vacuum. The residue was purified by flash column chromatography with Hex/EA (6:1) and recrystallized with Hexane/EA to give 8-ethoxy-2-methylquinoline as intermediate (2.75 g, 78%) in solid but liquid form for 8-isopropoxy-2-methylquinoline (2.92 g, 77%). LHMDS (2.2 equiv.) was treated with a stirred solution of different intermediates in THF solution at 0° C. for 1 h. Corresponding Br(CH₂)ₙ₋₁OH (1.1-1.2 equiv.) was added to a reaction mixture and recover to RT for further 12 to 30 h. The solvent was removed under a reduced pressure. The brown oily residue was purified by flash column chromatography with Hex/EA or DCM/BA and recrystallized by Hexane/EA to afford compound D and E.

9-(8-ethoxyquinolin-2-yl)nonan-1-ol (D1)

YD: 45%. ¹H NMR (400 MHz, CDCl₃) δ8.07 (d, J=8.0 Hz, 1H), 7.34-7.42 (m, 3H), 7.06 (d, J=8.4 Hz, 1H), 4.35 (q, J=6.8 Hz, 2H), 3.63 (t, J=6.8 Hz, 2H), 3.11 (br, 2H), 1.83 (quin, J=7.6 Hz, 2H), 1.52-1.64 (m, 5H), 1.26-1.46 (br, 11H); MS. m/z 338.0, [M+Na]⁺.

10-(8-ethoxyquinolin-2-yl)decan-1-ol (D2)

YD: 36%. ¹H NMR (400 MHz, d4-MeOD) δ8.16 (d, J=8.4 Hz, 1H), 7.38-7.44 (m, 3H), 7.14 (dd, J=7.2, 1.6 Hz, 1H), 4.29 (q, J=6.8 Hz, 2H), 3.52 (t, J=6.8 Hz, 2H), 2.99 (t, J=7.6 Hz, 2H), 1.78 (quin, J=7.6 Hz, 2H), 1.57 (t, J=7.6 Hz, 3H), 1.50 (t, J=7.6 Hz, 2H), 1.30-1.43 (br, 13H); MS. m/z 352.0, [M+Na]⁺.

11-(8-ethoxyquinolin-2-yl)undecan-1-ol (D3)

YD: 43%. ¹H NMR (400 MHz, CDCl₃) δ8.03 (d, J=7.6 Hz, 1H), 7.31-7.41 (m, 3H), 7.04 (d, J=7.2 Hz, 1H), 4.33 (q, J=7.2 Hz, 2H), 3.62 (t, J=6.4 Hz, 2H), 3.06 (br, 2H), 1.81 (quin, J=8.0 Hz, 2H), 1.51-1.61 (m, 6H), 1.38-1.51 (br, 14H); MS. m/z 344.3, [M+H]⁺.

12-(8-ethoxyquinolin-2-yl)dodecan-1-ol (D4)

YD: 33%. ¹H NMR (400 MHz, CDCl₃) δ8.03 (d, J=8.4 Hz, 1H), 7.31-7.39 (m, 3H), 7.04 (d, J=7.6 Hz, 1H), 4.33 (q, J=6.8 Hz, 2H), 3.62 (t, J=6.4 Hz, 2H), 3.05 (t, J=8.0 Hz, 2H), 1.82 (quin, J=7.2 Hz, 2H), 1.53-1.62 (m, 5H), 1.27-1.42 (br, 17H); MS. m/z 380.3, [M+Na]⁺.

13-(8-ethoxyquinolin-2-yl)tridecan-1-ol (D5)

YD: 43%. ¹H NMR (400 MHz, CDCl₃) δ8.04 (d, J=8.4 Hz, 1H), 7.32-7.40 (m, 3H), 7.04 (d, J=7.6 Hz, 1H), 4.34 (q, J=6.8 Hz, 2H), 3.62 (t, J=6.4 Hz, 2H), 3.07 (t, J=8.0 Hz, 2H), 1.82 (quin, J=7.6 Hz, 2H), 1.52-1.62 (m, 5H), 1.19-1.46 (br, 19H); MS. m/z 394.0, [M+Na]⁺.

14-(8-ethoxyquinolin-2-yl)tetradecan-1-ol (D6)

YD: 35%. ¹H NMR (400 MHz, CDCl₃) δ8.00 (d, J=8.4 Hz, 1H), 7.28-7.35 (m, 3H), 7.02 (d, J=7.2 Hz, 1H), 4.32 (q, J=6.8 Hz, 2H), 3.61 (t, J=6.4 Hz, 2H), 3.01 (t, J=8.0 Hz, 2H), 1.80 (quin, J=7.6 Hz, 2H), 1.52-1.60 (m, 5H), 1.24-1.41 (br, 21H); MS. m/z 408.3, [M+Na]⁺.

15-(8-ethoxyquinolin-2-yl)pentadecan-1-ol (D7)

YD: 33%. ¹H NMR (400 MHz, d4-MeOD) δ8.21 (d, J=8.4 Hz, 1H), 7.40-7.47 (m, 3H), 7.17 (dd, J=7.2, 1.6 Hz, 1H), 4.30 (q, J=7.2 Hz, 2H), 3.52 (t, J=6.8 Hz, 2H), 3.01 (t, J=7.6 Hz, 2H), 1.78 (quin, J=7.6 Hz, 2H), 1.57 (t, J=6.8 Hz, 3H), 1.51 (quin, J=6.8 Hz, 2H), 1.26-1.43 (br, 23H); MS. m/z 400.4, [M+Na]⁺.

11-(8-ethoxy-5-methylquinolin-2-yl)undecan-1-ol (D8)

YD: 34%. ¹H NMR (400 MHz, CDCl₃) δ8.20 (d, J=8.8 Hz, 1H), 7.36 (d, J=8.4 Hz, 1H), 7.19 (d, J=7.6 Hz, 1H), 6.94 (d, J=8.0 Hz, 1H), 4.31 (q, J=6.8 Hz, 2H), 3.63 (t, J=6.4 Hz, 2H), 3.08 (t, J=8.0 Hz, 2H), 2.57 (s, 3H), 1.83 (quin, J=7.6 Hz, 2H), 1.83 (t, J=7.6 Hz, 3H), 1.57 (quin, J=7.2 Hz, 2H), 1.41-1.45 (m, 2H), 1.28-1.33 (br, 13H), MS. m/z 380.2, [M+Na]⁺.

11-(8-ethoxy-5-fluoroquinolin-2-yl)undecan-1-ol (D9)

YD: 49%. ¹H NMR (400 MHz, d4-MeOD) δ8.33 (d, J=8.4 Hz, 1H), 7.49 (d, J=8.8 Hz, 1H), 7.12 (t, J=9.2 Hz, 1H), 7.05 (dd, J=8.4, 4.8 Hz, 1H), 4.25 (q, J=7.2 Hz, 2H), 3.51 (t, J=6.8 Hz, 2H), 2.99 (t, J=8.0 Hz, 2H), 1.77 (quin, J=7.2 Hz, 2H), 1.55 (t, J=7.2 Hz, 3H), 1.48-1.52 (m, 2H), 1.28-1.46 (br, 15H); MS. m/z 384.2, [M+Na]⁺.

9-(5-chloro-8-ethoxyquinolin-2-yl)nonan-1-ol (D10)

YD: 34%. ¹H NMR (400 MHz, d4-MeOD) δ8.47 (d, J=8.8 Hz, 1H), 7.55 (d, J=8.8 Hz, 1H), 7.50 (d, J=8.4 Hz, 1H), 7.10

(d, J=8.8 Hz, 1H), 4.28 (q, J=6.8 Hz, 2H), 3.51 (t, J=6.4 Hz, 2H), 3.01 (t, J=8.0 Hz, 2H), 1.76 (quin, J=7.6 Hz, 2H), 1.56 (t, J=6.8 Hz, 3H), 1.48-1.51 (m, 2H), 1.31-1.46 (br, 11H); MS. m/z 350.2, [M+H]$^+$.

11-(5-chloro-8-ethoxyquinolin-2-yl)undecan-1-ol (D11)

YD: 38%. $^1$H NMR (400 MHz, CDCl$_3$) δ8.35 (d, J=8.8 Hz, 1H), 7.36 (dd, J=8.4, 3.6 Hz, 1H), 7.19 (d, J=2.4 Hz, 1H), 6.88 (d, J=8.4 Hz, 1H), 4.25 (q, J=7.2 Hz, 2H), 3.56 (t, J=6.4 Hz, 2H), 2.98 (t, J=8.0 Hz, 2H), 1.76 (quin, J=8.0 Hz, 2H), 1.45-1.54 (m, 5H), 1.19-1.39 (br, 15H); MS. m/z 400.2, [M+Na]$^+$.

15-(5-chloro-8-ethoxyquinolin-2-yl)pentadecan-1-ol (D12)

YD: 38%. $^1$H NMR (400 MHz, d4-MeOD+CDCl$_3$) δ8.47 (d, J=8.8 Hz, 1H), 7.53 (d, J=8.8 Hz, 1H), 7.49 (d, J=8.4 Hz, 1H), 7.08 (d, J=8.4 Hz, 1H), 4.28 (q, J=6.8 Hz, 2H), 3.52 (t, J=6.8 Hz, 2H), 3.01 (t, J=8.0 Hz, 2H), 1.79 (quin, J=7.6 Hz, 2H), 1.57 (t, J=6.8 Hz, 3H), 1.49 (quin, J=6.8 Hz, 2H), 1.25-1.4.1 (br, 23H); MS. m/z 434.3, [M+H]$^+$.

11-(5-bromo-8-ethoxyquinolin-2-yl)undecan-1-ol (D13)

YD: 33%. $^1$H NMR (400 MHz, d4-MeOD) δ 8.41 (d, J=8.8 Hz, 1H), 7.67 (d, J=8.4 Hz, 1H), 7.52 (d, J=8.8 Hz, 1H), 7.04 (d, J=8.4 Hz, 1H), 4.2 (q, J=7.2 Hz, 2H), 3.52 (t, J=6.8 Hz, 2H), 3.00 (t, J=8.0 Hz, 2H), 1.77 (quin, J=7.6 Hz, 2H), 1.56 (t, J=7.2 Hz, 3H), 1.47-1.57 (m, 2H), 1.27-1.39 (br, 15H); MS. m/z 444.2, [M+Na]$^+$.

11-(5,7-dichloro-8-ethoxyquinolin-2-yl)undecan-1-ol (D14)

YD: 34%. $^1$H NMR (400 MHz, d4-MeOD) δ8.43 (d, J=8.8 Hz, 1H), 7.64 (s, 1H), 7.51 (d, J=8.4 Hz, 1H), 4.39 (q, J=6.8 Hz, 2H), 3.52 (t, J=6.8 Hz, 2H), 3.00 (t, J=7.2 Hz, 2H), 1.84 (quin, J=7.2 Hz, 2H), 1.45-1.49 (m, 5H), 1.27-1.36 (br, 15H); MS. m/z 434.2, [M+Na]$^+$.

9-(8-isopropoxyquinolin-2-yl)nonan-1-ol (E1)

YD: 28%. $^1$H NMR (400 MHz, CDCl$_3$) δ 8.07 (d, J=8.8 Hz, 1H), 7.33-7.36 (m, 1H), 7.31-7.33 (m, 2H), 7.09 (d, J=7.2 Hz, 1H), 4.79 (m, 1H), 3.49 (t, J=6.8 Hz, 2H), 2.93 (t, J=7.6 Hz, 2H), 1.71 (quin, J=7.6 Hz, 2H), 1.45-1.49 (m, 2H), 1.41 (d, J=6 Hz, 6H), 1.20-1.35 (br, 11H); MS. m/z 330.2, [M+H]$^+$.

10-(8-isopropoxyquinolin-2-yl)decan-1-ol (E2)

YD: 36%. $^1$H NMR (400 MHz, d4-MeOD) δ 8.14 (d, J=8.8 Hz, 1H), 7.40-7.43 (m, 1H), 7.37-7.39 (m, 2H), 7.16 (dd, J=6.8, 2.0 Hz, 1H), 4.83 (m, 1H), 3.51 (t, J=6.8 Hz, 2H), 2.98 (t, J=7.6 Hz, 2H), 1.77 (quin, J=7.2 Hz, 2H), 1.45-1.49 (m, 2H), 1.41 (d, J=6 Hz, 6H), 1.20-1.35 (br, 11H); MS. m/z 366.0, [M+Na]$^+$.

11-(8-isopropoxyquinolin-2-yl)undecan-1-ol (E3)

YD: 45%. $^1$H NMR (400 MHz, CDCl$_3$) δ7.99 (d, J=8.4 Hz, 1H), 7.34 (d, J=4.4 Hz, 2H), 7.24-7.27 (m, 1H), 7.09 (t, J=4.4 Hz, 1H), 4.82 (sept, J=6 Hz, 1H), 3.60 (t, J=6.8 Hz, 2H), 3.00 (t, J=7.6 Hz, 2H), 1.81 (quin, J=7.6 Hz, 2H), 1.51-1.56 (m, 2H), 1.47 (d, J=6 Hz, 6H), 1.33-1.43 (br, 15H); MS. m/z 380.3, [M+Na]$^+$.

12-(8-isopropoxyquinolin-2-yl)dodecan-1-ol (E4)

YD: 34%. $^1$H NMR (400 MHz, CDCl$_3$) δ8.05 (d, J=7.6 Hz, 1H), 7.30-7.39 (m, 3H), 7.13 (dd, J=6.4, 2.4 Hz, 1H), 4.85 (sept, J=6 Hz, 1H), 3.63 (t, J=6.8 Hz, 2H), 3.09 (br, 2H), 1.84 (quin, J=7.6 Hz, 2H), 1.56 (quin, J=7.2 Hz, 2H), 1.48 (d, J=6 Hz, 6H), 1.27-1.47 (br, 17H); MS. m/z 394.3, [M+Na]$^+$.

13-(8-isopropoxyquinolin-2-yl)tridecan-1-ol (E5)

YD: 34%. $^1$H NMR (400 MHz, d4-MeOD) δ8.11 (d, J=8.4 Hz, 1H), 7.35-7.41 (m, 3H), 7.14 (d, J=7.2 Hz, 1H), 4.81 (br, 1H), 3.52 (t, J=6.8 Hz, 2H), 2.96 (t, J=8.0 Hz, 2H), 1.75 (quin, J=7.2 Hz, 2H), 1.45-1.52 (m, 2H), 1.43 (d, J=6.0 Hz, 6H), 1.25-1.42 (br, 19H); MS. m/z 408.0, [M+Na]$^+$.

14-(8-isopropoxyquinolin-2-yl)tetradecan-1-ol (E6)

YD: 36%. $^1$H NMR (400 MHz, d4-MeOD) δ8.13 (d, J=8.8 Hz, 1H), 7.37-7.43 (m, 3H), 7.16 (dd, J=7.2, 1.6 Hz, 1H), 4.86 (br, 1H), 3.52 (t, J=6.8 Hz, 2H), 2.98 (t, J=7.6 Hz, 2H), 1.78 (quin, J=7.6 Hz, 2H), 1.49-1.52 (m, 1H), 1.46 (d, J=6.4 Hz, 6H), 1.26-1.41 (br, 21H); MS. m/z 422.3, [M+Na]$^+$.

15-(8-isopropoxyquinolin-2-yl)pentadecan-1-ol (E7)

YD: 36%. $^1$H NMR (400 MHz, CDCl$_3$) δ8.01 (d, J=8.4 Hz, 1H), 7.27-7.36 (m, 3H), 7.10-7.13 (m, 1H), 4.82 (sept, J=4.1 Hz, 1H), 3.61 (t, J=6.8 Hz, 2H), 3.00 (t, J=6.4 Hz, 2H), 1.81 (quin, J=7.6 Hz, 2H), 1.52-1.55 (m, 2H), 1.48 (d, J=2 Hz, 6H), 1.31-1.47 (br, 21H); MS. m/z 436.3, [M+Na]$^+$.

11-(8-isopropoxy-5-methylquinolin-2-yl)undecan-1-ol (E8)

YD: 48%. $^1$H NMR (400 MHz, CDCl$_3$) δ8.09 (d, J=8.4 Hz, 1H), 7.26 (d, J=8.8 Hz, 1H), 7.12 (d, J=8.0 Hz, 1H), 6.97 (t, J=7.6 Hz, 1H), 4.75 (sept, J=6 Hz, 1H), 3.55 (t, J=6.8 Hz, 2H), 3.00 (t, J=7.6 Hz, 2H), 2.51 (s, 3H), 1.81 (t, J=7.2 Hz, 2H), 1.23-1.49 (br, 23H); MS. m/z 394.3, [M+Na]$^+$.

11-(5-fluoro-8-isopropoxyquinolin-2-yl)undecan-1-ol (E9)

YD: 46%. $^1$H NMR (400 MHz, d4-MeOD) δ 8.30 (d, J=8.8 Hz, 1H), 7.44 (d, J=8.4 Hz, 1H), 7.09 (d, J=4.8 Hz, 1H), 4.79 (m, 1H), 3.51 (t, J=6.8 Hz, 2H), 2.97 (t, J=8.0 Hz, 2H), 1.74 (quin, J=7.6 Hz, 2H), 1.45-1.51 (m, 2H), 1.42 (d, J=6.4 Hz, 6H), 1.12-1.39 (br, 15H); MS. m/z 398.2, [M+Na]$^+$.

9-(5-chloro-8-isopropoxyquinolin-2-yl)nonan-1-ol (E10)

YD: 46%. $^1$H NMR (400 MHz, d4-MeOD) δ8.45 (d, J=8.8 Hz, 1H), 7.52 (d, J=8.4 Hz, 1H), 7.49 (d, J=8.4 Hz, 1H), 7.12 (d, J=8.4 Hz, 1H), 4.85 (m, 1H), 3.51 (t, J=6.4 Hz, 2H), 3.01 (t, J=8.0 Hz, 2H), 1.78 (quin, J=7.6 Hz, 2H), 1.49 (quin, J=6.4 Hz, 2H), 1.45 (d, J=6.0 Hz, 6H), 1.30-1.42 (br, 11H); MS. m/z 364.2, [M+Na]$^+$.

11-(5-chloro-8-isopropoxyquinolin-2-yl)undecan-1-ol (E11)

YD: 46%. $^1$H NMR (400 MHz, d4-MeOD) δ8.47 (d, J=8.4 Hz, 1H), 7.53 (d, J=8.4 Hz, 1H), 7.50 (d, J=8.4 Hz, 1H), 7.13

(d, J=8.4 Hz, 1H), 4.89 (m, 1H), 3.52 (t, J=6.4 Hz, 2H), 3.01 (t, J=7.2 Hz, 2H), 1.79 (quin, J=7.6 Hz, 2H), 1.48 (quin, J=6.8 Hz, 2H), 1.41 (d, J=5.6 Hz, 6H), 1.21~1.39 (br, 15H); MS. m/z 414.2, [M+Na]+.

15-(5-chloro-8-isopropoxyquinolin-2-yl)pentadecan-1-ol (E12)

YD: 46%. $^1$H NMR (400 MHz, d4-MeOD+CDCl$_3$) δ 8.46 (d, J=8.8 Hz, 1H), 7.51 (d, J=8.8 Hz, 1H), 7.48 (d, J=8.8 Hz, 1H), 7.11 (d, J=8.4 Hz, 1H), 4.85 (m, 1H), 3.52 (t, J=6.8 Hz, 2H), 3.01 (t, J=8.0 Hz, 2H), 1.79 (quin, J=7.2 Hz, 2H), 1.51 (quin, J=6.8 Hz, 2H), 1.46 (d, J=6.0 Hz, 6H), 1.25-1.39 (m, 23H); MS. m/z 448.3, [M+Na]+.

11-(5-bromo-8-isopropoxyquinolin-2-yl)undecan-1-ol (E13)

YD: 40%. $^1$H NMR (400 MHz, d4-MeOD) δ 8.43 (d, J=8.8 Hz, 1H), 7.69 (d, J=8.8 Hz, 1H), 7.52 (d, J=8.4 Hz, 1H), 7.10 (d, J=7.6 Hz, 1H), 4.86 (br, 1H) 3.52 (t, J=6.8 Hz, 2H) 3.02 (t, J=7.6 Hz, 2H), 1.79 (quin, J=7.2 Hz, 2H), 1.50-1.52 (m, 2H), 1.46 (d, J=6.0 Hz, 6H), 1.28-1.41 (br, 15H); MS. m/z 458.2, [M+Na]+.

11-(5,7-dichloro-8-isopropoxyquinolin-2-yl)undecan-1-ol (E14)

YD: 37%. $^1$H NMR (400 MHz, CDCl$_3$) δ 8.36 (d, J=8.4 Hz, 1H), 7.56 (d, J=3.2 Hz, 1H), 7.35 (d, J=8.4 Hz, 1H), 5.13 (m, 1H), 3.63 (t, J=6.8 Hz, 2H), 3.00 (t, J=7.6 Hz, 2H), 1.86 (quin, J=6.8 Hz, 2H), 1.52-1.59 (m, 4H), 1.27-1.44 (br, 20H); MS. m/z 448.4, [M+Na]+.

Example 4

Preparation of (8-cyclopropylmethoxyquinol-2-yl)alkyl Alcohol Derivatives

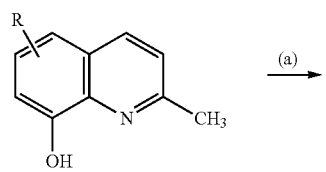

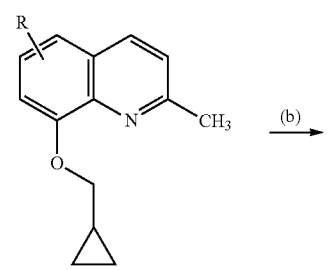

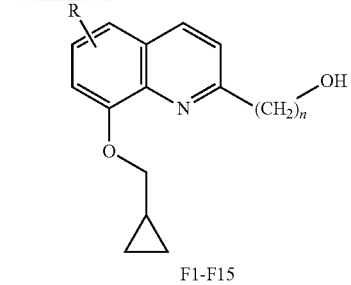

F1-F15

Reagents and Conditions:

(a) Methylenecyclopropyl bromide, K$_2$CO$_3$, DMF, 60° C., 13 h.; (b) 1) LHMDS, THF, 0° C., 1 h.; 2) Br(CH$_2$)$_{n-1}$OH, rt, 12-20 h.

Method:

Methylenecyclopropyl bromide (1.0 g, 6.3 mmol) was added to a stirred solution of 2-methylquinoline (1.0 g, 6.3 mmol) and K$_2$CO$_3$ (2.5 g, 18.1 mmol) in 25 ml DMF at 60° C. for 13 h. The reaction mixture was quenched by H$_2$O (200 ml) and extracted with EtOAc (30 ml×3). The organic layer was concentrated by evaporation in vacuum and the residue purified by flash column chromatography with Hex/EA (8:1 to 6:1) to give 5-chloro-8-(cyclopropylmethoxy)-2-methylquinoline as intermediate. LHMDS (2.2 equiv.) was treated with a stirred solution of intermediate (0.5 g, 2.3 mmol) in THF solution at 0° C. for 1 h. Corresponding Br(CH$_2$)$_{n-1}$OH (1.1-1.2 equiv.) was added to reaction mixture and recover to RT for further 12 to 20 h. The solvent was removed under a reduced pressure. The brown oily residue was purified by flash column chromatography with Hex/EA or DCM/EA and recrystallized by Hex/EA to afford compound F.

9-(8-cyclopropylmethoxy)quinolin-2-yl)nonan-1-ol (F1)

YD: 49%. $^1$H NMR (400 MHz, d4-MeOD) δ 8.15 (d, J=8.4 Hz, 1H), 7.38-7.43 (m, 3H), 7.14 (dd, J=5.6, 3.2 Hz, 1H), 4.06 (d, J=7.2 Hz, 2H), 3.51 (t, J=6.8 Hz, 2H), 3.00 (t, J=8.0 Hz, 2H), 1.77 (quin, J=7.6 Hz, 2H), 1.48-1.52 (m, 3H), 1.32-1.47 (m, 1H), 0.65-0.70 (m, 2H), 0.34-0.45 (m, 2H); MS. m/z 342.2, [M+H]+.

10-(8-cyclopropylmethoxy)quinolin-2-yl)decan-1-ol (F2)

YD: 43%. $^1$H NMR (400 MHz, d4-MeOD) δ 8.16 (d, J=8.4 Hz, 1H), 7.40-7.43 (m, 3H), 7.15 (dd, J=5.6, 3.2 Hz, 1H), 4.07 (d, J=7.2 Hz, 2H), 3.52 (t, J=6.4 Hz, 2H), 3.01 (t, J=8.0 Hz, 2H), 1.80 (quin, J=7.6 Hz, 2H), 1.47-1.53 (m, 3H), 1.31-1.44 (m, 13H), 0.67-0.69 (m, 2H), 0.44-0.46 (m, 2H); MS. m/z 356.2, [M+H]+.

11-(8-(cyclopropylmethoxy)quinolin-2-yl)undecan-1-ol (F3)

YD: 45%. $^1$H NMR (400 MHz, CDCl$_3$) δ 8.02 (d, J=8.4 Hz, 1H), 7.30-7.38 (m, 2H), 7.05 (dd, J=6.4, 2.4 Hz, 1H), 4.11 (d, J=6.8 Hz, 2H), 3.63 (t, J=6.4 Hz, 2H), 3.04 (t, J=8.0 Hz, 2H), 1.83 (quin, J=7.6 Hz, 2H), 1.48-1.59 (m, 3H), 1.26-1.46 (br, 15H), 0.67 (dd, J=13.2, 5.6 Hz, 2H), 0.44 (dd, J=13.2, 5.6 Hz, 2H); MS. m/z 392.2, [M+Na]+.

12-(8-(cyclopropylmethoxy)quinolin-2-yl)dodecan-1-ol (F4)

YD: 36%. $^1$H NMR (400 MHz, CDCl$_3$) δ 8.01 (d, J=8.4 Hz, 1H), 7.29-7.38 (m, 3H), 7.06 (dd, J=6.0, 2.4 Hz, 1H), 4.11 (d, J=6.8 Hz, 1H), 3.63 (t, J=6.4 Hz, 2H), 3.04 (t, J=7.2 Hz, 2H), 1.83 (quin, J=7.6 Hz, 2H), 1.48-1.59 (m, 3H), 1.27-1.47 (br, 17H), 0.67 (dd, J=13.2, 5.6 Hz, 2H), 0.42-0.48 (m, 2H); MS. m/z 384.3, [M+H]$^+$.

13-(8-(cyclopropylmethoxy)quinolin-2-yl)tridecan-1-ol (F5)

YD: 42%. $^1$H NMR (400 MHz, d4-MeOD) δ 8.14 (d, J=8.4 Hz, 1H), 7.38~7.41 (m, 3H), 7.05 (dd, J=5.6, 3.2 Hz, 1H), 4.05 (d, J=6.8 Hz, 2H), 3.52 (t, J=6.4 Hz, 2H), 2.99 (t, J=8.0 Hz, 2H), 1.78 (quin, J=7.6 Hz, 2H), 1.44-1.52 (m, 3H), 1.26-1.40 (m, 19H), 0.67 (dd, J=13.2, 5.6 Hz, 2H), 0.40-0.47 (m, 2H); MS. m/z 420.0, [M+Na]$^+$.

14-(8-(cyclopropylmethoxy)quinolin-2-yl)tetradecan-1-ol (F6)

YD: 37%. $^1$H NMR (400 MHz, d4-MeOD) δ 8.15 (d, J=8.8 Hz, 1H), 7.39-7.42 (m, 3H), 7.13 (dd, J=5.6, 3.2 Hz, 1H), 4.05 (d, J=6.8 Hz, 2H), 3.52 (t, J=6.8 Hz, 2H), 2.99 (t, J=7.6 Hz, 2H), 1.78 (quin, J=7.6 Hz, 2H), 1.44-1.52 (m, 3H), 1.26-1.43 (m, 21H), 0.65-0.69 (m, 2H), 0.42 (dd, J=10.0, 4.8 Hz, 2H); MS. m/z 434.3, [M+Na]$^+$.

15-(8-(cyclopropylmethoxy)quinolin-2-yl)pentadecan-1-ol (F7)

YD: 69%. $^1$H NMR (400 MHz, d4-MeOD+CDCl$_3$) δ 8.13 (dd, J=8.4, 2.0 Hz, 1H), 7.38 (br, 3H), 7.11 (d, J=2.4 Hz, 1H), 4.05 (d, J=6.8 Hz, 2H), 3.52 (t, J=6.8 Hz, 2H), 2.99 (t, J=8.0 Hz, 2H), 1.78 (quin, J=7.2 Hz, 2H), 1.46-1.52 (m, 3H), 1.25-1.44 (m, 23H), 0.63-0.69 (m, 2H), 0.40-0.46 (m, 2H); MS. m/z 426.4, [M+H]$^+$.

11-(8-(cyclopropylmethoxy)-5-methylquinolin-2-yl)undecan-1-ol (F8)

YD: 45%. $^1$H NMR (400 MHz, d4-MeOD) δ 8.31 (d, J=8.8 Hz, 1H), δ 7.44 (d, J=8.8 Hz, 1H), 7.22 (d, J=8.0 Hz, 1H), 7.02 (d, J=8.0 Hz, 1H), 4.02 (d, J=7.2 Hz, 2H), 3.52 (t, J=6.4 Hz, 2H), 3.00 (t, J=8.0 Hz, 2H), 2.57 (s, 3H), 1.79 (quin, J=7.2 Hz, 2H), 1.29-1.52 (m, 18H), 0.65-0.68 (m, 2H), 0.40-0.43 (m, 2H); MS. m/z 406.3, [M+Na]$^+$.

11-(8-(cyclopropylmethoxy)-5-fluoroquinolin-2-yl)undecan-1-ol (F9)

YD: 46%. $^1$H NMR (400 MHz, d4-MeOD) δ 8.36 (d, J=8.8 Hz, 1H), 7.52 (d, J=8.8 Hz, 1H), 7.07-7.15 (m, 2H), 4.05 (d, J=6.8 Hz, 2H), 3.53 (t, J=6.8 Hz, 2H), 3.02 (t, J=7.6 Hz, 2H), 1.79 (quin, J=7.6 Hz, 2H), 1.42-1.49 (m, 3H), 1.22-1.40 (m, 15H), 0.65-0.69 (m, 2H), 0.42 (dd, J=10.4, 4.8 Hz, 2H); MS. m/z 410.2, [M+Na]$^+$.

9-(5-chloro-8-(cyclopropylmethoxy)quinolin-2-yl)nonan-1-ol (F10)

YD: 33%. $^1$H NMR (400 MHz, d4-MeOD) δ 8.48 (d, J=8.8 Hz, 1H), 7.55 (d, J=8.8 Hz, 1H), 7.49 (d, J=8.4 Hz, 1H), 7.11 (d, J=8.4 Hz, 1H), 4.06 (d, J=6.8 Hz, 2H), 3.51 (t, J=6.4 Hz, 2H), 3.03 (t, J=8.0 Hz, 2H), 1.83 (t, J=7.6 Hz, 2H), 1.54-1.69 (m, 3H), 1.27-1.48 (br, 15H), 0.67-0.71 (m, 2H), 0.43-0.46 (m, 2H); MS. m/z 376.2, [M+H]$^+$.

11-(5-chloro-8-(cyclopropylmethoxy)quinolin-2-yl)undecan-1-ol (F11)

YD: 34%. $^1$H NMR (400 MHz, CDCl$_3$) δ 8.41 (d, J=8.8 Hz, 1H), 7.43 (d, J=2.4 Hz, 1H), 7.41 (d, J=2.4 Hz, 1H), 6.97 (d, J=8.4 Hz, 1H), 4.09 (d, J=7.2 Hz, 2H), 3.63 (t, J=6.4 Hz, 2H), 3.05 (t, J=8.0 Hz, 2H), 1.83 (t, J=7.6 Hz, 2H), 1.54-1.69 (m, 3H), 1.27-1.48 (br, 15H), 0.67-0.71 (m, 2H), 0.43-0.46 (m, 2H); MS. m/z 426.2, [M+Na]$^+$.

15-(5-chloro-8-(cyclopropylmethoxy)quinolin-2-yl)pentadecan-1-ol (F12)

YD: 28%. $^1$H NMR (400 MHz, d4-MeOD+CDCl$_3$) δ 8.47 (d, J=8.8 Hz, 1H), 7.54 (d, J=8.8 Hz, 1H), 7.48 (d, J=8.4 Hz, 1H), 7.10 (d, J=8.4 Hz, 1H), 4.06 (d, J=6.8 Hz, 2H), 3.52 (t, J=6.8 Hz, 2H), 3.02 (t, J=7.6 Hz, 2H), 1.79 (quin, J=7.6 Hz, 2H), 1.46-1.52 (m, 2H), 1.25-1.44 (br, 24H), 0.65-0.69 (m, 2H), 0.41-0.43 (m, 2H); MS. m/z 460.3, [M+Na]$^+$.

11-(5-bromo-8-(cyclopropylmethoxy)quinolin-2-yl)undecan-1-ol (F13)

YD: 35%. $^1$H NMR (400 MHz, d4-MeOD) δ 8.42 (d, J=8.8 Hz, 1H), δ 7.67 (J=8.4 Hz, 1H), 7.53 (d, J=8.8 Hz, 1H), 7.06 (d, J=8.4 Hz, 1H), 4.05 (d, J=7.2 Hz, 2H), 3.51 (t, J=6.4 Hz, 2H), 3.02 (t, J=8.0 Hz, 2H), 1.77 (quin, 7.6 Hz, 2H), 1.46-1.52 (m, 3H), 1.28-1.44 (m, 15H), 0.65-0.70 (m, 2H), 0.42-0.45 (m, 2H); MS. m/z 470.2, [M+Na]$^+$.

11-(5,7-dichloro-8-(cyclopropylmethoxy)quinolin-2-yl)undecan-1-ol (F14)

YD: 53%. $^1$H NMR (400 MHz, d4-MeOD) δ 8.47 (d, J=8.8 Hz, 1H), δ 7.67 (s, 1H), 7.53 (d, J=8.8 Hz, 1H), 7.06 (d, J=8.4 Hz, 1H), 4.23 (d, J=7.2 Hz, 2H), 3.53 (t, J=6.4 Hz, 2H), 3.02 (t, J=7.6 Hz, 2H), 1.86 (quin, J=7.2 Hz, 2H), 1.48-1.53 (m, 2H), 1.29-1.38 (m, 16H), 0.62 (dd, J=12.8, 5.2 Hz, 2H), 0.31 (dd, J=10.8, 5.2 Hz, 2H); MS. m/z 460.2, [M+Na]$^+$.

Example 5

Preparation of (5,7-dichloro-8-hydroxyquinol-2-yl)alkyl alcohol

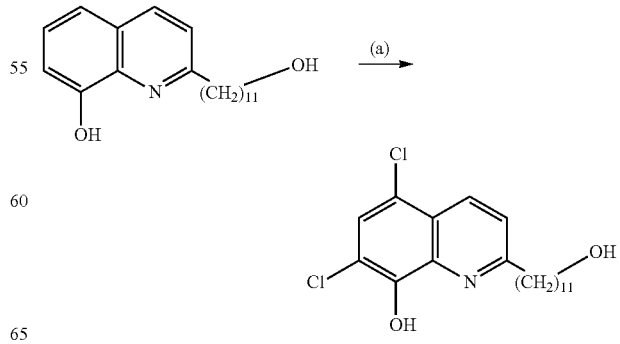

Reagents and Conditions:
(a) NCS, CHCl$_3$, rt, 48 h.
Method:
N-chlorosuccinimide (0.3 g, 2.25 mmol) was added to a stirred solution of compounds B in CHCl$_3$ (20 ml) for 48 h. The reaction mixture was poured into crushed ice and extracted with CH$_2$Cl$_2$ (20 ml×2). The extract was purified by column chromatography with Hex/EA (3:1) and recrystallized to give compound G1 (0.18 g, 49%).

5,7-dichloro-2-(11-hydroxyundecyl)quinolin-8-(G1)

YD: 49%. $^1$H NMR (400 MHz, CDCl$_3$) δ8.38 (d, J=8.8 Hz, 1H), 7.51 (s, 1H), 7.42 (d, J=8.8 Hz, 1H), 3.63 (t, J=6.8 Hz, 2H), 3.00 (t, J=7.6 Hz, 2H), 1.82 (quin, J=7.2 Hz, 2H), 1.56 (quin, J=7.6 Hz, 2H), 1.27-1.38 (br, 15H); MS. m/z 382.0, [M+H]$^+$.

Example 6

Preparation of (5-chloro-8-methoxyquinol-2-yl)alkyl alcohol or alkylacetate

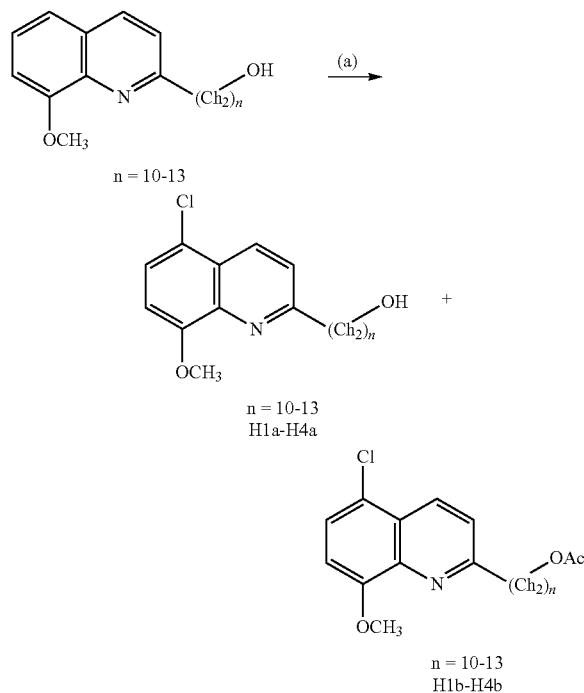

Reagents and Conditions:
(a) HCl, ICl$_3$, glacial HOAc, H$_2$O, 6 h, rt.
Method:
To a various long chain substituted (8-methoxyquinolin-2-yl)-ol (1.0 eq.) was added conc. HCl (0.5 mL/mmol) at RT and the reddish yellow mixture was stirred for 5 minutes. To this mixture was added dropwise a solution of ICl$_3$ (1.5 eq.) in conc. HCl (2 mL). The yellow gummy mixture was stirred at RT for 6 h. Water was added to it and partitioned with EA. Organic layer was washed with brine, drying on anhydrous MgSO$_4$ and filtered followed by solvent removal, yielded oily residue purified by flash column chromatography using CHCl$_3$ to yield H1 to H5.

10-(5-Chloro-8-methoxyquinolin-2-yl)decan-1-ol (H1a) and acetic acid 10-(5-chloro-8-methoxyquinolin-2-yl)decyl ester (H1b)

YD: 61% and 10%. H1a: $^1$H NMR (200 MHz, CDCl$_3$) δ8.41 (d, J=8.68 Hz, 1H), 7.42 (dd, J=8 Hz, J=2 Hz, 2H), 6.91 (d, J=8 Hz, 1H), 4.03 (s, 3H), 3.59 (t, J=6 Hz, 2H), 3.59 (t, J=4 Hz, 2H), 1.73 (m, 2H), 1.48 (m, 2H), 1.25 (br, 12H); HRMS (EI): Calcd for C$_{20}$H$_{28}$ClNO$_2$: 349.1803. Found: 349.1781. H1b: $^1$H NMR (400 MHz, CDCl$_3$) δ8.41 (d, J=8 Hz, 1H), 7.42 (dd, J=8 Hz, J=4 Hz, 2H), 6.92 (d, J=8 Hz, 1H), 4.06 (t, J=8 Hz, 2H), 4.02 (s, 3H), 3.03 (t, J=8 Hz, 2H), 2.02 (s, 3H), 1.79 (m, 2H), 1.59 (m, 2H), 1.40 (m, 2H), 1.23 (br, 12H); HRMS (FAB, M+H): Calcd for C$_{22}$H$_{31}$ClNO$_3$ 392.1992. Found 392.1983.

11-(5-Chloro-8-methoxyquinolin-2-yl)undecan-1-ol (H2a) and acetic acid 11-(5-chloro-8-methoxyquinolin-2-yl)undecyl ester (H2b)

YD: 60% and 12%. H2a: $^1$H NMR (400 MHz, CDCl$_3$) δ8.43 (d, J=8.72 Hz, 1H), 7.44 (dd, J=13.5 Hz, J=5.3 Hz, 2H), 6.94 (d, J=8.3 Hz, 1H), 4.05 (s, 3H), 3.62 (t, J=6.6 Hz, 2H), 3.07 (t, J=5.2 Hz, 2H), 1.80 (m, 2H), 1.54 (m, 2H), 1.39 (m, 2H), 1.26 (br, 12H); HRMS (EI): Calcd for C$_{21}$H$_{30}$ClNO$_2$ 363.1960. Found 363.1941. H2b: $^1$H NMR (400 MHz, CDCl$_3$) δ8.41 (d, J=8.6 Hz, 1H), 7.42 (dd, J=8.3 Hz, J=3.8 Hz, 2H), 6.91 (d, J=8.4 Hz, 1H), 4.06 (t, J=7.8 Hz, 2H), 4.02 (s, 3H), 3.02 (t, J=7.8 Hz, 2H), 2.01 (s, 3H), 1.78 (m, 2H), 1.58 (m, 2H), 1.39 (m, 2H), 1.22 (br, 12H); HRMS (EI): Calcd for C$_{23}$H$_{32}$ClNO$_3$ 405.2065. Found 405.2044.

12-(5-Chloro-8-methoxyquinolin-2-yl)dodecan-1-ol (H3a) and acetic acid 12-(5-chloro-8-methoxyquinolin-2-yl)dodecyl ester (H3b)

YD: 57% and 27%. H3a: $^1$H NMR (400 MHz, CDCl$_3$) δ8.46 (d, J=8.6 Hz, 1H), 7.44 (dd, J=8.3 Hz, J=6.9 Hz, 2H), 6.94 (d, J=8.4 Hz, 1H), 4.04 (s, 3H), 3.59 (t, J=6.6 Hz, 2H), 3.11 (t, J=7.8 Hz, 2H), 1.78 (m, 2H), 1.50 (m, 2H), 1.40 (m, 2H), 1.23 (br, 14H); HRMS (EI): Calcd for C$_{22}$H$_{32}$ClNO$_2$ 377.2116. Found 377.2106. H3b: $^1$H NMR (200 MHz, CDCl$_3$) δ8.38 (d, J=8.7 Hz, 1H), 7.40 (d, J=8.6 Hz, 2H), 6.88 (d, J=8.4 Hz, 1H), 4.03 (t, J=7.8 Hz, 214), 4.01 (s, 3H), 3.02 (t, J=7.8 Hz, 2H), 1.99 (s, 3H), 1.76 (m, 2H), 1.59 (m, 2H), 1.20 (br, 16H); HRMS (FAB, M+H): Calcd for C$_{24}$H$_{35}$ClNO$_3$ 420.2305. Found 420.2310.

13-(5-Chloro-8-methoxyquinolin-2-yl)tridecan-1-ol (H4a) and acetic acid 13-(5-chloro-8-methoxyquinolin-2-yl)tridecyl ester (H4b)

YD: 64% and 14%. H4a: $^1$H NMR (400 MHz, CDCl$_3$) δ8.46 (d, J=8.6 Hz, 1H), 7.45 (dd, J=8.3 Hz, J=6.9 Hz, 2H), 6.94 (d, J=8.4 Hz, 1H), 4.04 (s, 3H), 3.59 (t, J=6.6 Hz, 2H), 3.11 (t, J=7.8 Hz, 2H), 1.78 (m, 2H), 1.50 (m, 2H), 1.40 (m, 2H), 1.23 (br, 16H); HRMS (EI): Calcd for C$_{23}$H$_{34}$ClNO$_2$ 391.2273. Found 391.2249, H4b: $^1$H NMR (400 MHz, CDCl$_3$) δ 8.38 (d, J=8.6 Hz, 1H), 7.40 (dd, J=8.5 Hz, J=5.8 Hz, 2H), 6.89 (d, J=8.4 Hz, 1H), 4.01 (t, J=9.6 Hz, 2H), 4.00 (s, 3H), 3.00 (t, J=7.9 Hz, 2H), 1.99 (s, 3H), 1.75 (m, 2H), 1.58 (m, 2H), 1.38 (m, 2H), 1.22 (br, 16H); HRMS (FAB, M+H): Calcd for C$_{25}$H$_{37}$ClNO$_3$ 434.2462. Found 434.2459.

Example 7

Preparation of (8-hydroxyquinol-4-yl) or (8-alkoxyquinol-4-yl)alkyl alcohols

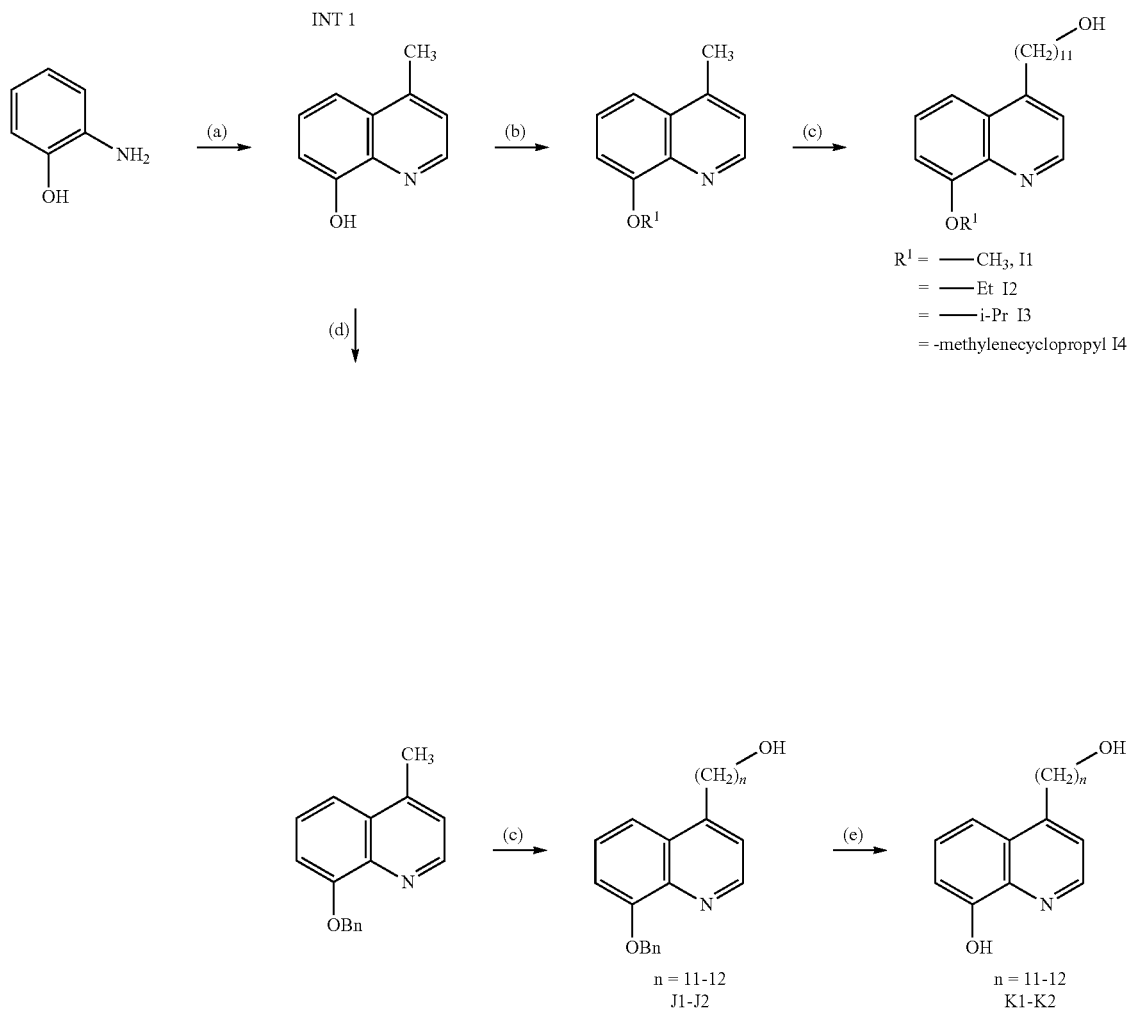

Reagents and Conditions:

(a) methyl vinyl ketone, HCl, reflux, (b) MeI, $K_2CO_3$, acetone, rt, 8 h; EtI or 2-bromopropane or methylenecyclopropyl bromide, $K_2CO_3$, DMF, 60° C., (c) 1) LHMDS, THF, 0° C., 1 h.; 2) $Br(CH_2)_{n-1}OH$, rt, (d) BnBr, KOH, EtOH, reflux, (e) $H_2$, Pd/C, MeOH, rt, 24 h.

Method:

The intermediate INT 1 was synthesized through ring closure from 2-aminophenol reacted with methyl vinyl ketone. INT 1 was reacted with various alkyl halides to afford 8-alkoxy-4-methylquinoline derivatives as intermediates. Corresponding $Br(CH_2)_{n-1}OH$ was reacted with intermediates to synthesize series of compounds J and I. The protective group J was removed by hydrogenation (method illustrated in example 1) to obtain compound K.

11-(8-methoxyquinolin-4-yl)undecan-1-ol (I1)

YD: 34%. $^1$H NMR (400 MHz, $CDCl_3$) δ8.80 (dd, J=4.4, 0.6 Hz, 1H), 7.59 (dd, J=8.4, 0.8 Hz, 1H), 7.44-7.49 (m, 1H), 7.03 (d, J=7.6 Hz, 1H), 4.08 (s, 3H), 3.63 (t, J=6.8 Hz, 2H), 3.03 (t, J=7.6 Hz, 2H), 1.74 (quin, J=7.6 Hz, 2H), 1.55 (quin, J=7.2 Hz, 2H), 1.23-1.45 (br, 15H), MS. m/z 329.9, $[M+H]^+$.

11-(8-ethoxyquinolin-4-yl)undecan-1-ol (I2)

YD: 42%. H NMR (400 MHz, d4-MeOD) δ8.66 (d, J=8.4 Hz, 1H), 7.64 (d, J=8.4 Hz, 1H), 7.51 (t, J=8.0 Hz, 1H), 7.37 (d, J=8.4 Hz, 1H), 7.15 (d, J=7.6 Hz, 1H), 4.27 (q, J=6.8 Hz, 2H), 3.52 (t, J=6.8 Hz, 2H), 3.08 (d, J=7.6 Hz, 2H), 1.75 (quin, J=7.6 Hz, 2H), 1.50-1.57 (m, 5H), 1.21-1.49 (br, 15H); MS. m/z 366.2, $[M+Na]^+$.

11-(8-isopropoxyquinolin-4-yl)undecan-1-ol (I3)

YD: 48%. $^1$H NMR (400 MHz, d4-MeOD) δ 8.65 (d, J=8.4 Hz, 1H), 7.63 (d, J=7.6 Hz, 1H), 7.51 (d, J=8.0 Hz, 1H), 7.35 (d, J=4.4 Hz, 1H), 7.17 (d, J=8.0 Hz, 1H), 4.84 (br, 1H), 3.52 (t, J=6.4 Hz, 2H), 3.07 (d, J=7.6 Hz, 2H), 1.74 (br, 2H), 1.43-1.50 (br, 9H), 1.29-1.34 (br, 14H); MS. m/z 380.3, $[M+Na]^+$.

11-(8-cyclopropylmethoxy)quinolin-4-yl)undecan-1-ol (I4)

YD: 53%. $^1$H NMR (400 MHz, d4-MeOD) δ 8.66 (d, J=8.4 Hz, 1H), 7.63 (d, J=8.4 Hz, 1H), 7.49 (t, J=8.4 Hz, 1H), 7.36 (d, J=4.8 Hz, 1H), 7.13 (d, J=7.6 Hz, 1H), 4.03 (d, J=6.8 Hz, 1H), 3.52 (t, J=6.8 Hz, 2H), 3.06 (d, J=7.6 Hz, 2H), 1.69-1.75 (m, 2H), 1.28-1.52 (br, 18H), 0.65-0.68 (m, 2H), 0.42-0.43 (m, 2H); MS. m/z 392.2 [M+Na]$^+$.

11-(8-(benzyloxy)quinolin-4-yl)undecan-1-ol (J1)

YD: 46%. $^1$H NMR (400 MHz, d4-MeOD) δ 8.66 (d, J=8.4 Hz, 1H), 7.64 (d, J=8.4 Hz, 1H), 7.52 (d, J=7.2 Hz, 2H), 7.45 (t, J=8.0 Hz, 1H), 7.30-7.38 (m, 3H), 7.26-7.28 (m, 1H), 7.17 (d, J=7.6 Hz, 1H), 5.37 (s, 2H), 3.52 (t, J=6.4 Hz, 2H), 3.06 (t, J=8 Hz, 2H), 1.73 (q, J=7.6 Hz, 2H), 1.50 (t, J=7.2 Hz, 2H), 1.28-1.48 (m, 15H); MS. m/z 428.3, [M+Na]$^+$.

12-(8-(benzyloxy)quinolin-4-yl)dodecan-1-ol (J2)

YD: 46%. $^1$H NMR (400 MHz, d4-MeOD) δ 8.67 (d, J=4.4 Hz, 1H), 7.65 (d, J=8.4 Hz, 1H), 7.52 (d, J=7.2 Hz, 2H), 7.45 (t, J=8.0 Hz, 1H), 7.30-7.39 (m, 3H), 7.27-7.30 (m, 1H), 7.18 (d, J=8.0 Hz, 1H), 5.38 (s, 2H), 3.52 (t, J=6.4 Hz, 2H), 3.08 (t, J=7.6 Hz, 2H), 1.74 (q, J=7.6 Hz, 2H), 1.49 (t, J=7.2 Hz, 2H), 1.23-1.45 (m, 17H); MS. m/z 442.3, [M+Na]$^+$.

4-(11-hydroxyundecyl)quinolin-8-ol (K1)

YD: 84%. $^1$H NMR (400 MHz, d4-MeOD) δ 8.63 (d, J=4.4 Hz, 1H), 7.51 (d, J=8.4 Hz, 1H), 7.40 (t, J=8.0 Hz, 1H), 7.28 (d, J=4.0 Hz, 1H), 7.06 (d, J=7.6 Hz, 1H), 3.51 (t, J=6.8 Hz, 2H), 3.02 (t, J=8.0 Hz, 2H), 1.71 (t, J=7.6 Hz, 2H), 1.50 (quin, J=6.8 Hz, 2H), 1.12-1.31 (br, 15H); MS. m/z 316.2, [M+H]$^+$.

4-(12-hydroxydodecyl)quinolin-8-ol (K2)

YD: 86%. $^1$H NMR (400 MHz, CDCl$_3$) δ8.52 (d, J=4.4 Hz, 1H), 7.36 (dd, J=8.4, 0.8 Hz, 1H), 7.31 (d, J=7.6 Hz, 1H), 7.13 (d, J=4.4 Hz, 1H), 6.99 (dd, J=7.6, 1.2 Hz, 1H), 3.43 (t, J=6.8 Hz, 2H), 2.89 (t, J=7.6 Hz, 2H), 1.61 (quin, J=7.6 Hz, 2H), 1.40 (quin, J=6.8 Hz, 2H), 1.12-1.31 (br, 17H); MS. m/z 352.2, [M+Na]$^+$.

Example 8

Preparation of (8-trifluoromethoxyquinol-2-yl)alkyl alcohols

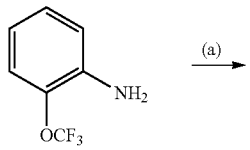

(a)

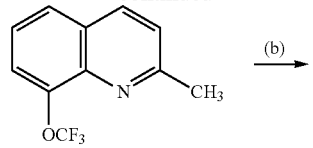

(b)

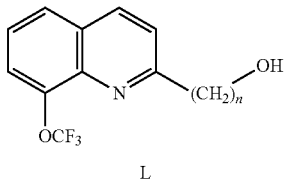

L

Method:

The intermediate was synthesized through ring closure from 2-trifluoromethoxyaniline reacted with crotonaldehyde. Intermediate was reacted with corresponding Br(CH$_2$)$_{n-1}$OH (as illustrated above) to synthesize series compounds L.

9-(8-trifluoromethoxy)quinolin-2-yl)nonan-1-ol (L1)

YD: 41%. $^1$H NMR (400 MHz, CDCl$_3$) δ8.06 (dd, J=8.4, 1.2 Hz, 1H), 7.70 (d, J=8.4 Hz, 1H), 7.56 (d, J=7.6 Hz, 1H), 7.43 (d, J=8.0 Hz, 1H), 7.34 (dd, J=8.4, 1.2 Hz, 1H), 3.61 (t, J=6.4 Hz, 2H), 3.01 (t, J=6.4 Hz, 2H), 1.81-1.85 (br, 2H), 1.53-1.56 (br, 2H), 1.21-1.35 (m, 15H); MS. m/z 355.9, [M+H]$^+$.

11-(8-trifluoromethoxy)quinolin-2-yl)undecan-1-ol (L2)

YD: 41%. $^1$H NMR (400 MHz, d4-MeOD) δ8.26 (t, J=8.0 Hz, 1H), 7.86 (d, J=7.6 Hz, 1H), 7.64 (t, J=7.2 Hz, 1H), 7.47-7.56 (m, 2H), 3.51 (t, J=6.8 Hz, 2H) 2.99 (t, J=6.4 Hz, 2H), 1.79 (quin, J=6.8 Hz, 2H), 1.50 (quin, J=6.8 Hz, 2H), 1.21-1.35 (m, 15H); MS. m/z 406.2, [M+Na]$^+$.

14-(8-(trifluoromethoxy)quinolin-2-yl)tetradecan-1-ol (L3)

YD: 37%. $^1$H NMR (400 MHz, d4-MeOD) δ 8.27 (d, J=8.4 Hz, 1H), 7.87 (d, J=8.0 Hz, 1H), 7.65 (t, J=7.2 Hz, 1H), 7.49-7.56 (m, 2H), 3.52 (t, J=6.8 Hz, 2H), 3.01 (t, J=7.6 Hz, 2H), 1.82 (quin, J=7.2 Hz, 2H), 1.51 (quin, J=6.8 Hz, 2H), 1.27-1.37 (m, 21H); MS. m/z 448.2, [M+Na]$^+$.

15-(8-(trifluoromethoxy)quinolin-2-yl)pentadecan-1-ol (L4)

YD: 32%. $^1$H NMR (400 MHz, d4-MeOD+CDCl$_3$) δ8.21 (d, J=8.4 Hz, 1H), 7.81 (d, J=8.0 Hz, 1H), 7.61 (d, J=7.6 Hz, 1H), 7.51 (d, J=8.0 Hz, 1H), 7.46 (t, J=8.4 Hz, 1H), 3.52 (t, J=6.8 Hz, 2H), 2.99 (t, J=7.6 Hz, 2H), 1.80 (quin, J=7.6 Hz, 2H), 1.50 (quin, J=7.2 Hz, 2H), 1.15-1.41 (br, 23H); MS. m/z 462.2, [M+Na]$^+$.

Example 9

Preparation of 2-N-substituted alcohol-8-hydroxyquinoline

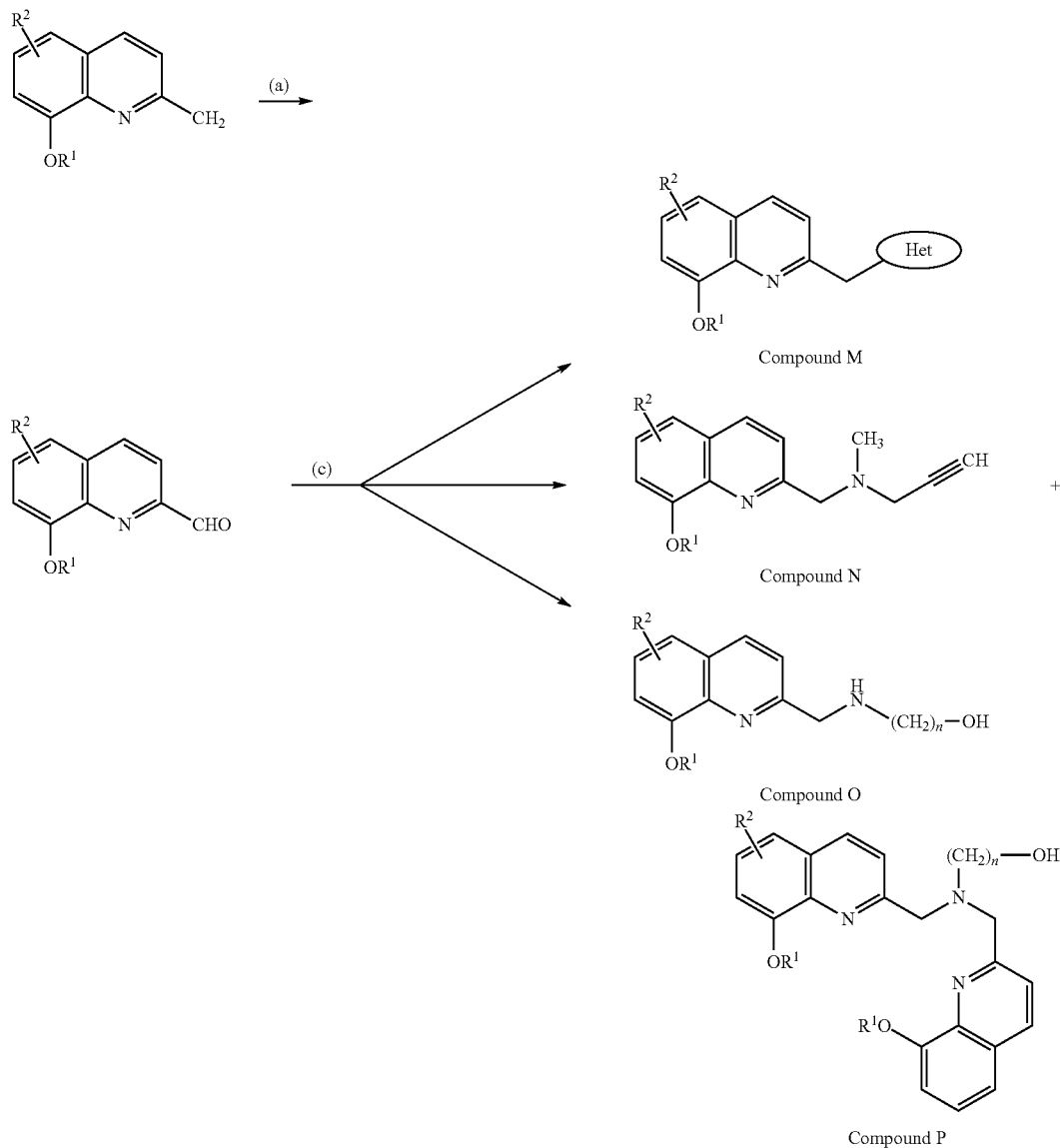

Reagents and Conditions:

(a) SeO$_2$, dioxane, 50 to 80° C.; (b) N-methylpropagylamine or 2-(piperazin-1-yl)ethanol or NH$_2$(CH$_2$)n–1OH, NaBH(OAc)$_3$, 1,2-dichloroethane, rt.

Method:

A solution of 8-hydroxy-2-methylquinoline (6.0 g, 37.7 mmol) in dioxane (15 ml) was added to a stirred solution of SeO$_2$ (6.3 g, 56.8 mmol) in dioxane (80 ml) dropwise at 50° C. and the mixture was heated up to 80° C. for further 20 h. The resulting mixture was filtered. The filtrate was concentrated and the residue purified by column chromatography with Hex/EA=(15:1 to 10:1) to give 8-hydroxyquinoline-2-carboxaldehyde (2.45 g, 38%) derivatives as intermediates. Intermediate was converted into N-substituted compounds by reductive amination with aminoalcohol, aminoalkyne or other heterocycles to give series of compounds. 8-alkoxy-2-methyl quinoline were oxidized to give 8-alkoxyquinoline-2-carboxaldehyde derivatives and followed by the same method to give compounds M to O.

2-((4-(2-hydroxyethyl)piperazin-1-yl)methyl)quinolin-8-ol (M1)

YD: 76%. $^1$H NMR (400 MHz, CDCl$_3$) δ8.02 (d, J=8.4 Hz, 1H), 7.43 (d, J=8.4 Hz, 1H), 7.34 (t, J=8.0 Hz, 1H), 7.22 (d, J=7.6 Hz, 1H), 7.10 (d, J=6.8 Hz, 1H), 3.73 (s, 2H), 3.61 (t, J=6.8 Hz, 2H), 2.51 (t, J=5.6 Hz, 10H); HRMS (ESI): Calcd for [M+Na]$^+$: 310.1526. Found: 310.1527.

2-(4-((5-chloro-8-methoxyquinolin-2-yl)methyl)piperazin-1-yl)ethanol (M2)

YD: 76%. $^1$H NMR (400 MHz, CDCl$_3$) δ8.23 (d, J=8.8 Hz, 1H), 7.59 (d, J=8.8 Hz, 1H), 7.21 (d, J=8.4 Hz, 1H), 6.68 (d, J=8.8 Hz, 1H), 3.81 (s, 3H), 3.72 (s, 2H), 3.44 (t, J=4.8 Hz, 2H), 2.35-2.38 (m, 10H); MS. m/z 336.1, [M+H]$^+$.

2-(4-((5-chloro-8-ethoxyquinolin-2-yl)methyl)piperazin-1-yl)ethanol (M3)

YD: 53%. $^1$H NMR (400 MHz, CDCl$_3$) δ8.36 (d, J=8.8 Hz, 1H), 7.68 (d, J=8.4 Hz, 1H), 7.34 (d, J=8.4 Hz, 1H), 6.83 (d, J=8.4 Hz, 1H), 4.18 (q, J=6.8 Hz, 3H), 3.84 (s, 2H), 3.54 (t, J=5.2 Hz, 2H), 2.45-2.50 (br, 10H), 1.49 (t, J=6.8 Hz, 3H); MS. m/z 350.1, [M+H]$^+$.

2-(4-((5-chloro-8-isopropoxyquinolin-2-yl)methyl)piperazin-1-yl)ethanol (M4)

YD: 61%. $^1$H NMR (400 MHz, d4-MeOD) δ8.52 (d, J=8.8 Hz, 1H), 7.81 (d, J=8.8 Hz, 1H), 7.53 (d, J=8.4 Hz, 1H), 7.14 (d, J=8.4 Hz, 1H), 4.87 (m, 1H), 3.89 (s, 2H), 3.67 (t, J=6.0 Hz, 2H), 2.54-2.62 (br, 10H), 1.45 (t, J=6.0 Hz, 6H); MS. m/z 364.1, [M+H]$^+$.

2-(4-((5-chloro-8-(cyclopropylmethoxy)quinolin-2-yl)methyl)piperazin-1-yl)ethane (M5)

YD: 76%. $^1$H NMR (400 MHz, d4-MeOD) δ8.40 (d, J=8.4 Hz, 1H), 7.71 (d, J=8.8 Hz, 1H), 7.42 (d, J=8.4 Hz, 1H), 6.99 (d, J=8.4 Hz, 1H), 3.97 (d, J=6.8 Hz, 2H), 3.84 (s, 2H), 3.65 (t, J=6.0 Hz, 2H), 3.44 (t, J=4.8 Hz, 2H), 2.56 (br, 8H), 2.51 (t, J=4.8 Hz, 2H), 1.37-1.43 (m, 1H), 0.62-0.66 (m, 2H), 0.37-0.40 (m, 2H); MS. m/z 376.2, [M+H]$^+$.

2-(4-((5,7-dichloro-8-methoxyquinolin-2-yl)methyl)piperazin-1-yl)ethanol (M6)

YD: 39%. $^1$H NMR (400 MHz, d4-MeOD) δ 8.53 (d, J=8.8 Hz, 1H), 7.80 (d, J=8.8 Hz, 1H), 7.70 (s, 1H), 4.11 (s, 3H), 3.89 (s, 2H), 3.67 (t, J=6.0 Hz, 2H), 2.63 (br, 8H), 2.55 (t, J=6.0 Hz, 2H), 1.93 (s, 1H); MS. m/z 370.1, [M+H]$^+$.

2-(4-((5,7-dichloro-8-(cyclopropylmethoxy)quinolin-2-yl)methyl)piperazin-1-yl)ethanol (M7)

YD: 82%. $^1$H NMR (400 MHz, CDCl$_3$) δ8.43 (d, J=8.8 Hz, 1H) δ7.71 (d, J=8.8 Hz, 1H), 7.58 (s, 1H), 4.22 (d, J=7.2 Hz, 2H), 3.88 (s, 2H) 3.61 (t, J=6.4 Hz, 2H), 2.56 (t, J=5.2 Hz, 1.0H), 1.41-1.44 (m, 1H), 0.57-0.62 (m, 2H), 0.33-0.37 (m, 2H); MS. m/z 410.1, [M+Na]$^+$.

2-((methyl(prop-2-ynyl)amino)methyl)quinolin-8-ol (N1)

YD: 49%. $^1$H NMR (400 MHz, CDCl$_3$) δ8.08 (d, J=8.4 Hz, 1H), 7.55 (d, J=8.4 Hz, 1H), 7.40 (t, J=8.0 Hz, 1H), 7.28 (d, J=8.0 Hz, 1H), 7.15 (d, J=7.6 Hz, 1H), 3.90 (s, 2H), 3.41 (d, J=2.0 Hz, 2H), 2.39 (s, 3H), 2.31 (d, J=2.0 Hz, 1H); MS. m/z 249.1, [M+H]$^+$.

5-chloro-2-((methyl(prop-2-ynyl)amino)methyl)quinolin-8-ol (N2)

YD: 38%. $^1$H NMR (400 MHz, CDCl$_3$) δ8.47 (d, J=8.4 Hz, 1H), 7.71 (d, J=8.8 Hz, 1H), 7.4 (d, J=8.0 Hz, 1H), 7.08 (d, J=8.4 Hz, 1H), 3.93 (s, 2H), 3.42 (d, J=2.0 Hz, 2H), 2.40 (s, 3H), 2.31 (t, J=2.0 Hz, 1H); MS. m/z 261.0, [M+H]$^+$.

N-((5-chloro-8-methoxyquinolin-2-yl)methyl)-N-methylprop-2-yn-1-amine (N3)

YD: 52%. $^1$H NMR (400 MHz, CDCl$_3$) δ8.48 (d, J=8.8 Hz, 1H), 7.80 (d, J=8.8 Hz, 1H), 7.46 (d, J=8.4 Hz, 1H), 6.93 (d, J=8.4 Hz, 1H), 4.05 (s, 3H), 4.00 (s, 2H), 3.42 (d, J=2.0 Hz, 2H), 2.37 (s, 3H), 2.27 (t, J=2.0 Hz, 1H), MS. m/z 297.0, [M+Na]$^+$.

N-((5-chloro-8-ethoxyquinolin-2-yl)methyl)-N-methyprop-2-yn-1-amine (N4)

YD: 64%. $^1$H NMR (400 MHz, CDCl$_3$) δ8.48 (d, J=8.8 Hz, 1H), 7.79 (d, J=8.8 Hz, 1H), 7.46 (d, J=8.8 Hz, 1H), 6.96 (d, J=8.4 Hz, 1H), 4.32 (t, J=6.8 Hz, 2H), 4.01 (s, 2H), 3.45 (d, J=2.0 Hz, 2H), 2.41 (s, 3H), 2.28 (t, J=2.0 Hz, 1H), 1.59 (t, J=6.8 Hz, 3H); MS. m/z 289.1, [M+H]$^+$.

N-((5-chloro-8-isopropoxyquinolin-2-yl)methyl)-N-methylprop-2-yn-1-amine (N5)

YD: 76%. $^1$H NMR (400 MHz, CDCl$_3$) δ8.47 (d, J=8.8 Hz, 1H), 7.73 (d, J=8.8 Hz, 1H), 7.46 (d, J=8.0 Hz, 1H), 7.03 (d, J=8.4 Hz, 1H), 4.80 (m, 1H), 3.99 (s, 2H), 3.44 (d, J=2.4 Hz, 2H), 2.41 (s, 3H), 2.28 (t, J=2.4 Hz, 1H), 1.48 (d, J=6.4 Hz, 6H); MS. m/z 303.1, [M+H]$^+$.

N-((5-chloro-8-(cyclopropylmethoxy)quinolin-2-yl)methyl)-N-methylprop-2-yn-1-amine (N6)

YD: 58%. $^1$H NMR (400 MHz, CDCl$_3$) δ8.48 (d, J=8.4 Hz, 1H), 7.77 (d, J=8.8 Hz, 1H), 7.45 (d, J=8.4 Hz, 1H), 6.98 (d, J=8.4 Hz, 1H), 4.09 (d, J=7.2 Hz, 2H), 4.01 (s, 2H), 3.45 (d, J=2.0 Hz, 2H), 2.41 (s, 3H), 2.28 (t, J=2.0 Hz, 1H), 1.42~1.50 (m, 1H), 0.65-0.70 (m, 2H), 0.42-0.45 (m, 2H); MS. m/z 337.1, [M+Na]$^+$.

N-((5,7-dichloro-8-methoxyquinolin-2-yl)methyl)-N-methylprop-2-yn-1-amine (N7)

YD: 58%. $^1$H NMR (400 MHz, CDCl$_3$) δ8.47 (d, J=8.8 Hz, 1H), 7.74 (d, J=8.8 Hz, 1H), 7.60 (s, 1H), 4.20 (s, 3H), 3.99 (s, 2H), 3.43 (d, J=2.0 Hz, 2H), 2.41 (s, 3H), 2.29 (t, J=2.0 Hz, 1H); MS. m/z 309.0, [M+H]$^+$.

N-((5,7-dichloro-8-(cyclopropylmethoxy)quinolin-2-yl)methyl-N-methylprop-2-yn-1-amine (N8)

YD: 76%. $^1$H NMR (400 MHz, CDCl$_3$) δ8.45 (d, J=8.8 Hz, 1H), 7.71 (d, J=8.8 Hz, 1H), 7.59 (s, 1H), 4.25 (d, J=7.6 Hz, 2H), 3.95 (s, 2H), 3.40 (d, J=2.0 Hz, 2H), 2.40 (s, 3H), 2.28 (t, J=2.0 Hz, 1H), 1.41-1.45 (m, 1H), 0.57-0.62 (m, 2H), 0.36 (dd, J=10.0, 4.8 Hz, 2H); MS. m/z 371.0, [M+Na]$^+$.

8-((5-chloro-8-methoxyquinolin-2-yl)methylamino)octan-1-ol (O1)

YD: 44%. $^1$H NMR (400 MHz, d4-MeOD) δ8.55 (d, J=8.8 Hz, 1H), 7.69 (d, J=8.8 Hz, 1H), 7.58 (d, J=8.4 Hz, 1H) 7.16 (d, J=8.4 Hz, 1H), 4.07 (s, 5H), 3.50 (t, J=6.8 Hz, 2H), 2.63 (t, J=7.2 Hz, 2H), 1.56 (quin, J=7.2 Hz, 2H), 1.50 (quin, J=6.8 Hz, 2H), 1.29-1.32 (br, 10H); MS. m/z 351.2, [M+H]$^+$.

8-((5-chloro-8-ethoxyquinolin-2-yl)methylamino)octan-1-ol (O2)

YD: 41%. $^1$H NMR (400 MHz, d4-MeOD) δ8.51 (d, J=8.8 Hz, 1H), 7.66 (d, J=8.4 Hz, 1H), 7.53 (d, J=8.4 Hz, 1H), 7.12 (d, J=8.4 Hz, 1H), 4.29 (q, J=6.8 Hz, 2H), 4.0 (s, 2H), 3.5.1 (t, J=6.8 Hz, 2H), 2.64 (t, J=7.2 Hz, 2H), 1.47-1.58 (m, 7H), 1.31 (br, 9H); MS. m/z 365.2, [M+H]$^+$.

8-((5-chloro-8-isopropoxyquinolin-2-yl)methylamino)octan-1-ol (O3)

YD: 31%. $^1$H NMR (400 MHz, d4-MeOD) δ8.55 (d, J=8.8 Hz, 1H), 7.66 (d, J=8.8 Hz, 1H), 7.56 (d, J=8.4 Hz, 1H), 7.19 (d, J=8.4 Hz, 1H), 4.89 (m, 1H), 4.15 (s, 2H), 3.52 (t, J=6.4 Hz, 2H), 2.71 (t, J=7.2 Hz, 2H), 1.59 (quin, J=6.8 Hz, 2H) 1.46-1.50 (m, 8H), 1.33 (br, 9H); MS. m/z 379.2, [M+H]$^+$.

8-((5-chloro-8-(cyclopropylmethoxy)quinolin-2-yl)methylamino)octan-1-ol (O4)

YD: 29%. $^1$H NMR (400 MHz, d4-MeOD) δ8.54 (d, J=8.4 Hz, 1H), 7.67 (d, J=8.8 Hz, 1H), 7.54 (d, J=8.4 Hz, 1H), 7.15 (d, J=8.4 Hz, 1H), 4.09 (s+d, J=6.8 Hz, 4H), 3.51 (t, J=6.8 Hz, 2H), 2.67 (t, J=7.2 Hz, 2H), 1.59 (quin, J=7.2 Hz, 2H), 1.43-1.51 (m, 3H), 1.29-1.42 (br, 10H), 0.66-0.89 (m, 2H), 0.44 (dd, J=10.4, 4.8 Hz, 2H); MS. m/z 391.2, [M+H]$^+$.

8-((5,7-dichloro-8-methoxyquinolin-2-yl)methylamino)octan-1-ol (O5)

YD: 37%. $^1$H NMR (400 MHz, d4-MeOD) δ8.54 (d, J=8.8 Hz, 1H), 7.71 (s, 1H), 7.65 (d, J=8.8 Hz, 1H), 4.14 (s, 3H), 4.12 (s, 2H), 3.52 (t, J=6.8 Hz, 2H), 2.70 (t, J=7.2 Hz, 2H), 1.60 (quin, J=6.8 Hz, 2H), 1.50 (m, 2H), 1.33 (br, 9H); MS. m/z 385.1, [M+H]$^+$.

8-((5,7-dichloro-8-(cyclopropylmethoxy)quinolin-2-yl)methylamino)octan-1-ol (O6)

YD: 56%. $^1$H NMR (400 MHz, d4-MeOD) δ8.51 (d, J=8.4 Hz, 1H), 7.69 (s, 1H), 7.61 (d, J=8.8 Hz, 1H), 4.22 (d, J=7.2 Hz, 2H), 4.10 (s, 2H), 3.52 (t, J=6.8 Hz, 2H), 2.68 (t, J=7.2 Hz, 2H), 1.59 (quin, 7.2 Hz, 2H), 1.51 (quin, J=6.8 Hz, 2H), 1.28-1.42 (br, 11H), 0.55-0.60 (m, 2H), 0.30-0.33 (m, 2H); MS. m/z 425.2, [M+H]$^+$.

6-(bis(8-methoxyquinolin-2-yl)methyl)amino)hexan-1-ol (P1)

$^1$H NMR (400 MHz, d4-MeOD) δ8.18 (d, J=8.4 Hz, 2H), 7.80 (d, J=8.4 Hz, 2H), 7.44 (t, J=8.0 Hz, 2H), 7.38 (d, J=8.0 Hz, 2H), 7.13 (d, J=7.2 Hz, 2H), 4.02 (s, 6H), 3.99 (s, 4H), 3.40 (t, J=6.8 Hz, 2H), 2.59 (t, J=6.8 Hz, 2H), 1.56 (quin, J=6.8 Hz, 2H), 1.41 (quin, J=6.8 Hz, 2H), 1.27 (quin, J=7.6 Hz, 2H), 1.18 (quin, J=6.8 Hz, 2H); MS. m/z 482.3, [M+Na]$^+$.

Figure 1B:
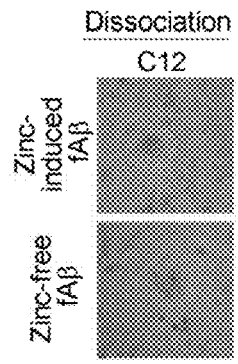
Figure 2:
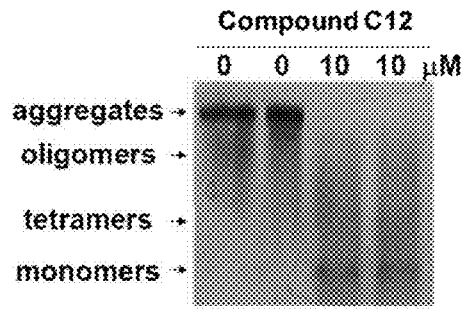
FIG. 2 shows compound C12 inhibiting polymerization of Aβ in the absence of zinc ions.
Figure 3A:
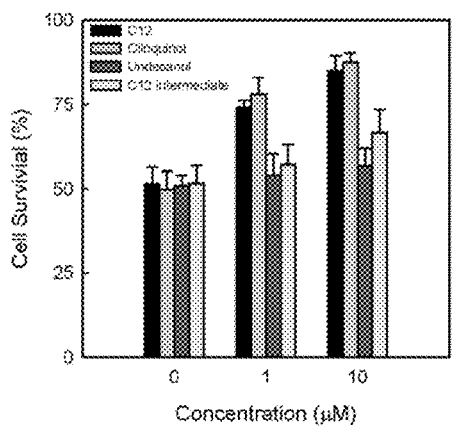
FIGS. 3A-B show compound C12 acting as a neuroprotective agent targeting fAβ.
Figure 3B:
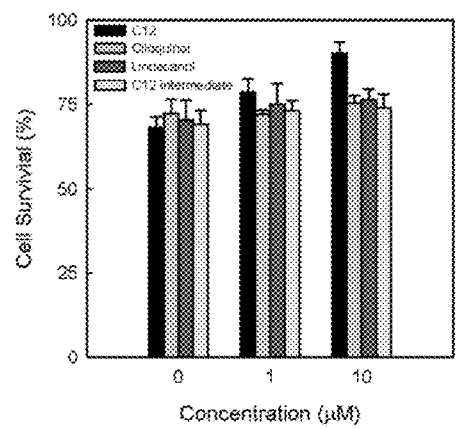
Figure 4:
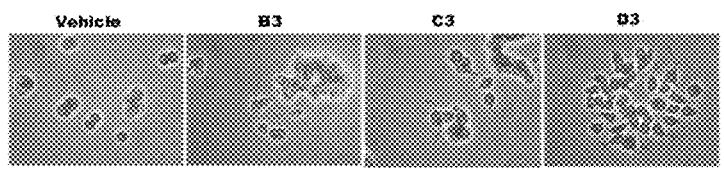
FIG. 4 shows quinoline derivatives-induced neurite outgrowth.
Figure 5:
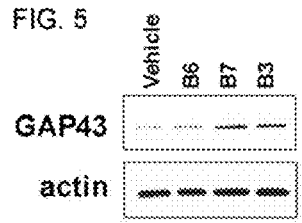
FIG. 5 shows quinoline derivatives increased expression of GAP43 (a marker for neurite outgrowth).
Figure 6:
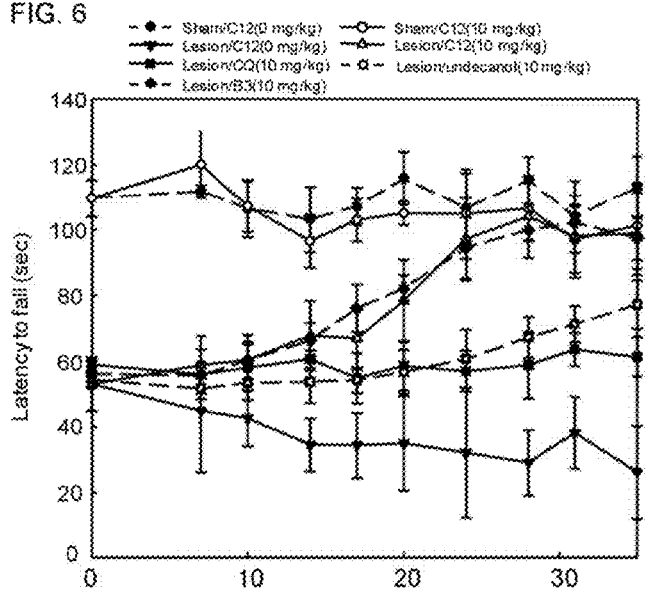
FIG. 6 shows the results of rotarod test.
Figure 8:
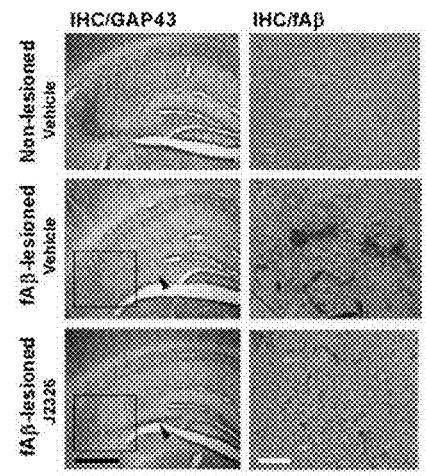
FIG. 8 shows an increase in GAP43 level and decrease in fAβ level in memory-deficit fAβ-lesioned mice after compound C12 treatment.
Figure 7A:
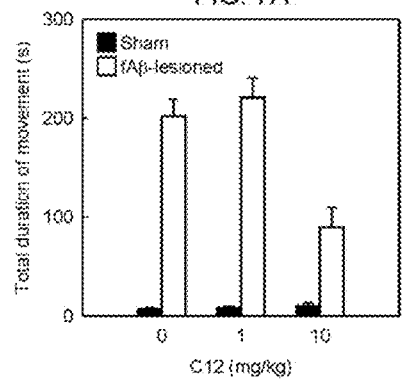
FIGS. 7A-D show the results of Morris water maze test.
Figure 7B:
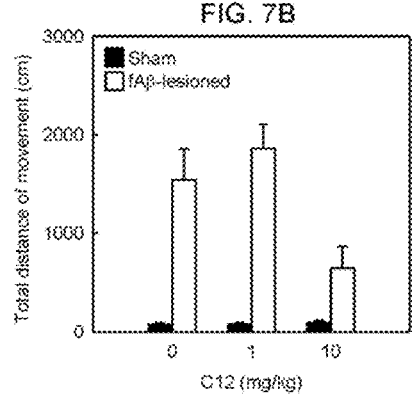
Figure 7C:
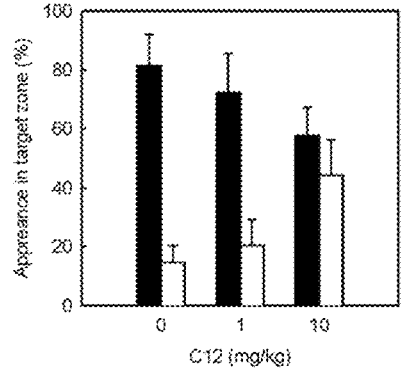
Figure 7D:
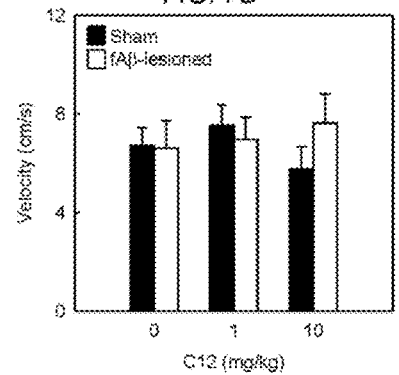

FIG. 1A shows C12 inhibited Aβ aggregation in the presence or absence of zinc ions using a microscopy analysis after Congo red staining. FIG. 1B and FIG. 2 show that C12 dissolved preformed Aβ aggregates. FIGS. 3A-B show that compounds C12, CQ and C12 intermediate protected neuron cells from zinc-induced fAβ. Only compound C12 was effective toward zinc-free aggregates (FIG. 3B). FIG. 4 shows induction of neurite outgrowth triggered by compounds B3, C3, and D3, respectively, on undifferentiated PC12 cells. FIG. 5 shows quinoline derivatives increased expression of GAP43. FIG. 6 shows compound C12 and B3 improved performance of learning in fAβ-induced memory-deficit mice. C12 and B3 (10 mg/kg) increased riding time of fAβ-lesioned mice in a rotarod test. FIGS. 7A-D show compound C12 improved learning of memory-deficit fAβ-lesioned mice in the Morris water maze test. Mice were assessed for the total duration of movement (FIG. 7A) and total duration of distance (FIG. 7B) to climb onto the hidden platform; and also quantified the appearance to target zone (FIG. 7C) indicating the relative time (compared to total time in swimming) to entry into a zone around the hidden platform; and for average swimming velocity (FIG. 7D) to discriminate enhanced memory from enhanced motor activity. FIG. 8 shows an increase in GAP43 level and decrease in fAβ level in memory-deficit fAβ-lesioned mice by compound C12.

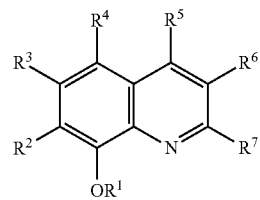

(I)

| Cpd No. Chemical Name | Structure | Substituents |
|---|---|---|
| Example 1 | | |
| A1<br>9-(8-(benzyloxy)quinolin-2-yl)nonan-1-ol | | $R^1$ = benzyl<br>$R^2, R^3, R^4, R^5$, and $R^6$ = hydrogen<br>$R^7$ = —$(CH_2)_9OH$ |
| A2<br>10-(8-(benzyloxy)quinolin-2-yl)decan-1-ol | | $R^1$ = benzyl<br>$R^2, R^3, R^4, R^5$, and $R^6$ = hydrogen<br>$R^7$ = —$(CH_2)_{10}OH$ |
| A3<br>11-(8-(benzyloxy)quinolin-2-yl)undecan-1-ol | | $R^1$ = benzyl<br>$R^2, R^3, R^4, R^5$, and $R^6$ = hydrogen<br>$R^7$ = —$(CH_2)_{11}OH$ |
| A4<br>12-(8-(benzyloxy)quinolin-2-yl)dodecan-1-ol | | $R^1$ = benzyl<br>$R^2, R^3, R^4, R^5$, and $R^6$ = hydrogen<br>$R^7$ = —$(CH_2)_{12}OH$ |
| A5<br>13-(8-(benzyloxy)quinolin-2-yl)tridecan-1-ol | | $R^1$ = benzyl<br>$R^2, R^3, R^4, R^5$, and $R^6$ = hydrogen<br>$R^7$ = —$(CH_2)_{13}OH$ |

-continued

| Cpd No. Chemical Name | Structure | Substituents |
|---|---|---|
| A6 14-(8-(benzyloxy)quinolin-2-yl)tetradecan-1-ol | | $R^1$ = benzyl $R^2, R^3, R^4, R^5$, and $R^6$ = hydrogen $R^7$ =—$(CH_2)_{14}OH$ |
| A7 15-(8-(benzyloxy)quinolin-2-yl)pentadecan-1-ol | | $R^1$ = benzyl $R^2, R^3, R^4, R^5$, and $R^6$ = hydrogen $R^7$ =—$(CH_2)_{15}OH$ |
| A8 11-(8-(benzyloxy)-5-methylquinolin-2-yl)undecan-1-ol | | $R^1$ = benzyl $R^2, R^3, R^5$, and $R^6$ = hydrogen $R^4$ = $CH_3$ $R^7$ =—$(CH_2)_{11}OH$ |
| A9 11-(8-(benzyloxy)-6-methylquinolin-2-yl)undecan-1-ol | | $R^1$ = benzyl $R^2, R^4, R^5$, and $R^6$ = hydrogen $R^3$ = $CH_3$ $R^7$ =—$(CH_2)_{11}OH$ |
| A10 11-(8-(benzyloxy)-5-fluoroquinolin-2-yl)undecan-1-ol | | $R^1$ = benzyl $R^2, R^3, R^5$, and $R^6$ = hydrogen $R^4$ = F $R^7$ =—$(CH_2)_{11}OH$ |

-continued

| Cpd No. Chemical Name | Structure | Substituents |
|---|---|---|
| A11 11-(8-(benzyloxy)-5-chloroquinolin-2-yl)undecan-1-ol | 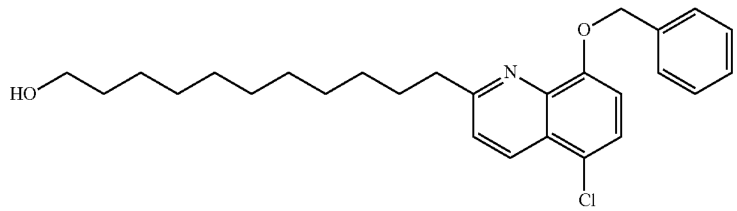 [SMILES: OCCCCCCCCCCCc1ccc2c(F)ccc(OCc3ccccc3)c2n1] | $R^1$ = benzyl $R^2, R^3, R^5, R^6$ = hydrogen $R^4$ = Cl $R^7$ = —$(CH_2)_{11}OH$ |
| B1 2-(9-hydroxynonyl)quinolin-8-ol | 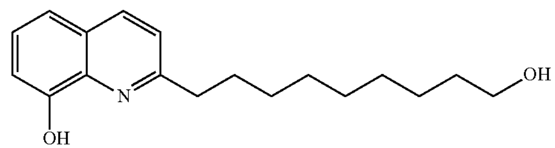 [SMILES: OCCCCCCCCCc1ccc2cccc(O)c2n1] | $R^1$ = hydrogen $R^2, R^3, R^4, R^5, R^6$ = hydrogen $R^7$ = —$(CH_2)_9OH$ |
| B2 2-(10-hydroxydecyl)quinolin-8-ol | 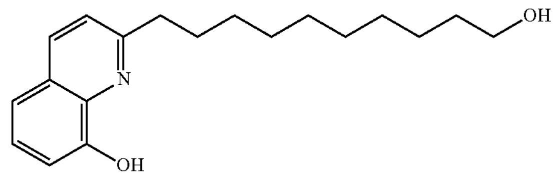 [SMILES: OCCCCCCCCCCc1ccc2cccc(O)c2n1] | $R^1$ = hydrogen $R^2, R^3, R^4, R^5, R^6$ = hydrogen $R^7$ = —$(CH_2)_{10}OH$ |
| B3 2-(11-hydroxyundecyl)quinolin-8-ol | 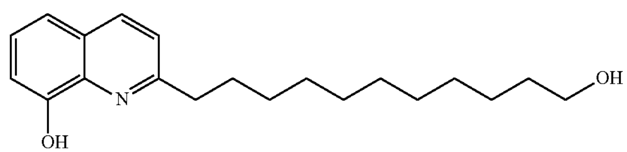 [SMILES: OCCCCCCCCCCCc1ccc2cccc(O)c2n1] | $R^1$ = hydrogen $R^2, R^3, R^4, R^5, R^6$ = hydrogen $R^7$ = —$(CH_2)_{11}OH$ |
| B4 2-(12-hydroxydodecyl)quinolin-8-ol | 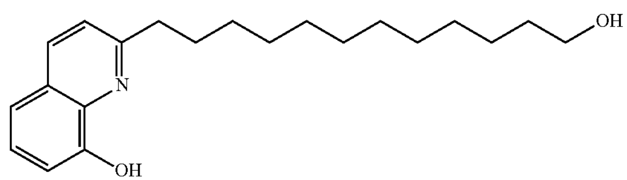 [SMILES: OCCCCCCCCCCCCc1ccc2cccc(O)c2n1] | $R^1$ = hydrogen $R^2, R^3, R^4, R^5, R^6$ = hydrogen $R^7$ = —$(CH_2)_{12}OH$ |

-continued

| Cpd No. Chemical Name | Structure | Substituents |
|---|---|---|
| B5 2-(13-hydroxytridecyl)quinolin-8-ol | 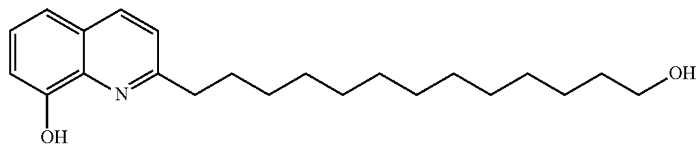 [SMILES: OCCCCCCCCCCCCCc1ccc2cccc(O)c2n1] | $R^1$ = hydrogen $R^2, R^3, R^4, R^5$, and $R^6$ = hydrogen $R^7$ = —$(CH_2)_{13}OH$ |
| B6 2-(14-hydroxytetradecyl)quinolin-8-ol | 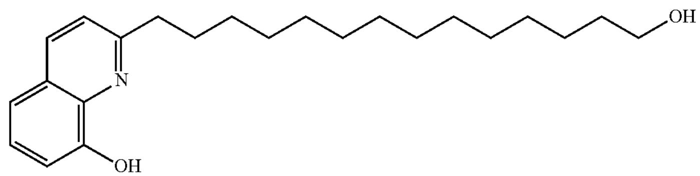 [SMILES: OCCCCCCCCCCCCCCc1ccc2cccc(O)c2n1] | $R^1$ = hydrogen $R^2, R^3, R^4, R^5$, and $R^6$ = hydrogen $R^7$ = —$(CH_2)_{14}OH$ |
| B7 2-(15-hydroxypentadecyl)quinolin-8-ol | 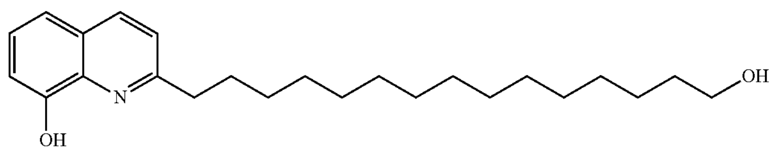 [SMILES: OCCCCCCCCCCCCCCCc1ccc2cccc(O)c2n1] | $R^1$ = hydrogen $R^2, R^3, R^4, R^5$, and $R^6$ = hydrogen $R^7$ = —$(CH_2)_{15}OH$ |
| B8 2-(11-hydroxyundecyl)-5-methyl-quinolin-8-ol | 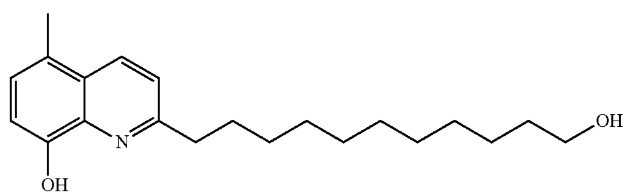 [SMILES: Cc1ccc(O)c2nc(CCCCCCCCCCCO)ccc12] | $R^1$ = hydrogen $R^2, R^3, R^5$, and $R^6$ = hydrogen $R^7$ = —$(CH_2)_{11}OH$ |
| B9 2-(11-hydroxyundecyl)-6-methyl-quinolin-8-ol | 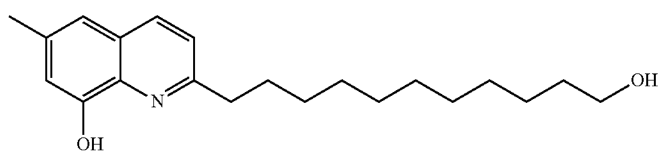 [SMILES: Cc1cc(O)c2nc(CCCCCCCCCCCO)ccc2c1] | $R^1$ = hydrogen $R^2, R^4, R^5$, and $R^6$ = $CH_3$ $R^7$ = —$(CH_2)_{11}OH$ |

-continued

| Cpd No. Chemical Name | Structure | Substituents |
|---|---|---|
| B10 5-chloro-2-(11-hydroxyundecyl)quinolin-8-ol | | $R^1$ = hydrogen $R^2, R^3, R^5$ = hydrogen $R^6$ = hydrogen $R^4$ = Cl $R^7$ = —$(CH_2)_{11}OH$ |

Example 2

| Cpd No. Chemical Name | Structure | Substituents |
|---|---|---|
| C1 9-(8-methoxyquinolin-2-yl)nonan-1-ol | 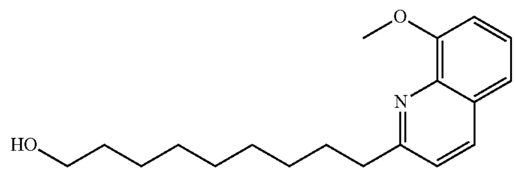 [SMILES: COc1cccc2ccc(CCCCCCCCCO)nc12] | $R^1$ = $CH_3$, $R^2, R^3, R^4, R^5$, and $R^6$ = hydrogen $R^7$ = —$(CH_2)_9OH$ |
| C2 10-(8-methoxyquinolin-2-yl)decan-1-ol | 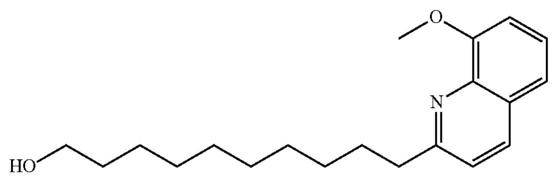 [SMILES: COc1cccc2ccc(CCCCCCCCCCO)nc12] | $R^1$ = $CH_3$, $R^2, R^3, R^4, R^5$, and $R^6$ = hydrogen $R^7$ = —$(CH_2)_{10}OH$ |
| C3 11-(8-methoxyquinolin-2-yl)undecan-1-ol | 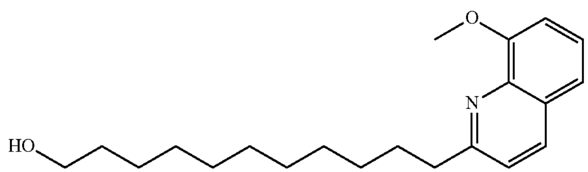 [SMILES: COc1cccc2ccc(CCCCCCCCCCCO)nc12] | $R^1$ = $CH_3$, $R^2, R^3, R^4, R^5$, and $R^6$ = hydrogen $R^7$ = —$(CH_2)_{11}OH$ |
| C4 12-(8-methoxyquinolin-2-yl)dodecan-1-ol | 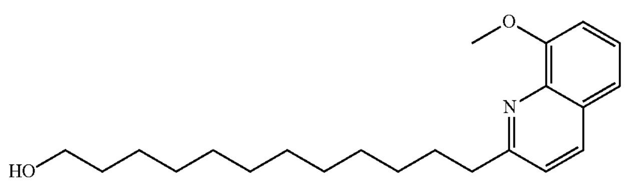 [SMILES: COc1cccc2ccc(CCCCCCCCCCCCO)nc12] | $R^1$ = $CH_3$, $R^2, R^3, R^4, R^5$, and $R^6$ = hydrogen $R^7$ = —$(CH_2)_{12}OH$ |

-continued

| Cpd No. Chemical Name | Structure | Substituents |
|---|---|---|
| C5 13-(8-methoxyquinolin-2-yl)tridecan-1-ol | 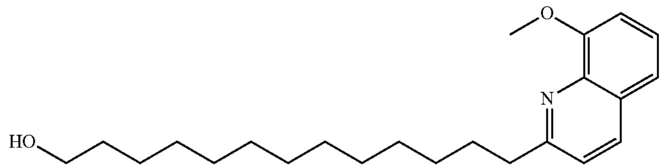 [SMILES: COc1cccc2ccc(CCCCCCCCCCCCCO)nc12] | $R^1 = CH_3$, $R^2, R^3, R^4, R^5$, and $R^6$ = hydrogen $R^7 = -(CH_2)_{13}OH$ |
| C6 14-(8-methoxyquinolin-2-yl)tetradecan-1-ol | 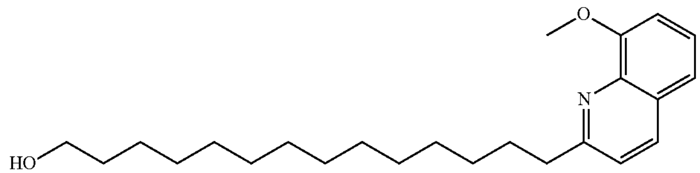 [SMILES: COc1cccc2ccc(CCCCCCCCCCCCCCO)nc12] | $R^1 = CH_3$, $R^2, R^3, R^4, R^5$, and $R^6$ = hydrogen $R^7 = -(CH_2)_{14}OH$ |
| C7 15-(8-methoxyquinolin-2-yl)pentadecan-1-ol | 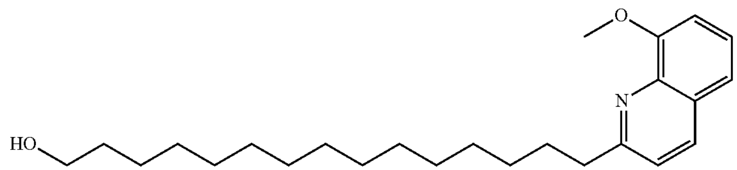 [SMILES: COc1cccc2ccc(CCCCCCCCCCCCCCCO)nc12] | $R^1 = CH_3$, $R^2, R^3, R^4, R^5$, and $R^6$ = hydrogen $R^7 = -(CH_2)_{15}OH$ |
| C8 11-(8-methoxy-5-methylquinolin-2-yl)undecan-1-ol | 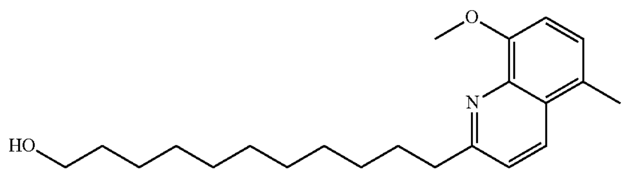 [SMILES: COc1ccc(C)c2ccc(CCCCCCCCCCCO)nc12] | $R^1 = CH_3$, $R^2, R^3, R^5$, and $R^6$ = hydrogen $R^4 = CH_3$ $R^7 = -(CH_2)_{11}OH$ |
| C9 11-(5-fluoro-8-methoxyquinolin-2-yl)undecan-1-ol | 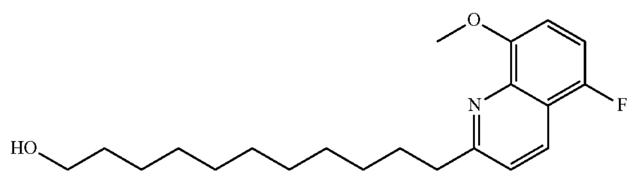 [SMILES: COc1ccc(F)c2ccc(CCCCCCCCCCCO)nc12] | $R^1 = CH_3$, $R^2, R^3, R^5$, and $R^6$ = hydrogen $R^4 = F$ $R^7 = -(CH_2)_{11}OH$ |

-continued

| Cpd No. Chemical Name | Structure | Substituents |
|---|---|---|
| C10 12-(5-fluoro-8-methoxyquinolin-2-yl)dodecan-1-ol | 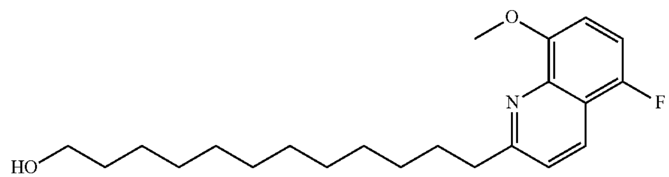 [SMILES: COc1ccc(F)c2ccc(CCCCCCCCCCCCO)nc12] | $R^1 = CH_3$<br>$R^2, R^3, R^5,$ and $R^6 =$ hydrogen<br>$R^4 = F$<br>$R^7 = -(CH_2)_{12}OH$ |
| C11 9-(5-fluoro-8-methoxyquinolin-2-yl)nonan-1-ol | 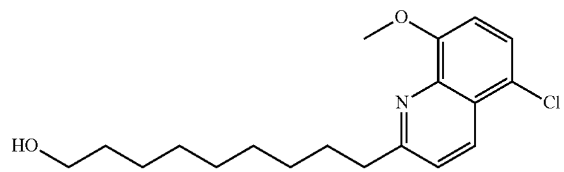 [SMILES: COc1ccc(Cl)c2ccc(CCCCCCCCCO)nc12] | $R^1 = CH_3$<br>$R^2, R^3, R^5,$ and $R^6 =$ hydrogen<br>$R^4 = Cl$<br>$R^7 = -(CH_2)_9OH$ |
| C12 11-(5-chloro-8-methoxyquinolin-2-yl)undecan-1-ol | 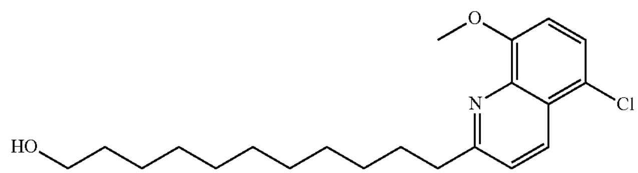 [SMILES: COc1ccc(Cl)c2ccc(CCCCCCCCCCCO)nc12] | $R^1 = CH_3$<br>$R^2, R^3, R^5,$ and $R^6 =$ hydrogen<br>$R^4 = Cl$<br>$R^7 = -(CH_2)_{11}OH$ |
| C13 15-(5-chloro-8-methoxyquinolin-2-yl)pentadecan-1-ol | 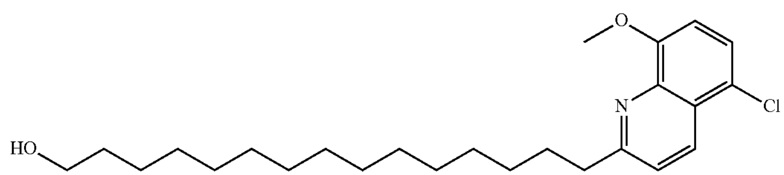 [SMILES: COc1ccc(Cl)c2ccc(CCCCCCCCCCCCCCCO)nc12] | $R^1 = CH_3$<br>$R^2, R^3, R^5,$ and $R^6 =$ hydrogen<br>$R^4 = Cl$<br>$R^7 = -(CH_2)_{15}OH$ |
| C14 11-(5-bromo-8-methoxyquinolin-2-yl)undecan-1-ol | 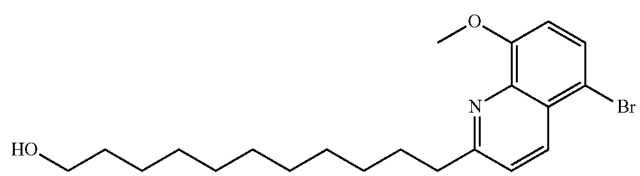 [SMILES: COc1ccc(Br)c2ccc(CCCCCCCCCCCO)nc12] | $R^1 = CH_3$<br>$R^2, R^3, R^5,$ and $R^6 =$ hydrogen<br>$R^4 = Br$<br>$R^7 = -(CH_2)_{11}OH$ |

-continued

| Cpd No. Chemical Name | Structure | Substituents |
|---|---|---|
| C15 11-(8-methoxy-5-(trifluoromethyl)quinolin-2-yl)undecan-1-ol | 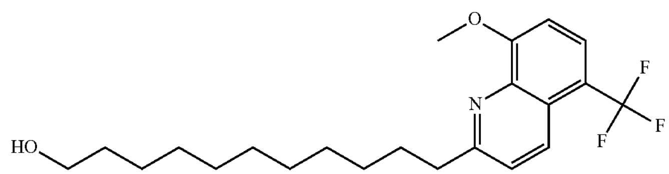 [SMILES: COc1ccc(C(F)(F)F)c2ccc(CCCCCCCCCCCO)nc12] | $R^1 = CH_3$ $R^2, R^3, R^5, $ and $R^6 = $ hydrogen $R^4 = CF_3$ $R^7 = -(CH_2)_{11}OH$ |
| C16 11-(5,8-dimethoxyquinolin-2-yl)undecan-1-ol | 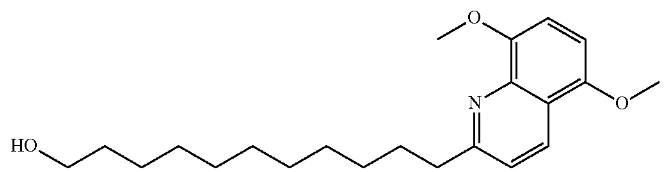 [SMILES: COc1ccc(OC)c2nc(CCCCCCCCCCCO)ccc12] | $R^1 = CH_3$ $R^2, R^3, R^5, $ and $R^6 = $ hydrogen $R^4 = OCH_3$ $R^7 = -(CH_2)_{11}OH$ |
| C17 11-(8-methoxy-6-methylquinolin-2-yl)undecan-1-ol | 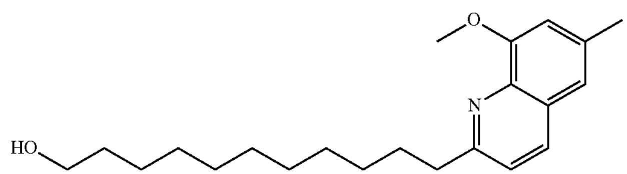 [SMILES: COc1cc(C)cc2ccc(CCCCCCCCCCCO)nc12] | $R^1 = CH_3$ $R^2, R^4, R^5, $ and $R^6 = $ hydrogen $R^3 = CH_3$ $R^7 = -(CH_2)_{11}OH$ |
| C18 11-(6-fluoro-8-methoxyquinolin-2-yl)undecan-1-ol | 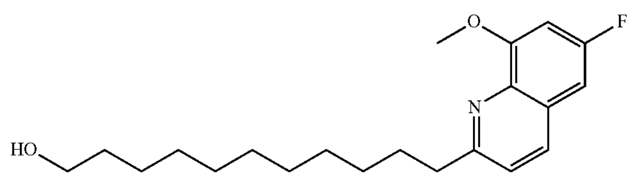 [SMILES: COc1cc(F)cc2ccc(CCCCCCCCCCCO)nc12] | $R^1 = CH_3$ $R^2, R^4, R^5, $ and $R^6 = $ hydrogen $R^3 = F$ $R^7 = -(CH_2)_{11}OH$ |
| C19 11-(6-chloro-8-methoxyquinolin-2-yl)undecan-1-ol | 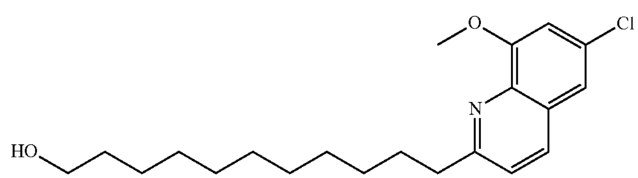 [SMILES: COc1cc(Cl)cc2ccc(CCCCCCCCCCCO)nc12] | $R^1 = CH_3$ $R^2, R^4, R^5, $ and $R^6 = $ hydrogen $R^3 = Cl$ $R^7 = -(CH_2)_{11}OH$ |

-continued

| Cpd No. Chemical Name | Structure | Substituents |
|---|---|---|
| C20 11-(7-fluoro-8-methoxyquinolin-2-yl)undecan-1-ol | | $R^1 = CH_3$ $R^2 = F$ $R^3, R^4, R^5,$ and $R^6 =$ hydrogen $R^7 = -(CH_2)_{11}OH$ |
| C21 11-(7-chloro-8-methoxyquinolin-2-yl)undecan-1-ol | | $R^1 = CH_3$ $R^2 = Cl$ $R^3, R^4, R^5,$ and $R^6 =$ hydrogen $R^7 = -(CH_2)_{11}OH$ |
| C22 11-(5-chloro-6,8-dimethoxyquinolin-2-yl)undecan-1-ol | | $R^1 = CH_3$ $R^2, R^5, R^6 =$ hydrogen $R^3 = OCH_3$ $R^4 = Cl$ $R^7 = -(CH_2)_{11}OH$ |
| C23 11-(6-chloro-5,8-dimethoxyquinolin-2-yl)undecan-1-ol | | $R^1 = CH_3$ $R^2, R^5, R^6 =$ hydrogen $R^3 = Cl$ $R^4 = OCH_3$ $R^7 = -(CH_2)_{11}OH$ |

-continued

| Cpd No. Chemical Name | Structure | Substituents |
|---|---|---|
| C24 11-(5,7-dichloro-8-methoxyquinolin-2-yl)undecan-1-ol | | $R^1 = CH_3$, $R^2, R^4 = Cl$ $R^3, R^5, R^6 =$ hydrogen $R^7 = -(CH_2)_{11}OH$ |
| Example 3 | | |
| D1 9-(8-ethoxyquinolin-2-yl)nonan-1-ol | | $R^1 = CH_2CH_3$, $R^2, R^3, R^4, R^5,$ and $R^6 =$ hydrogen $R^7 = -(CH_2)_9OH$ |
| D2 10-(8-ethoxyquinolin-2-yl)decan-1-ol | | $R^1 = CH_2CH_3$, $R^2, R^3, R^4, R^5,$ and $R^6 =$ hydrogen $R^7 = -(CH_2)_{10}OH$ |
| D3 11-(8-ethoxyquinolin-2-yl)undecan-1-ol | | $R^1 = CH_2CH_3$, $R^2, R^3, R^4, R^5,$ and $R^6 =$ hydrogen $R^7 = -(CH_2)_{11}OH$ |

-continued

| Cpd No. Chemical Name | Structure | Substituents |
|---|---|---|
| D4 12-(8-ethoxyquinolin-2-yl)dodecan-1-ol | 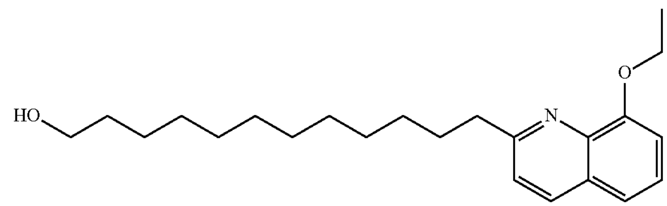 [SMILES: CCOc1cccc2ccc(CCCCCCCCCCCCO)nc12] | $R^1 = CH_2CH_3$ $R^2, R^3, R^4, R^5,$ and $R^6 =$ hydrogen $R^7 = -(CH_2)_{12}OH$ |
| D5 13-(8-ethoxyquinolin-2-yl)tridecan-1-ol | 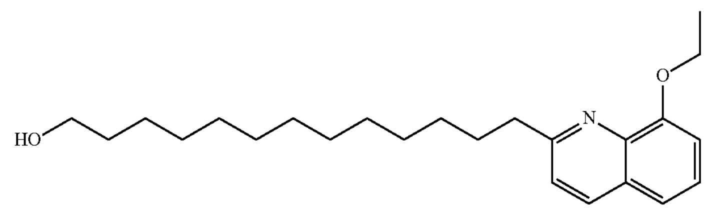 [SMILES: CCOc1cccc2ccc(CCCCCCCCCCCCCO)nc12] | $R^1 = CH_2CH_3$ $R^2, R^3, R^4, R^5,$ and $R^6 =$ hydrogen $R^7 = -(CH_2)_{13}OH$ |
| D6 14-(8-ethoxyquinolin-2-yl)tetradecan-1-ol | 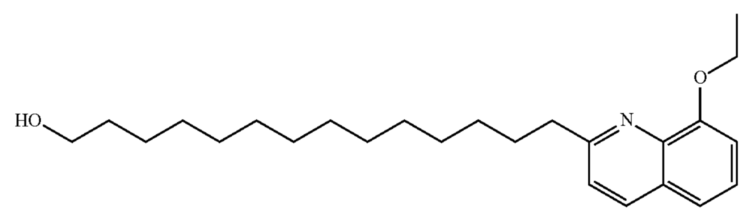 [SMILES: CCOc1cccc2ccc(CCCCCCCCCCCCCCO)nc12] | $R^1 = CH_2CH_3$ $R^2, R^3, R^4, R^5,$ and $R^6 =$ hydrogen $R^7 = -(CH_2)_{14}OH$ |
| D7 15-(8-ethoxyquinolin-2-yl)pentadecan-1-ol | 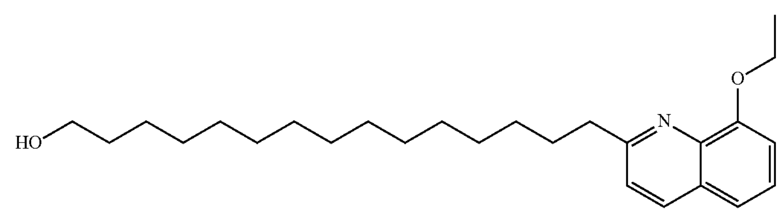 [SMILES: CCOc1cccc2ccc(CCCCCCCCCCCCCCCO)nc12] | $R^1 = CH_2CH_3$ $R^2, R^3, R^4, R^5,$ and $R^6 =$ hydrogen $R^7 = -(CH_2)_{15}OH$ |

-continued

| Cpd No. Chemical Name | Structure | Substituents |
|---|---|---|
| D8 11-(8-ethoxy-5-methylquinolin-2-yl)undecan-1-ol | 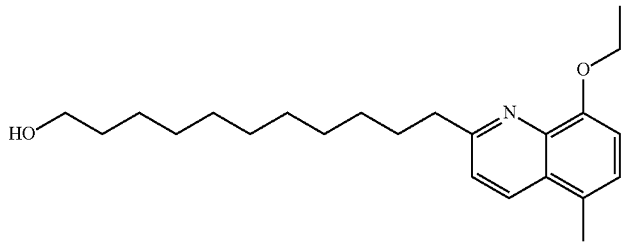 [SMILES: CCOc1ccc(C)c2ccc(CCCCCCCCCCCO)nc12] | $R^1 = CH_2CH_3$ $R^2, R^3, R^5,$ and $R^6 =$ hydrogen $R^4 = CH_3$ $R^7 = -(CH_2)_{11}OH$ |
| D9 11-(8-ethoxy-5-fluoroquinolin-2-yl)undecan-1-ol | 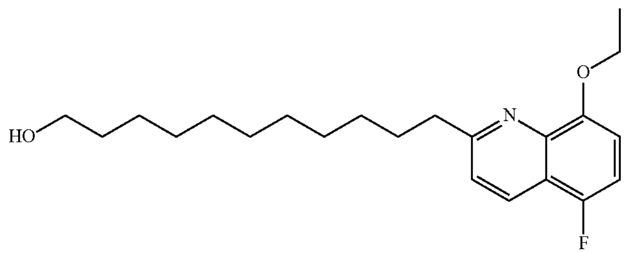 [SMILES: CCOc1ccc(F)c2ccc(CCCCCCCCCCCO)nc12] | $R^1 = CH_2CH_3$ $R^2, R^3, R^5,$ and $R^6 =$ hydrogen $R^4 = F$ $R^7 = -(CH_2)_{11}OH$ |
| D10 9-(5-chloro-8-ethoxyquinolin-2-yl)nonan-1-ol | 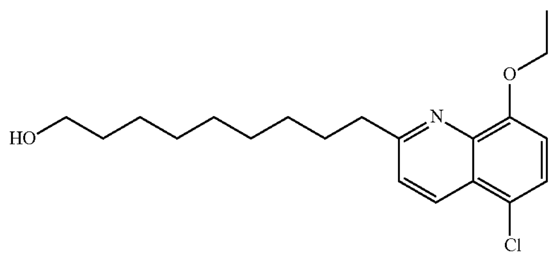 [SMILES: CCOc1ccc(Cl)c2ccc(CCCCCCCCCO)nc12] | $R^1 = CH_2CH_3$ $R^2, R^3, R^5,$ and $R^6 =$ hydrogen $R^4 = Cl$ $R^7 = -(CH_2)_9OH$ |
| D11 11-(5-chloro-8-ethoxyquinolin-2-yl)undecan-1-ol | 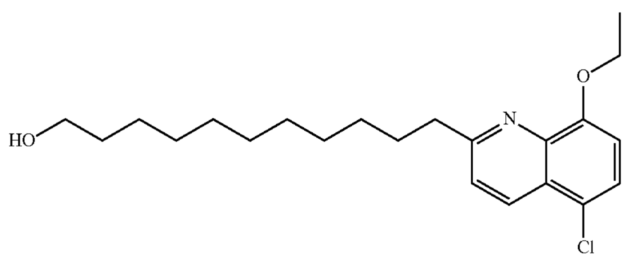 | $R^1 = CH_2CH_3$ $R^2, R^3, R^5,$ and $R^6 =$ hydrogen $R^4 = Cl$ $R^7 = -(CH_2)_{11}OH$ |

-continued

| Cpd No. Chemical Name | Structure | Substituents |
|---|---|---|
| D12 15-(5-chloro-8-ethoxyquinolin-2-yl)pentadecan-1-ol | 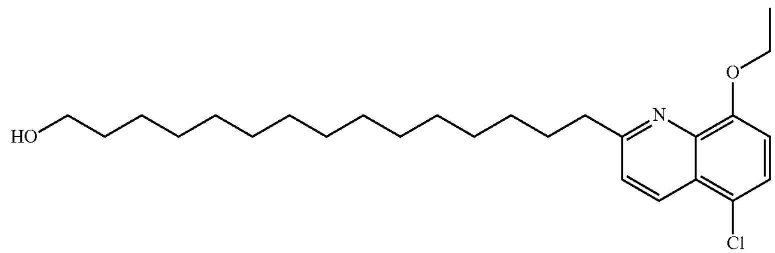 [SMILES: CCOc1ccc(Cl)c2ccc(CCCCCCCCCCCCCCCO)nc12] | $R^1 = CH_2CH_3$ $R^2, R^3, R^5$, and $R^6$ = hydrogen $R^4 = Cl$ $R^7 = —(CH_2)_{15}OH$ |
| D13 11-(5-bromo-8-ethoxyquinolin-2-yl)undecan-1-ol | 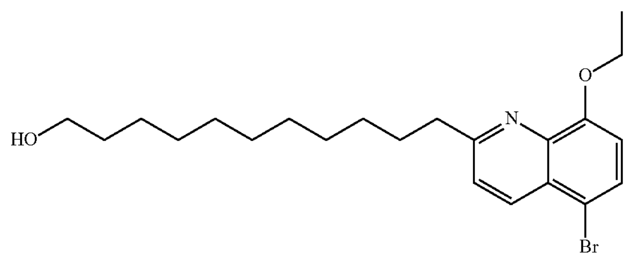 [SMILES: CCOc1ccc(Br)c2ccc(CCCCCCCCCCCO)nc12] | $R^1 = CH_2CH_3$ $R^2, R^3, R^5$, and $R^6$ = hydrogen $R^4 = Br$ $R^7 = —(CH_2)_{11}OH$ |
| D14 11-(5,7-dichloro-8-ethoxyquinolin-2-yl)undecan-1-ol | 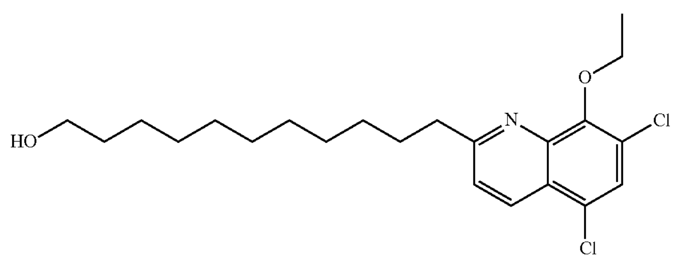 [SMILES: CCOc1c(Cl)cc(Cl)c2ccc(CCCCCCCCCCCO)nc12] | $R^1 = CH_2CH_3$ $R^2, R^4 = Cl$ $R^3, R^5$, and $R^6$ = hydrogen $R^7 = —(CH_2)_{11}OH$ |
| E1 9-(8-isopropoxyquinolin-2-yl)nonan-1-ol | 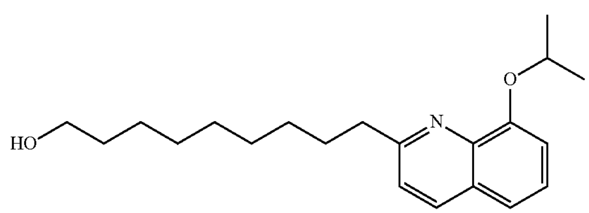 [SMILES: CC(C)Oc1cccc2ccc(CCCCCCCCCO)nc12] | $R^1 = CH(CH_3)_2$ $R^2, R^3, R^4, R^5$, and $R^6$ = hydrogen $R^7 = —(CH_2)_9OH$ |

-continued

| Cpd No. Chemical Name | Structure | Substituents |
|---|---|---|
| E2 10-(8-isopropoxyquinolin-2-yl)decan-1-ol | 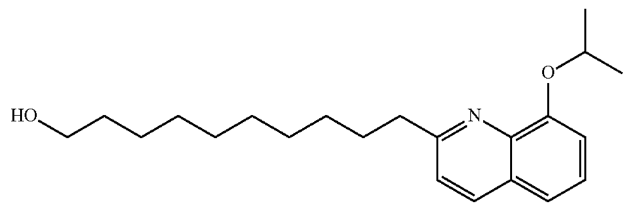 [SMILES: CC(C)Oc1cccc2ccc(CCCCCCCCCCO)nc12] | $R^1 = CH(CH_3)_2$ $R^2, R^3, R^4, R^5,$ and $R^6 =$ hydrogen $R^7 = —(CH_2)_{10}OH$ |
| E3 11-(8-isopropoxyquinolin-2-yl)undecan-1-ol | 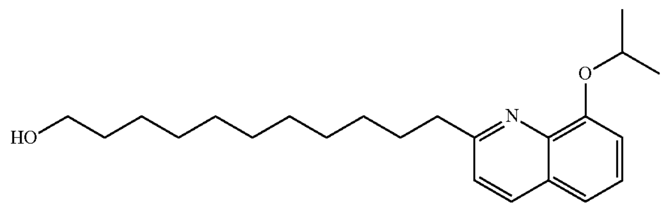 [SMILES: CC(C)Oc1cccc2ccc(CCCCCCCCCCCO)nc12] | $R^1 = CH(CH_3)_2$ $R^2, R^3, R^4, R^5,$ and $R^6 =$ hydrogen $R^7 = —(CH_2)_{11}OH$ |
| E4 12-(8-isopropoxyquinolin-2-yl)dodecan-1-ol | 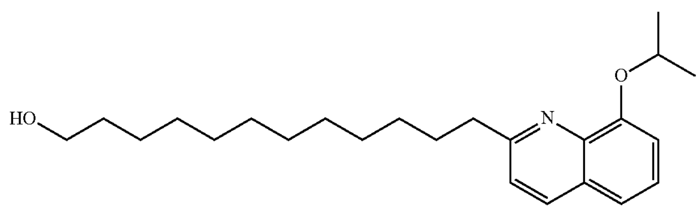 [SMILES: CC(C)Oc1cccc2ccc(CCCCCCCCCCCCO)nc12] | $R^1 = CH(CH_3)_2$ $R^2, R^3, R^4, R^5,$ and $R^6 =$ hydrogen $R^7 = —(CH_2)_{12}OH$ |
| E5 13-(8-isopropoxyquinolin-2-yl)tridecan-1-ol | 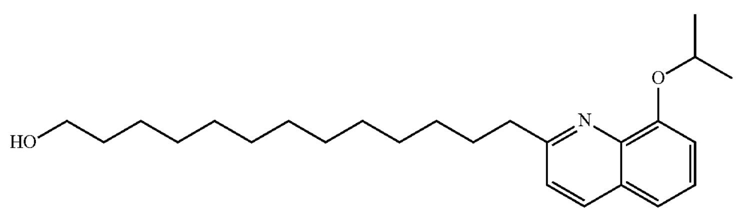 [SMILES: CC(C)Oc1cccc2ccc(CCCCCCCCCCCCCO)nc12] | $R^1 = CH(CH_3)_2$ $R^2, R^3, R^4, R^5,$ and $R^6 =$ hydrogen $R^7 = —(CH_2)_{13}OH$ |

-continued

| Cpd No. Chemical Name | Structure | Substituents |
|---|---|---|
| E6 14-(8-isopropoxyquinolin-2-yl)tetradecan-1-ol | 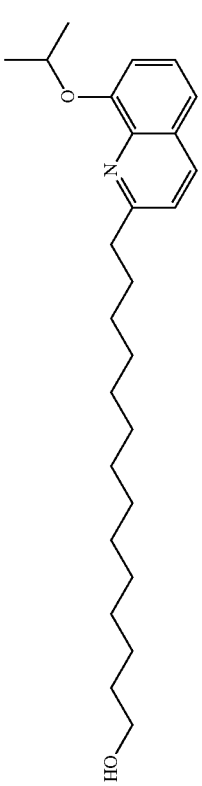 | $R^1 = CH(CH_3)_2$<br>$R^2, R^3, R^4, R^5,$ and $R^6 =$ hydrogen<br>$R^7 = -(CH_2)_{14}OH$ |
| E7 15-(8-isopropoxyquinolin-2-yl)pentadecan-1-ol | 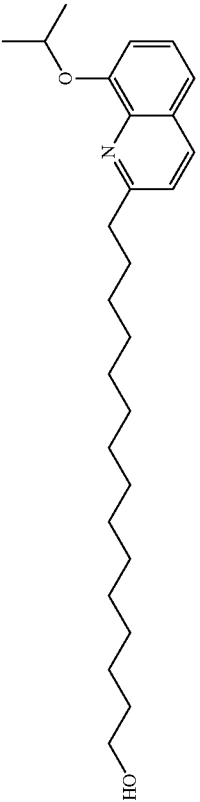 | $R^1 = CH(CH_3)_2$<br>$R^2, R^3, R^4, R^5,$ and $R^6 =$ hydrogen<br>$R^7 = -(CH_2)_{15}OH$ |
| E8 11-(8-isopropoxy-5-methylquinolin-2-yl)undecan-1-ol | 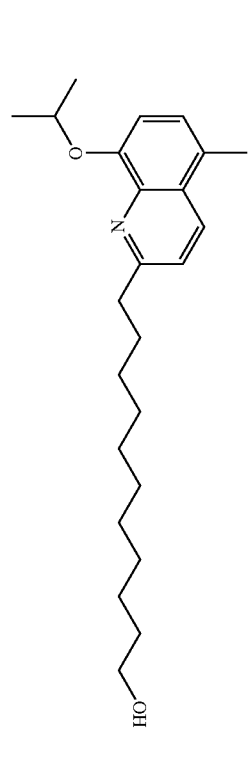 | $R^1 = CH(CH_3)_2$<br>$R^2, R^3, R^5,$ and $R^6 =$ hydrogen<br>$R^4 = CH_3$<br>$R^7 = -(CH_2)_{11}OH$ |
| E9 11-(5-fluoro-8-isopropoxyquinolin-2-yl)undecan-1-ol | 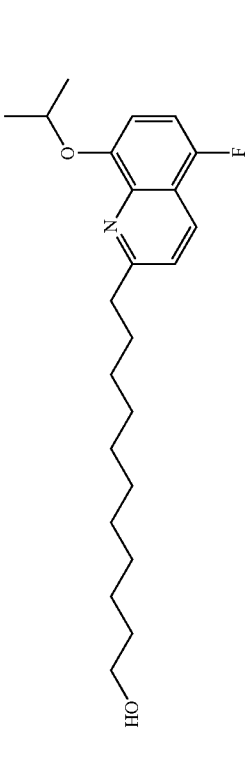 | $R^1 = CH(CH_3)_2$<br>$R^2, R^3, R^5,$ and $R^6 =$ hydrogen<br>$R^4 = F$<br>$R^7 = -(CH_2)_{11}OH$ |

-continued

| Cpd No. Chemical Name | Structure | Substituents |
|---|---|---|
| E10 9-(5-chloro-8-isopropoxyquinolin-2-yl)nonan-1-ol | | $R^1 = CH(CH_3)_2$ $R^2, R^3, R^5,$ and $R^6 =$ hydrogen $R^4 = Cl$ $R^7 = -(CH_2)_9OH$ |
| E11 11-(5-chloro-8-isopropoxyquinolin-2-yl)undecan-1-ol | | $R^1 = CH(CH_3)_2$ $R^2, R^3, R^5,$ and $R^6 =$ hydrogen $R^4 = Cl$ $R^7 = -(CH_2)_{11}OH$ |
| E12 15-(5-chloro-8-isopropoxyquinolin-2-yl)pentadecan-1-ol | | $R^1 = CH(CH_3)_2$ $R^2, R^3, R^5,$ and $R^6 =$ hydrogen $R^4 = Cl$ $R^7 = -(CH_2)_{15}OH$ |

-continued

| Cpd No. Chemical Name | Structure | Substituents |
|---|---|---|
| E13<br>11-(5-bromo-8-isopropoxyquinolin-2-yl)undecan-1-ol | | $R^1 = CH(CH_3)_2$<br>$R^2, R^3, R^5 = $ hydrogen<br>$R^6 = $ hydrogen<br>$R^4 = Br$<br>$R^7 = -(CH_2)_{11}OH$ |
| E14<br>11-(5,7-dichloro-8-isopropoxyquinolin-2-yl)undecan-1-ol | | $R^1 = CH(CH_3)_2$<br>$R^2, R^4 = Cl$<br>$R^3, R^5, $<br>$R^6 = $ hydrogen<br>$R^7 = -(CH_2)_{11}OH$ |
| Example 4 | | |
| F1<br>9-(8-(cyclopropylmethoxy)quinolin-2-yl)nonan-1-ol | | $R^1 = CH_2CH(CH_2)_2$<br>$R^2, R^3, R^4, R^5, $ and<br>$R^6 = $ hydrogen<br>$R^7 = -(CH_2)_9OH$ |
| F2<br>10-(8-(cyclopropylmethoxy)quinolin-2-yl)decan-1-ol | | $R^1 = CH_2CH(CH_2)_2$<br>$R^2, R^3, R^4, R^5, $ and<br>$R^6 = $ hydrogen<br>$R^7 = -(CH_2)_{10}OH$ |

-continued

| Cpd No. Chemical Name | Structure | Substituents |
|---|---|---|
| F3 11-(8-(cyclopropyl-methoxy)quinolin-2-yl)undecan-1-ol | 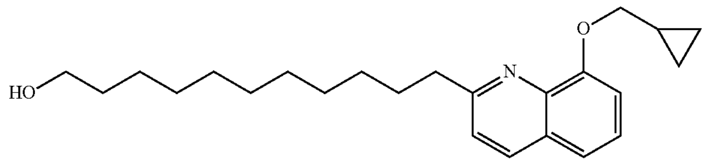 [SMILES: OCCCCCCCCCCCc1ccc2cccc(OCC3CC3)c2n1] | $R^1 = CH_2CH(CH_2)_2$ $R^2, R^3, R^4, R^5,$ and $R^6 =$ hydrogen $R^7 = -(CH_2)_{11}OH$ |
| F4 12-(8-(cyclopropyl-methoxy)quinolin-2-yl)dodecan-1-ol | 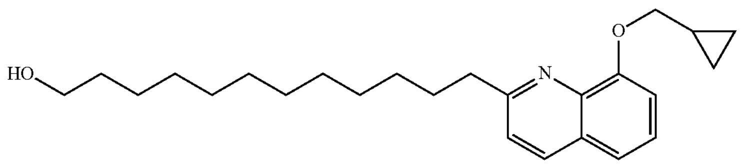 [SMILES: OCCCCCCCCCCCCc1ccc2cccc(OCC3CC3)c2n1] | $R^1 = CH_2CH(CH_2)_2$ $R^2, R^3, R^4, R^5,$ and $R^6 =$ hydrogen $R^7 = -(CH_2)_{12}OH$ |
| F5 13-(8-(cyclopropyl-methoxy)quinolin-2-yl)tridecan-1-ol | 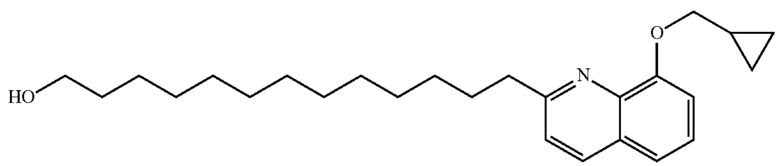 [SMILES: OCCCCCCCCCCCCCc1ccc2cccc(OCC3CC3)c2n1] | $R^1 = CH_2CH(CH_2)_2$ $R^2, R^3, R^4, R^5,$ and $R^6 =$ hydrogen $R^7 = -(CH_2)_{13}OH$ |
| F6 14-(8-(cyclopropyl-methoxy)quinolin-2-yl)tetradecan-1-ol | 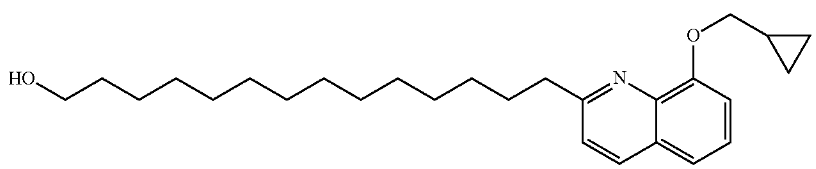 [SMILES: OCCCCCCCCCCCCCCc1ccc2cccc(OCC3CC3)c2n1] | $R^1 = CH_2CH(CH_2)_2$ $R^2, R^3, R^4, R^5,$ and $R^6 =$ hydrogen $R^7 = -(CH_2)_{14}OH$ |
| F7 15-(8-(cyclopropyl-methoxy)quinolin-2-yl)pentadecan-1-ol | 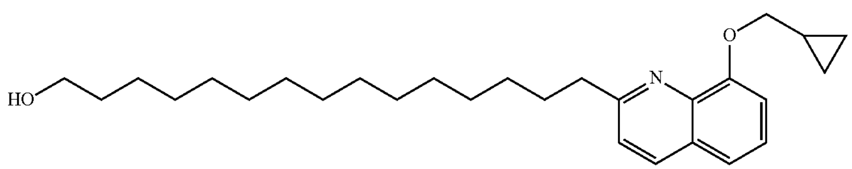 [SMILES: OCCCCCCCCCCCCCCCc1ccc2cccc(OCC3CC3)c2n1] | $R^1 = CH_2CH(CH_2)_2$ $R^2, R^3, R^4, R^5,$ and $R^6 =$ hydrogen $R^7 = -(CH_2)_{15}OH$ |

-continued

| Cpd No. Chemical Name | Structure | Substituents |
|---|---|---|
| F8 11-(8-(cyclopropyl-methoxy)-5-methylquinolin-2-yl)undecan-1-ol | 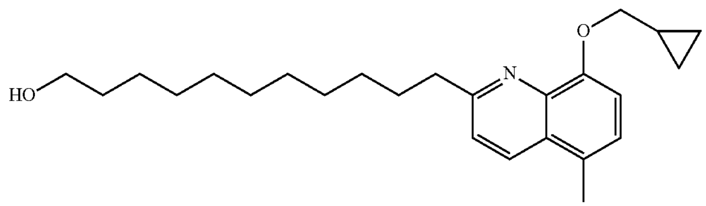 [SMILES: Cc1ccc(OCC2CC2)c2nc(CCCCCCCCCCCO)ccc12] | $R^1 = CH_2CH(CH_2)_2$ $R^2, R^3, R^5$, and $R^6$ = hydrogen $R^4 = CH_3$ $R^7 = -(CH_2)_{11}OH$ |
| F9 11-(8-(cyclopropyl-methoxy)-5-fluoroquinolin-2-yl)undecan-1-ol | 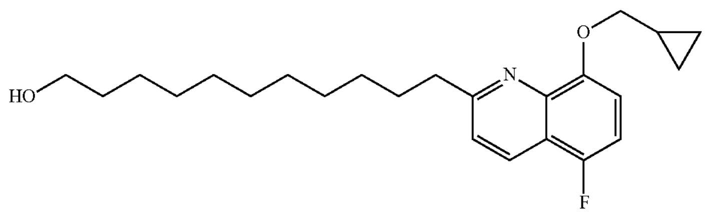 [SMILES: OCCCCCCCCCCCc1ccc2c(F)ccc(OCC3CC3)c2n1] | $R^1 = CH_2CH(CH_2)_2$ $R^2, R^3, R^5$, and $R^6$ = hydrogen $R^4 = F$ $R^7 = -(CH_2)_{11}OH$ |
| F10 9-(5-chloro-8-(cyclopropylmethoxy)quinolin-2-yl)nonan-1-ol | 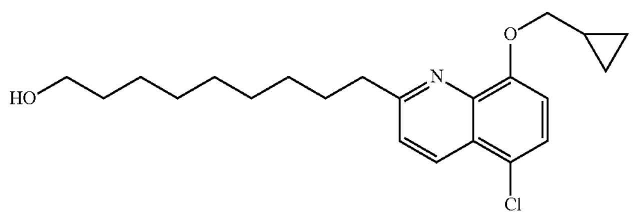 [SMILES: OCCCCCCCCCc1ccc2c(Cl)ccc(OCC3CC3)c2n1] | $R^1 = CH_2CH(CH_2)_2$ $R^2, R^3, R^5$, and $R^6$ = hydrogen $R^4 = Cl$ $R^7 = -(CH_2)_9OH$ |
| F11 11-(5-chloro-8-(cyclopropylmethoxy)quinolin-2-yl)undecan-1-ol | 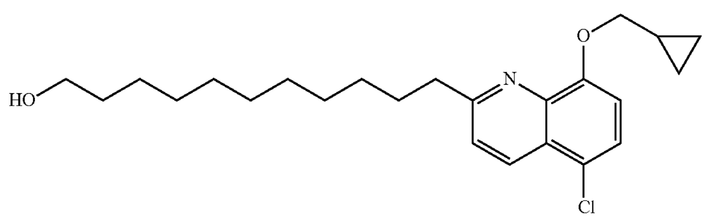 [SMILES: OCCCCCCCCCCCc1ccc2c(Cl)ccc(OCC3CC3)c2n1] | $R^1 = CH_2CH(CH_2)_2$ $R^2, R^3, R^5$, and $R^6$ = hydrogen $R^4 = Cl$ $R^7 = -(CH_2)_{11}OH$ |

-continued

| Cpd No. Chemical Name | Structure | Substituents |
|---|---|---|
| F12 15-(5-chloro-8-(cyclopropylmethoxy) quinolin-2-yl)pentadecan-1-ol | 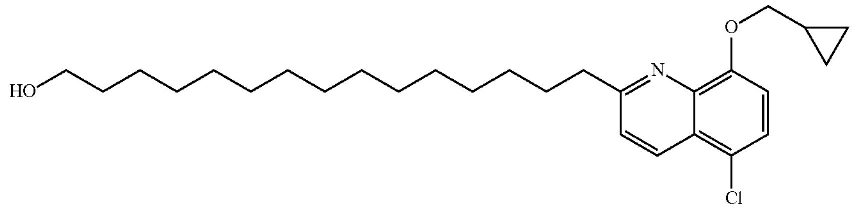 [SMILES: OCCCCCCCCCCCCCCCc1ccc2c(Cl)ccc(OCC3CC3)c2n1] | $R^1 = CH_2CH(CH_2)_2$ $R^2, R^3, R^5,$ and $R^6 =$ hydrogen $R^4 = Cl$ $R^7 = -(CH_2)_{15}OH$ |
| F13 11-(5-bromo-8-(cyclopropylmethoxy) quinolin-2-yl)undecan-1-ol | 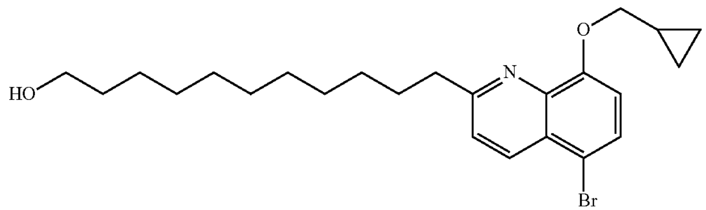 [SMILES: OCCCCCCCCCCCc1ccc2c(Br)ccc(OCC3CC3)c2n1] | $R^1 = CH_2CH(CH_2)_2$ $R^2, R^3, R^5,$ and $R^6 =$ hydrogen $R^4 = Br$ $R^7 = -(CH_2)_{11}OH$ |
| F14 11-(5,7-dichloro-8-(cyclopropylmethoxy) quinolin-2-yl)undecan-1-ol | 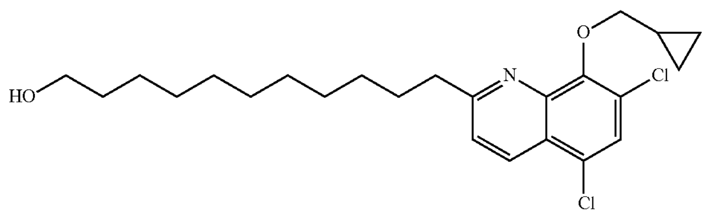 [SMILES: OCCCCCCCCCCCc1ccc2c(Cl)cc(Cl)c(OCC3CC3)c2n1] | $R^1 = CH_2CH(CH_2)_2$ $R^2, R^4 = Cl$ $R^3, R^5,$ and $R^6 =$ hydrogen $R^7 = -(CH_2)_{11}OH$ |

Example 5

| G1 5,7-dichloro-2-(11-hydroxyundecyl) quinolin-8-ol | 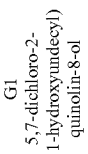 | $R^1 =$ hydrogen $R^2, R^4 = Cl$ $R^3, R^5,$ and $R^6 =$ hydrogen $R^7 = -(CH_2)_{11}OH$ |

Example 6

-continued

| Cpd No. Chemical Name | Structure | Substituents |
|---|---|---|
| H1A 10-(5-Chloro-8-methoxyquinolin-2-yl)decan-1-ol | 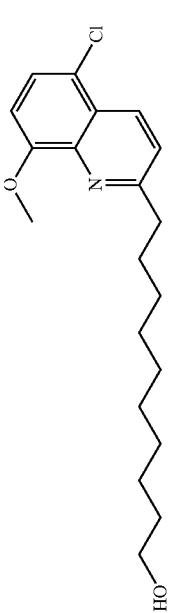 | $R^1 = CH_3$<br>$R^2, R^3, R^5,$ and $R^6 =$ hydrogen<br>$R^4 = Cl$<br>$R^7 = -(CH_2)_{10}OH$ |
| H1B acetic acid 10-(5-chloro-8-methoxyquinolin-2-yl)decyl ester | 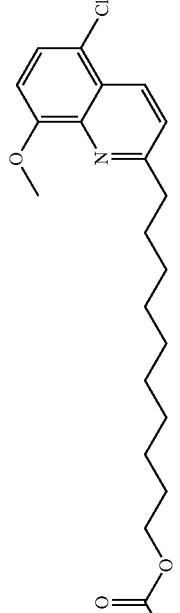 | $R^1 = CH_3$<br>$R^2, R^3, R^5,$ and $R^6 =$ hydrogen<br>$R^4 = Cl$<br>$R^7 = (CH_2)_{10}OCOCH_3$ |
| H2A 11-(5-Chloro-8-methoxyquinolin-2-yl)undecan-1-ol | 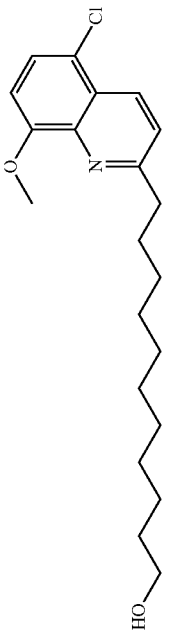 | $R^1 = CH_3$<br>$R^2, R^3, R^5,$ and $R^6 =$ hydrogen<br>$R^4 = Cl$<br>$R^7 = -(CH_2)_{11}OH$ |
| H2B acetic acid 11-(5-chloro-8-methoxyquinolin-2-yl)undecyl ester | 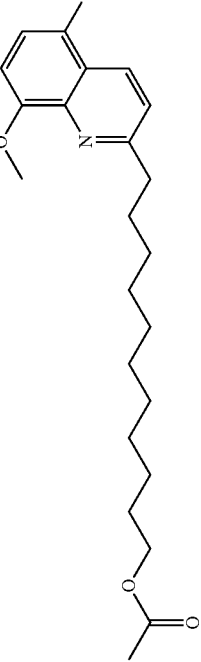 | $R^1 = CH_3$<br>$R^2, R^3, R^5,$ and $R^6 =$ hydrogen<br>$R^4 = Cl$<br>$R^7 = (CH_2)_{11}OCOCH_3$ |
| H3A 12-(5-Chloro-8-methoxyquinolin-2-yl)dodecan-1-ol | 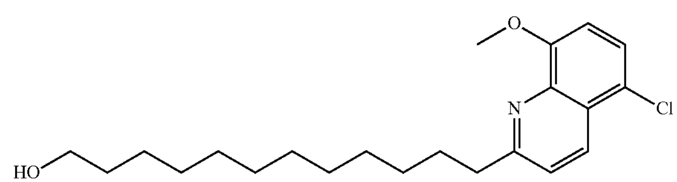 [SMILES: COc1ccc(Cl)c2ccc(CCCCCCCCCCCCO)nc12] | $R^1 = CH_3$<br>$R^2, R^3, R^5,$ and $R^6 =$ hydrogen<br>$R^4 = Cl$<br>$R^7 = -(CH_2)_{12}OH$ |

-continued

| Cpd No. Chemical Name | Structure | Substituents |
|---|---|---|
| H3B acetic acid 12-(5-chloro-8-methoxyquinolin-2-yl)dodecyl ester | 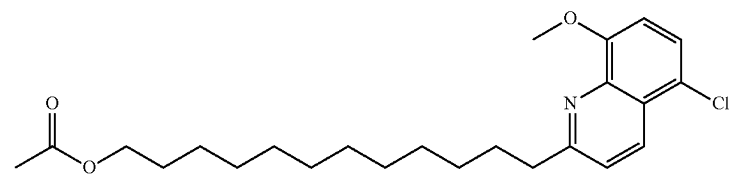 [SMILES: COc1ccc(Cl)c2ccc(CCCCCCCCCCCCOC(C)=O)nc12] | $R^1 = CH_3$<br>$R^2, R^3, R^5$, and $R^6$ = hydrogen<br>$R^4 = Cl$<br>$R^7 = -(CH_2)_{12}OCOCH_3$ |
| H4A 13-(5-Chloro-8-methoxyquinolin-2-yl)tridecan-1-ol | 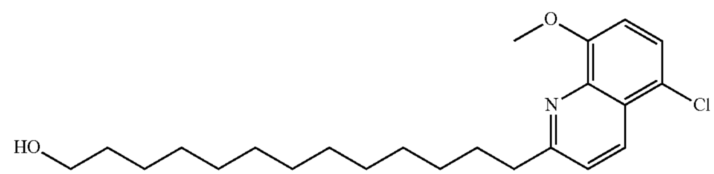 [SMILES: COc1ccc(Cl)c2ccc(CCCCCCCCCCCCCO)nc12] | $R^1 = CH_3$<br>$R^2, R^3, R^5$, and $R^6$ = hydrogen<br>$R^4 = Cl$<br>$R^7 = -(CH_2)_{13}OH$ |
| H4B acetic acid 13-(5-chloro-8-methoxyquinolin-2-yl)tridecyl ester | 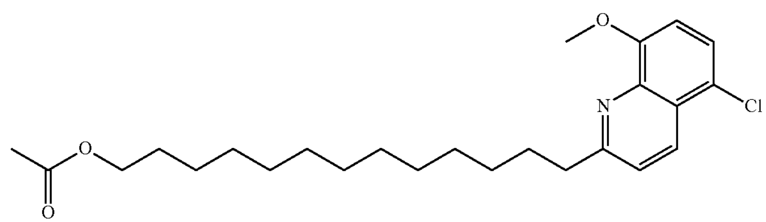 [SMILES: COc1ccc(Cl)c2ccc(CCCCCCCCCCCCCOC(C)=O)nc12] | $R^1 = CH_3$<br>$R^2, R^3, R^5$, and $R^6$ = hydrogen<br>$R^4 = Cl$<br>$R^7 = -(CH_2)_{10}OCOCH_3$ |

Example 7

| Cpd No. Chemical Name | Structure | Substituents |
|---|---|---|
| I1 11-(8-methoxyquinolin-4-yl)undecan-1-ol | | $R^1 = CH_3$<br>$R^2, R^3, R^4, R^6$, and $R^7$ = hydrogen<br>$R^5 = -(CH_2)_{11}OH$ |
| I2 11-(8-ethoxyquinolin-4-yl)undecan-1-ol | | $R^1 = CH_2CH_3$<br>$R^2, R^3, R^4, R^6$, and $R^7$ = hydrogen<br>$R^5 = -(CH_2)_{11}OH$ |

-continued

| Cpd No. Chemical Name | Structure | Substituents |
|---|---|---|
| I3 11-(8-isopropoxyquinolin-4-yl)undecan-1-ol | | $R^1 = CH(CH_3)_2$ $R^2, R^3, R^4, R^6,$ and $R^7 =$ hydrogen $R^5 = —(CH_2)_{11}OH$ |
| I4 11-(8-(cyclopropylmethoxy)quinolin-4-yl)undecan-1-ol | | $R^1 = CH_2CH(CH_2)_2$ $R^2, R^3, R^4, R^6,$ and $R^7 =$ hydrogen $R^5 = —(CH_2)_{11}OH$ |
| J1 11-(8-(benzyloxy)quinolin-4-yl)undecan-1-ol | | $R^1 =$ benzyl $R^2, R^3, R^4, R^6,$ and $R^7 =$ hydrogen $R^5 = —(CH_2)_{11}OH$ |
| J2 12-(8-(benzyloxy)quinolin-4-yl)dodecan-1-ol | | $R^1 =$ benzyl $R^2, R^3, R^4, R^6,$ and $R^7 =$ hydrogen $R^5 = —(CH_2)_{12}OH$ |
| K1 4-(11-hydroxyundecyl)quinolin-1-ol | | $R^1 =$ hydrogen $R^2, R^3, R^4, R^6,$ and $R^7 =$ hydrogen $R^5 = —(CH_2)_{11}OH$ |

-continued

| Cpd No. Chemical Name | Structure | Substituents |
|---|---|---|
| K2 4-(12-hydroxyundecyl) quinolin-1-ol | 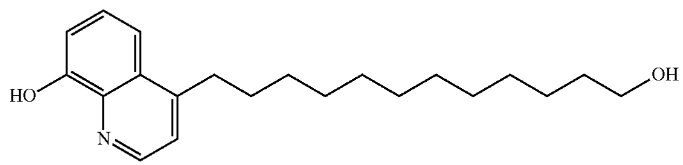 [SMILES: OCCCCCCCCCCCCc1ccnc2c(O)cccc12] | $R^1$ = hydrogen $R^2, R^3, R^4, R^6,$ and $R^7$ = hydrogen $R^5$ = —$(CH_2)_{12}OH$ |

Example 8

| L1 9-(8-(trifluoromethoxy) quinolin-2-yl)nona-1-ol | | $R^1 = CF_3$ $R^2, R^3, R^4, R^5,$ and $R^6$ = hydrogen $R^7$ = —$(CH_2)_9OH$ |
| L2 11-(8-(trifluoromethoxy) quinolin-2-yl)undecan-1-ol | | $R^1 = CF_3$ $R^2, R^3, R^4, R^5,$ and $R^6$ = hydrogen $R^7$ = —$(CH_2)_{11}OH$ |
| L3 14-(8-(trifluoromethoxy) quinolin-2-yl)tetradecan-1-ol | | $R^1 = CF_3$ $R^2, R^3, R^4, R^5,$ and $R^6$ = hydrogen $R^7$ = —$(CH_2)_{14}OH$ |

-continued

| Cpd No. Chemical Name | Structure | Substituents |
|---|---|---|
| L4 15-(8-(trifluoromethoxy)quinolin-2-yl)pentadecan-1-ol | (structure shown) | $R^1 = CF_3$<br>$R^2, R^3, R^4, R^5,$ and $R^6$ = hydrogen<br>$R^7 = —(CH_2)_{15}OH$ |
| Example 9 | | |
| M1 2-(4-(2-hydroxyethyl)piperazin-1-yl)methyl)quinolin-8-ol | (structure shown) | $R^1$ = hydrogen<br>$R^2, R^3, R^4, R^5,$ and $R^6$ = hydrogen<br>$R^7 = —CH_2—(N(CH_2CH_2)_2N)CH_2CH_2OH$ |
| M2 2-(4-((5-chloro-8-methoxyquinolin-2-yl)methyl)piperazin-1-yl)ethanol | (structure shown) | $R^1$ = methyl<br>$R^2, R^3, R^5,$ and $R^6$ = hydrogen<br>$R^4 = Cl$<br>$R^7 = —CH_2—(N(CH_2CH_2)_2N)CH_2CH_2OH$ |

-continued

| Cpd No. Chemical Name | Structure | Substituents |
|---|---|---|
| M3 2-(4-((5-chloro-8-ethoxyquinolin-2-yl)methyl)piperazin-1-yl)ethanol | | $R^1 = CH_2CH_3$<br>$R^2, R^3, R^5$, and $R^6$ = hydrogen<br>$R^4 = Cl$<br>$R^7 = -CH_2-(N(CH_2CH_2)_2N)CH_2CH_2OH$ |
| M4 2-(4-((5-chloro-8-isopropoxyquinolin-2-yl)methyl)piperazin-1-yl)ethanol | | $R^1 = CH(CH_3)_2$<br>$R^2, R^3, R^5$, and $R^6$ = hydrogen<br>$R^4 = Cl$<br>$R^7 = -CH_2-(N(CH_2CH_2)_2N)CH_2CH_2OH$ |
| M5 2-(4-((5-chloro-8-(cyclopropylmethyoxy)quinolin-2-yl)methyl)piperazin-1-yl)ethane | | $R^1 = CH_2CH(CH_3)_2$<br>$R^2, R^3, R^5$, and $R^6$ = hydrogen<br>$R^4 = Cl$<br>$R^7 = -CH_2-(N(CH_2CH_2)_2N)CH_2CH_3$ |

-continued

| Cpd No. Chemical Name | Structure | Substituents |
|---|---|---|
| M6 2-(4-((5,7-dichloro-8-methoxyquinolin-2-yl)methyl)piperazin-1-yl)ethanol | [structure: 5,7-dichloro-8-methoxyquinoline with 2-(piperazinylmethyl) bearing N-CH2CH2OH] | $R^1 = CH_3$<br>$R^2, R^4 = Cl$<br>$R^3, R^5, R^6 = $ hydrogen<br>$R^7 = —CH_2—(N(CH_2CH_2)_2N)CH_2CH_2OH$ |
| M7 2-(4-((5,7-dichloro-8-(cyclopropylmethoxy)quinolin-2-yl)methyl)piperazin-1-yl)ethanol | [structure: 5,7-dichloro-8-(cyclopropylmethoxy)quinoline with 2-(piperazinylmethyl) bearing N-CH2CH2OH] | $R^1 = CH_2CH(CH_2)_2$<br>$R^2, R^4 = Cl$<br>$R^3, R^5, R^6 = $ hydrogen<br>$R^7 = —CH_2—(N(CH_2CH_2)_2N)CH_2CH_2OH$ |
| N1 2-((methyl(prop-2-ynyl)amino)methyl)quinolin-8-ol | [structure: 8-hydroxyquinoline with 2-(N-methyl-N-propargylaminomethyl)] | $R^1 = $ hydrogen<br>$R^2, R^3, R^4, R^5, $ and $R^6 = $ hydrogen<br>$R^7 = —CH_2N(CH_3)CH_2C{\equiv}CH$ |
| N2 5-chloro-2-(((methyl(prop-2-ynyl)amino)methyl)quinolin-8-ol | [structure: 5-chloro-8-hydroxyquinoline with 2-(N-methyl-N-propargylaminomethyl)] | $R^1 = $ hydrogen<br>$R^2, R^3, R^5, $ and $R^6 = $ hydrogen<br>$R^4 = Cl$<br>$R^7 = —CH_2N(CH_3)CH_2C{\equiv}CH$ |

-continued

| Cpd No. Chemical Name | Structure | Substituents |
|---|---|---|
| N3 N-((5-chloro-8-methoxyquinolin-2-yl)methyl)-N-methylprop-2-yn-1-amine | 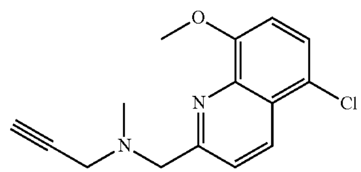 [SMILES: C#CCN(C)Cc1ccc2c(Cl)ccc(OC)c2n1] | $R^1 = CH_3$ $R^2, R^3, R^5,$ and $R^6 =$ hydrogen $R^4 = Cl$ $R^7 = -CH_2N(CH_3)CH_2C\equiv CH$ |
| N4 N-((5-chloro-8-ethoxyquinolin-2-yl)methyl)-N-methylprop-2-yn-1-amine | 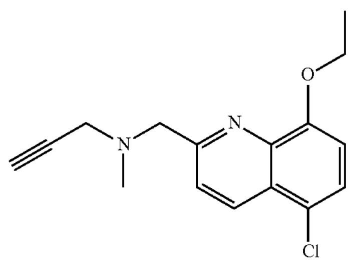 [SMILES: C#CCN(C)Cc1ccc2c(Cl)ccc(OCC)c2n1] | $R^1 = CH_2CH_3$ $R^2, R^3, R^5,$ and $R^6 =$ hydrogen $R^4 = Cl$ $R^7 = -CH_2N(CH_3)CH_2C\equiv CH$ |
| N5 N-((5-chloro-8-isopropoxyquinolin-2-yl)methyl)-N-methylprop-2-yn-1-amine | 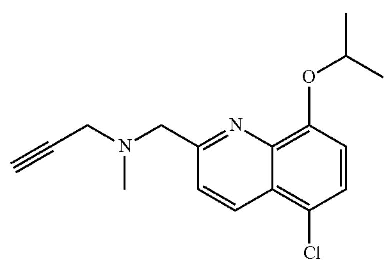 [SMILES: C#CCN(C)Cc1ccc2c(Cl)ccc(OC(C)C)c2n1] | $R^1 = CH(CH_3)_2$ $R^2, R^3, R^5,$ and $R^6 =$ hydrogen $R^4 = Cl$ $R^7 = -CH_2N(CH_3)CH_2C\equiv CH$ |
| N6 N-((5-chloro-8-(cyclopropylmethoxy)quinolin-2-yl)methyl)-N-methylprop-2-yn-1-amine | 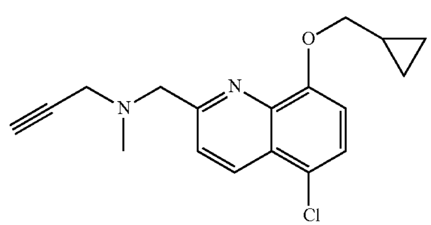 [SMILES: C#CCN(C)Cc1ccc2c(Cl)ccc(OCC3CC3)c2n1] | $R^1 = CH_2CH(CH_2)_2$ $R^2, R^3, R^5,$ and $R^6 =$ hydrogen $R^4 = Cl$ $R^7 = -CH_2N(CH_3)CH_2C\equiv CH$ |

-continued

| Cpd No. Chemical Name | Structure | Substituents |
|---|---|---|
| N7<br>N-((5,7-dichloro-8-methoxyquinolin-2-yl)methyl)-N-methylprop-2-yn-1-amine | 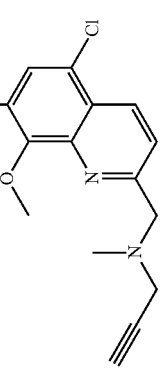 | $R^1 = CH_3$,<br>$R^2, R^4 = Cl$<br>$R^3, R^5$, and<br>$R^6 =$ hydrogen<br>$R^7 = -CH_2N(CH_3)CH_2C{\equiv}CH$ |
| N8<br>N-((5,7-dichloro-8-(cyclopropylmethoxy)quinolin-2-yl)methyl)-N-methylprop-2-yn-1-amine | 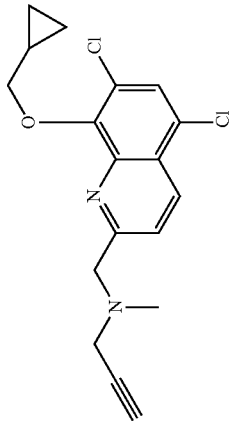 | $R^1 = CH_2CH(CH_2)_2$<br>$R^2, R^4 = Cl$<br>$R^3, R^5$, and<br>$R^6 =$ hydrogen<br>$R^7 = -CH_2N(CH_3)CH_2C{\equiv}CH$ |
| O1<br>8-((5-chloro-8-methoxyquinolin-2-yl)methylamino)octan-1-ol | 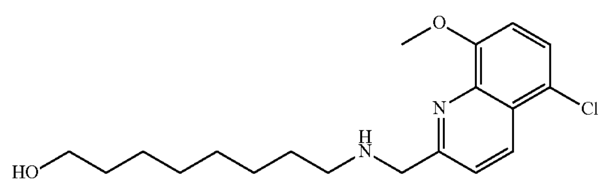 [SMILES: COc1ccc(Cl)c2ccc(CNCCCCCCCCO)nc12] | $R^1 = CH_3$,<br>$R^2, R^3, R^5$, and<br>$R^6 =$ hydrogen<br>$R^4 = Cl$<br>$R^7 = CH_2NH(CH_2)_8OH$ |
| O2<br>8-((5-chloro-8-ethoxyquinolin-2-yl)methylamino)octan-1-ol | 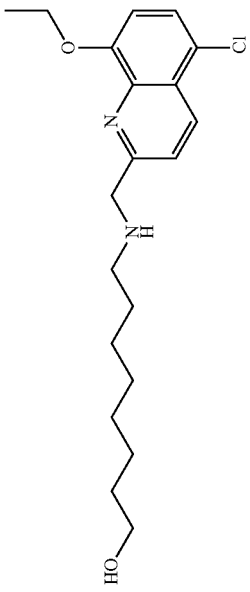 | $R^1 = CH_2CH_3$<br>$R^2, R^3, R^5$, and<br>$R^6 =$ hydrogen<br>$R^4 = Cl$<br>$R^7 = CH_2NH(CH_2)_8OH$ |

-continued

| Cpd No. Chemical Name | Structure | Substituents |
|---|---|---|
| O3<br>8-((5-chloro-8-isopropoxyquinolin-2-yl)methylamino)octan-1-ol | | $R^1 = CH(CH_3)_2$<br>$R^2, R^3, R^5,$ and $R^6 =$ hydrogen<br>$R^4 = Cl$<br>$R^7 = CH_2NH(CH_2)_8OH$ |
| O4<br>8-((5-chloro-8-(cyclopropylmethoxy)quinolin-2-yl)methylamino)octan-1-ol | | $R^1 = CH_2CH(CH_2)_2$<br>$R^2, R^3, R^5,$ and $R^6 =$ hydrogen<br>$R^4 = Cl$<br>$R^7 = CH_2NH(CH_2)_8OH$ |
| O5<br>8-((5,7-dichloro-8-methoxyquinolin-2-yl)methylamino)octan-1-ol | | $R^1 = CH_3,$<br>$R^2, R^4 = Cl$<br>$R^3, R^5,$ and $R^6 =$ hydrogen<br>$R^7 = CH_2NH(CH_2)_8OH$ |
| O6<br>8-((5,7-dichloro-8-(cyclopropylmethoxy)quinolin-2-yl)methylamino)octan-1-ol | | $R^1 = CH_2CH(CH_2)_2$<br>$R^2 = Cl$<br>$R^3, R^5,$ and $R^6 =$ hydrogen<br>$R^4 = Cl$<br>$R^7 = CH_2NH(CH_2)_8OH$ |

| Cpd No. Chemical Name | Structure | Substituents |
|---|---|---|
| P1 6-(bis((8-methoxyquinolin-2-yl)methyl)amino) hexan-1-ol | (structure) | $R^1 = CH_3$, $R^2, R_4, R^3, R^5,$ and $R^6$ = hydrogen $R^7 = CH_2N((CH_2)_6OH)CH_2(8$-methoxyquinolin-2-yl) |

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A compound of Formula (I) or a pharmaceutically acceptable salt thereof:

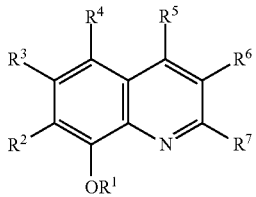

Formula (I)

(I) wherein
  $R^1$ is hydrogen, $(C_1-C_8)$alkyl, $(C_1-C_8)$alkylene$(C_3-C_8)$cycloalkyl, $(C_1-C_8)$haloalkyl, or $(C_1-C_8)$alkylene$(C_6-C_{20})$aryl;
  $R^2$ is hydrogen or halogen;
  $R^3$ is hydrogen, halogen, $(C_1-C_8)$alkyl, or $(C_1-C_8)$alkoxy;
  $R^4$ is hydrogen, halogen, $(C_1-C_8)$alkyl, $(C_1-C_8)$alkoxy, or $(C_1-C_8)$haloalkyl;
  $R^5$ is hydrogen or $(C_1-C_{20})$alkanol;
  $R^6$ is hydrogen; and
  $R^7$ is $(C_5-C_{20})$alkanol, $(C_1-C_8)$alkylene $(C_3-C_8)$heterocyclyl$(C_1-C_{20})$alkanol, $(C_1-C_8)$alkylene $(C_3-C_8)$heterocyclyl$(C_1-C_{20})$alkyl, $(C_{10}-C_{13})$alkyleneOCOCH$_3$, $(C_1-C_8)$alkylene$(C_1-C_6)$alkylamino$(C_1-C_6)$alkynyl, $(C_1-C_8)$alkyleneamino$(C_1-C_{20})$alkanol, or $(C_1-C_8)$alkyleneamino$(C_1-C_{20})$alkanol$(C_1-C_8)$alkylene substituted $(C_3-C_{20})$heteroaryl;
or (II) wherein:
  $R^1$, $R^2$, $R^3$, $R^4$ and $R^6$ are each defined in (I) above;
  $R^5$ is $(C_1-C_{20})$alkanol;
  $R^7$ is hydrogen, $(C_5-C_{20})$alkanol, $(C_5-C_8)$alkylene $(C_3-C_8)$heterocyclyl$(C_1-C_{20})$alkanol, $(C_5-C_8)$alkylene $(C_3-C_8)$heterocyclyl$(C_1-C_{20})$alkyl, $(C_{10}-C_{13})$alkyleneOCOCH$_3$, $(C_1-C_8)$alkylene$(C_1-C_6)$alkylamino$(C_1-C_6)$alkynyl, $(C_1-C_8)$alkyleneamino$(C_1-C_{20})$alkanol, or $(C_1-C_8)$alkyleneamino$(C_1-C_{20})$alkanol$(C_1-C_8)$alkylene substituted $(C_3-C_{20})$heteroaryl.

2. The compound of claim 1, wherein
(A) wherein:
  $R^1$ is hydrogen, $CH_3$, $CH_2CH_3$, $CH(CH_3)_2$, $CH_2CH(CH_2)_2$, $CH_2CH(CH_3)_2$, $CF_3$, or benzyl;
  $R^2$ is hydrogen, F, or Cl;
  $R^3$ is hydrogen, F, Cl, $CH_3$, or $OCH_3$;
  $R^4$ is hydrogen, F, Cl, Br, $CH_3$, $OCH_3$, or $CF_3$;
  $R^5$ is hydrogen, $(CH_2)_{11}OH$, or $(CH_2)_{12}OH$;
  $R^6$ is hydrogen; and
  $R^7$ is $(CH_2)_9OH$, $(CH_2)_{10}OH$, $(CH_2)_{11}OH$, $(CH_2)_{12}OH$, $(CH_2)_{13}OH$, $(CH_2)_{14}OH$, $(CH_2)_{15}OH$, $(CH_2)_{10}OCOCH_3$, $(CH_2)_{11}OCOCH_3$, $(CH_2)_{12}OCOCH_3$, $(CH_2)_{13}OCOCH_3$, $CH_2(N(CH_2CH_2)_2N)CH_2CH_2OH$, $CH_2(N(CH_2CH_2)_2N)CH_2CH_3$, $CH_2N(CH_3)CH_2C{\equiv}CH$, $CH_2NH(CH_2)_8OH$, or $CH_2N((CH_2)_6OH)CH_2$(8-methoxyquinolin-2-yl);
or (B) wherein:
  $R^1$, $R^2$, $R^3$, $R^4$ and $R^6$ are each defined in (A) above;
  $R^5$ is $(CH_2)_{11}OH$, or $(CH_2)_{12}OH$; and
  $R^7$ is hydrogen, $(CH_2)_9OH$, $(CH_2)_{10}OH$, $(CH_2)_{11}OH$, $(CH_2)_{12}OH$, $(CH_2)_{13}OH$, $(CH_2)_{14}OH$, $(CH_2)_{15}OH$, $(CH_2)_{10}OCOCH_3$, $(CH_2)_{11}OCOCH_3$, $(CH_2)_{12}OCOCH_3$, $(CH_2)_{13}OCOCH_3$, $CH_2(N(CH_2CH_2)_2N)CH_2CH_2OH$, $CH_2(N(CH_2CH_2)_2N)CH_2CH_3$, $CH_2N(CH_3)CH_2C{\equiv}CH$, $CH_2NH(CH_2)_8OH$, or $CH_2N((CH_2)_6 OH)CH_2$(8-methoxyquinolin-2-yl).

3. The compound of claim 2, wherein
  $R^1$ is hydrogen, $CH_3$, $CH_2CH_3$, $CH(CH_3)_2$, $CH_2CH(CH_3)_2$, $CH_2CH(CH_2)_2$, $CF_3$, or benzyl;
  $R^2$, $R^3$, $R^4$, $R^5$, and $R^6$ are each independently hydrogen; and
  $R^7$ is $(CH_2)_9OH$, $(CH_2)_{10}OH$, $(CH_2)_{11}OH$, $(CH_2)_{12}OH$, $(CH_2)_{13}OH$, $(CH_2)_{14}OH$, $(CH_2)_{15}OH$, $CH_2(N(CH_2CH_2)_2N)CH_2CH_2OH$, or $CH_2N(CH_3)CH_2C{\equiv}CH$.

4. The compound of claim 2, wherein
  $R^1$ is hydrogen, $CH_3$, $CH_2CH_3$, $CH_2CH(CH_3)_2$, $CH_2CH(CH_2)_2$, or $CH(CH_3)_2$;
  $R^2$, $R^3$, $R^5$, and $R^6$ are each independently hydrogen;
  $R^4$ is $CH_3$, F, Cl, Br, $CF_3$ or $OCH_3$; and
  $R^7$ is $(CH_2)_9OH$, $(CH_2)_{10}OH$, $(CH_2)_{11}OH$, $(CH_2)_{12}OH$, $(CH_2)_{13}OH$, $(CH_2)_{15}OH$, $(CH_2)_{10}OCOCH_3$, $(CH_2)_{11}OCOCH_3$, $(CH_2)_{12}OCOCH_3$, $(CH_2)_{13}OCOCH_3$, $CH_2NH(CH_2)_8OH$, $CH_2(N(CH_2CH_2)_2N)CH_2CH_2OH$, $CH_2(N(CH_2CH_2)_2N)CH_2CH_3$, or $CH_2N(CH_3)CH_2C{\equiv}CH$.

5. The compound of claim 2, wherein
  $R^1$ is hydrogen, $CH_3$, $CH_2CH_3$, $CH(CH_2)_2$, or $CH_2CH(CH_2)_2$;
  $R^2$, $R^4$ are each independently Cl;
  $R^3$, $R^5$, and $R^6$ are each independently hydrogen; and
  $R^7$ is $(CH_2)_{11}OH$, $CH_2NH(CH_2)_8OH$, or $CH_2N(CH_3)CH_2{\equiv}CH$.

6. The compound of claim 2, wherein
  $R^1$ is hydrogen, $CH_3$, $CH_2CH_3$, $CH_2CH(CH_3)_2$, $CH_2CH(CH_2)_2$, $CH(CH_3)_2$, or benzyl;
  $R^2$, $R^3$, $R^4$, $R^6$, and $R^7$ are each independently hydrogen; and
  $R^5$ is $(CH_2)_{11}OH$ or $(CH_2)_{12}OH$.

7. The compound of claim 2, wherein
  $R^1$ is $CH_3$;
  $R^2$, $R^5$, and $R^6$ are each independently hydrogen;
  $R^3$ and $R^4$ are each independently $OCH_3$ or Cl; and
  $R^7$ is $(CH_2)_{11}OH$.

8. The compound of claim 2, which is selected from the group consisting of:

9-(8-(benzyloxy)quinolin-2-yl)nonan-1-ol,
10-(8-(benzyloxy)quinolin-2-yl)decan-1-ol,
11-(8-(benzyloxy)quinolin-2-yl)undecan-1-ol,
12-(8-(benzyloxy)quinolin-2-yl)dodecan-1-ol,
13-(8-(benzyloxy)quinolin-2-yl)tridecan-1-ol,
14-((8-(benzyloxy)quinolin-2-yl)tetradecan-1-ol,
15-(8-(benzyloxy)quinolin-2-yl)pentadecan-1-ol,
11-(8-(benzyloxy)-5-methylquinolin-2-yl)undecan-1-ol,
11-(8-(benzyloxy)-6-methylquinolin-2-yl)undecan-1-ol,
11-(8-(benzyloxy)-5-fluoroquinolin-2-yl)undecan-1-ol,
11-(8-(benzyloxy)-5-chloroquinolin-2-yl)undecan-1-ol,
2-(9-hydroxynonyl)quinolin-8-ol,
2-(10-hydroxydecyl)quinolin-8-ol,
2-(11-hydroxyundecyl)quinolin-8-ol,
2-(12-hydroxydodecyl)quinolin-8-ol,
2-(13-hydroxytridecyl)quinolin-8-ol,
2-(14-(hydroxytetradecyl)quinolin-8-ol,
2-(15-hydroxypentadecyl)quinolin-8-ol,
2-(11-hydroxyundecyl)-5-methylquinolin-8-ol,
2-(11-hydroxyundecyl)-6-methylquinolin-8-ol,
5-chloro-2-(11-hydroxyundecyl)quinolin-8-ol,
9-(8-methoxyquinolin-2-yl)nonan-1-ol,
10-(8-methoxyquinolin-2-yl)decan-1-ol,
11-(8-methoxyquinolin-2-yl)undecan-1-ol,
12-(8-methoxyquinolin-2-yl)dodecan-1-ol,
13-(8-methoxyquinolin-2-yl)tridecan-1-ol,
14-((8-methoxyquinolin-2-yl)tetradecan-1-ol,
15-(8-methoxyquinolin-2-yl)pentadecan-1-ol,
11-(8-methoxy-5-methylquinolin-2-yl)undecan-1-ol,
11-(5-fluoro-8-methoxyquinolin-2-yl)undecan-1-ol,
12-(5-fluoro-8-methoxyquinolin-2-yl)dodecan-1-ol,
9-(5-chloro-8-methoxyquinolin-2-yl)nonan-1-ol,
11-(5-chloro-8-methoxyquinolin-2-yl)undecan-1-ol,
15-(5-chloro-8-methoxyquinolin-2-yl)pentadecan-1-ol,
11-(5-bromo-8-methoxyquinolin-2-yl)undecan-1-ol,
11-(8-methoxy-5-(trifluoromethyl)quinolin-2-yl)undecan-1-ol,
11-(5,8-dimethoxyquinolin-2-yl)undecan-1-ol,
11-(8-methoxy-6-methylquinolin-2-yl)undecan-1-ol,
11-(6-fluoro-8-methoxyquinolin-2-yl)undecan-1-ol,
11-(6-chloro-8-methoxyquinolin-2-yl)undecan-1-ol,
11-(7-fluoro-8-methoxyquinolin-2-yl)undecan-1-ol,
11-(7-chloro-8-methoxyquinolin-2-yl)undecan-1-ol,
11-(5-chloro-6,8-dimethoxyquinolin-2-yl)undecan-1-ol,
11-(6-chloro-5,8-dimethoxyquinolin-2-yl)undecan-1-ol,
11-(5,7-dichloro-8-methoxyquinolin-2-yl)undecan-1-ol,
9-(8-ethoxyquinolin-2-yl)nonan-1-ol,
10-(8-ethoxyquinolin-2-yl)decan-1-ol,
11-(8-ethoxyquinolin-2-yl)undecan-1-ol,
12-(8-ethoxyquinolin-2-yl)dodecan-1-ol,
13-(8-ethoxyquinolin-2-yl)tridecan-1-ol,
14-((8-ethoxyquinolin-2-yl)tetradecan-1-ol,
15-(8-ethoxyquinolin-2-yl)pentadecan-1-ol,
11-(8-ethoxy-5-methylquinolin-2-yl)undecan-1-ol,
11-(8-ethoxy-5-fluoroquinolin-2-yl)undecan-1-ol,
9-(5-chloro-8-ethoxyquinolin-2-yl)nonan-1-ol,
11-(5-chloro-8-ethoxyquinolin-2-yl)undecan-1-ol,
15-(5-chloro-8-ethoxyquinolin-2-yl)pentadecan-1-ol,
11-(5-bromo-8-ethoxyquinolin-2-yl)undecan-1-ol;
11-(5,7-dichloro-8-ethoxyquinolin-2-yl)undecan-1-ol,
9-(8-isopropoxyquinolin-2-yl)nonan-1-ol,
10-(8-isopropoxyquinolin-2-yl)decan-1-ol,
11-(8-isopropoxyquinolin-2-yl)undecan-1-ol,
12-(8-isopropoxyquinolin-2-yl)dodecan-1-ol,
13-(8-isopropoxyquinolin-2-yl)tridecan-1-ol,
14-((8-isopropoxyquinolin-2-yl)tetradecan-1-ol,
15-(8-isopropoxyquinolin-2-yl)pentadecan-1-ol,
11-(8-isopropoxy-5-methylquinolin-2-yl)undecan-1-ol,
11-(5-fluoro-8-isopropoxyquinolin-2-yl)undecan-1-ol,
9-(5-chloro-8-isopropoxyquinolin-2-yl)nonan-1-ol,
11-(5-chloro-8-isopropoxyquinolin-2-yl)undecan-1-ol,
15-(5-chloro-8-isopropoxyquinolin-2-yl)pentadecan-1-ol,
11-(5-bromo-8-isopropoxyquinolin-2-yl)undecan-1-ol,
11-(5,7-dichloro-8-isopropoxyquinolin-2-yl)undecan-1-ol,
9-(8-(cyclopropylmethoxy)quinolin-2-yl)nonan-1-ol,
10-(8-(cyclopropylmethoxy)quinolin-2-yl)decan-1-ol,
11-(8-(cyclopropylmethoxy)quinolin-2-yl)undecan-1-ol,
12-(8-(cyclopropylmethoxy)quinolin-2-yl)dodecan-1-ol,
13-(8-(cyclopropylmethoxy)quinolin-2-yl)tridecan-1-ol,
14-((8-(cyclopropylmethoxy)quinolin-2-yl)tetradecan-1-ol,
15-(8-(cyclopropylmethoxy)quinolin-2-yl)pentadecan-1-ol,
11-(8-(cyclopropylmethoxy)-5-methylquinolin-2-yl)undecan-1-ol,
11-(8-(cyclopropylmethoxy)-5-fluoroquinolin-2-yl)undecan-1-ol,
9-(5-chloro-8-(cyclopropylmethoxy)quinolin-2-yl)nonan-1-ol,
11-(5-chloro-8-(cyclopropylmethoxy)quinolin-2-yl)undecan-1-ol,
15-(5-chloro-8-(cyclopropylmethoxy)quinolin-2-yl)pentadecan-1-ol,
11-(5-bromo-8-(cyclopropylmethoxy)quinolin-2-yl)undecan-1-ol,
11-(5,7-dichloro-8-(cyclopropylmethoxy)quinolin-2-yl)undecan-1-ol,
5,7-dichloro-2-(11-hydroxyundecyl)quinolin-8-ol,
10-(5-chloro-8-methoxyquinolin-2-yl)decan-1-ol,
acetic acid 10-(5-chloro-8-methoxyquinolin-2-yl)decyl ester,
11-(5-chloro-8-methoxyquinolin-2-yl)undecan-1-ol,
acetic acid 11-(5-chloro-8-methoxyquinolin-2-yl)undecyl ester,
12-(5-chloro-8-methoxyquinolin-2-yl)dodecan-1-ol,
acetic acid 12-(5-chloro-8-methoxyquinolin-2-yl)dodecyl ester,
13-(5-(chloro-8-methoxyquinolin-2-yl)tridecan-1-ol,
acetic acid 13-(5-chloro-8-methoxyquinolin-2-yl)tridecyl ester,
11-(8-methoxyquinolin-4-(-yl)undecan-1-ol,
11-(8-ethoxyquinolin-4-(-yl)undecan-1-ol,
11-(8-isopropoxyquinolin-4-(-yl)undecan-1-ol,
11-(8-(cyclopropylmethoxy)quinolin-4-(-yl)undecan-1-ol,
11-(8-benzyloxy)quinolin-4-(-yl)undecan-1-ol,
12-(8-benzyloxy)quinolin-4-(-yl)dodecan-1-ol,
4-((11-hydroxyundecyl)quinolin-8-ol,
4-((12-hydroxydodecyl)quinolin-8-ol,
9-(8-trifluoromethoxy)quinolin-2-yl)nona-1-ol,
11-(8-(trifluoromethoxy)quinolin-2-yl)undecan-1-ol,
14-((8-(trifluoromethoxy)quinolin-2-yl)tetradecan-1-ol,
15-(8-(trifluoromethoxy)quinolin-2-yl)pentadecan-1-ol,
2-((4-((2-hydroxyethyl)piperazin-1-yl)methyl)quinolin-8-ol,
2-(4-(((5-chloro-8-methoxyquinolin-2-yl)methyl)piperazin-1-yl)ethanol,
2-(4-(((5-chloro-8-ethoxyquinolin-2-yl)methyl)piperazin-1-yl)ethanol, 2-(4-(((5-chloro-8-isopropoxyquinolin-2-yl)methyl)piperazin-1-yl)ethanol,
2-(4-(((5-chloro-8-(cyclopropylmethoxy)quinolin-2-yl)methyl)piperazin-1-yl)ethane,
2-(4-(((5,7-dichloro-8-methoxyquinolin-2-yl)methyl)piperazin-1-yl)ethanol,
2-(4-(((5,7-dichloro-8-(cyclopropylmethoxy)quinolin-2-yl)methyl)piperazin-1-yl)ethanol,
2-((methyl(prop-2-ynyl)amino)methyl)quinolin-8-ol,
5-chloro-2-((methyl(prop-2-ynyl)amino)methyl)quinolin-8-ol,
N((5-chloro-8-methoxyquinolin-2-yl)methyl)-N-methylprop-2-yn-1-amine,
N((5-chloro-8-ethoxyquinolin-2-yl)methyl)-N-methylprop-2-yn-1-amine,
N((5-chloro-8-isopropoxyquinolin-2-yl)methyl)-N-methylprop-2-yn-1-amine,
N((5-chloro-8-(cyclopropylmethoxy)quinolin-2-yl)methyl)-N-methylprop-2-yn-1-amine,
N((5,7-dichloro-8-methoxyquinolin-2-yl)methyl)-N-methylprop-2-yn-1-amine,
N((5,7-dichloro-8-(cyclopropylmethoxy)quinolin-2-yl)methyl)-N-methylprop-2-yn-1-amine,
8-((5-chloro-8-methoxyquinolin-2-yl)methylamino)octan-1-ol,
8-((5-chloro-8-ethoxyquinolin-2-yl)methylamino)octan-1-ol,
8-((5-chloro-8-isopropoxyquinolin-2-yl)methylamino)octan-1-ol,
8-((5-chloro-8-(cyclopropylmethoxy)quinolin-2-yl)methylamino)octan-1-ol,
8-((5,7-dichloro-8-methoxyquinolin-2-yl)methylamino)octan-1-ol,
8-((5,7-dichloro-8-(cyclopropylmethoxy)quinolin-2-yl)methylamino)octan-1-ol, and
6-(bis((8-methoxyquinolin-2-yl)methyl)amino)hexan-1-ol.

9. A composition comprising a therapeutically effective amount of the compound of claim 1, or a pharmaceutically acceptable salt thereof, and a pharmaceutically acceptable vehicle or carrier.

10. A method for improving learning and/or memory in Alzheimer's disease, or treating brain traumatic injury, and/or spinal cord injury, comprising administering to a subject in need thereof a therapeutically effective amount of the compound of claim 1 or a pharmaceutically acceptable salt thereof, and a pharmaceutically acceptable vehicle or carrier.

11. A method of improving learning and/or memory in Alzheimer's disease, or treating brain traumatic injury, and/or spinal cord injury, comprising administering to a subject in need thereof a therapeutically elective amount of the compound of claim 8 or a pharmaceutically acceptable salt thereof, and a pharmaceutically acceptable vehicle or carrier.

12. A method for improving learning and/or memory performance in a patient of Alzheimer's disease, comprising administering to the patient of Alzheimer's disease a therapeutically effective amount of the compound of claim 1 or a pharmaceutically acceptable salt thereof, and a pharmaceutically acceptable vehicle or carrier.

13. A method of improving learning and/or memory performance in a patient of Alzheimer's disease, comprising administering to the patient of Alzheimer's disease a therapeutically effective amount of the compound of claim 8 or a pharmaceutically acceptable salt thereof, and a pharmaceutically acceptable vehicle or carrier.

14. A compound of Formula (I) or a pharmaceutically acceptable salt thereof:

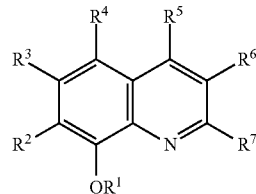

Formula (I)

(I) wherein
$R^1$ is hydrogen, $(C_1-C_8)$alkyl, $(C_1-C_8)$alkylene$(C_3-C_8)$cycloalkyl, $(C_1-C_8)$haloalkyl, or $(C_1-C_8)$alkylene$(C_6-C_{20})$aryl;
$R^2$ is hydrogen;
$R^3$ is hydrogen, halogen, $(C_1-C_8)$alkyl, or $(C_1-C_8)$alkoxy;
$R^4$ is hydrogen, halogen, $(C_1-C_8)$alkyl, $(C_1-C_8)$alkoxy, or $(C_1-C_8)$haloalkyl;
$R^5$ is hydrogen or $(C_1-C_{20})$alkanol;
$R^6$ is hydrogen; and
$R^7$ is $(C_5-C_{20})$alkanol, $(C_1-C_8)$alkylene $(C_3-C_8)$heterocyclyl$(C_1-C_{20})$alkanol, $(C_1-C_8)$alkylene $(C_3-C_8)$heterocyclyl$(C_1-C_{20})$alkyl, $(C_{10}-C_{13})$alkyleneOCOCH$_3$, $(C_1-C_8)$alkylene$(C_1-C_6)$alkylamino$(C_1-C_6)$alkynyl, $(C_1-C_8)$alkyleneamino$(C_1-C_{20})$alkanol, or $(C_1-C_8)$alkyleneamino$(C_1-C_{20})$alkanol$(C_1-C_8)$alkylene substituted $(C_3-C_{20})$heteroaryl;

or (II) wherein:
$R^1$, $R^2$, $R^3$, $R^4$ and $R^6$ are each defined in (I) above;
$R^5$ is $(C_1-C_{20})$alkanol;
$R^7$ is hydrogen, $(C_5-C_{20})$alkanol, (C5-$C_8$)alkylene $(C_3-C_8)$heterocyclyl$(C_1-C_{20})$alkanol, $(C_1-C_8)$alkylene $(C_3-C_8)$heterocyclyl$(C_1-C_{20})$alkyl, $(C_{10}-C_{13})$alkyleneOCOCH$_3$, $(C_1-C_8)$alkylene$(C_1-C_6)$alkylamino$(C_1-C_6)$alkynyl, $(C_1-C_8)$alkyleneamino$(C_1-C_{20})$alkanol, or $(C_1-C_8)$alkyleneamino$(C_1-C_{20})$alkanol$(C_1-C_8)$alkylene substituted $(C_3-C_{20})$heteroaryl.

15. A compound of Formula (I) or a pharmaceutically acceptable salt thereof:

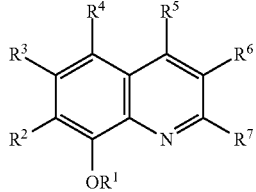

Formula (I)

(I) wherein
$R^1$ is hydrogen, $(C_1-C_8)$alkyl, $(C_1-C_8)$alkylene$(C_3-C_8)$cycloalkyl, $(C_1-C_8)$haloalkyl;
$R^2$ is hydrogen or halogen;
$R^3$ is hydrogen, halogen, $(C_1-C_8)$alkyl, or $(C_1-C_8)$alkoxy;
$R^4$ is hydrogen, halogen, $(C_1-C_8)$alkyl, $(C_1-C_8)$alkoxy, or $(C_1-C_8)$haloalkyl;
$R^5$ is hydrogen or $(C_1-C_{20})$alkanol;
$R^6$ is hydrogen; and
$R^7$ is $(C_5-C_{20})$alkanol, $(C_1-C_8)$alkylene $(C_3-C_8)$heterocyclyl$(C_1-C_{20})$alkanol, $(C_1-C_8)$alkylene $(C_3-C_8)$heterocyclyl$(C_1-C_{20})$alkyl, $(C_{10}-C_{13})$alkyleneOCOCH$_3$, $(C_1-C_8)$alkylene$(C_1-C_6)$alkylamino$(C_1-C_6)$alkynyl, $(C_1-C_8)$ alkyleneamino($C_1$-$C_{20}$)alkanol, or ($C_1$-$C_8$)alkyleneamino($C_1$-$C_{20}$)alkanol($C_1$-$C_8$)alkylene substituted ($C_3$-$C_{20}$)heteroaryl;

or (II) wherein:

$R^1$, $R^2$, $R^3$, $R^4$ and $R^6$ are each defined in (I) above;

$R^5$ is ($C_1$-$C_{20}$)alkanol;

$R^7$ is hydrogen, ($C_5$-$C_{20}$)alkanol, ($C_1$-$C_8$)alkylene ($C_3$-$C_8$)heterocyclyl($C_1$-$C_{20}$)alkanol, ($C_1$-$C_8$)alkylene ($C_3$-$C_8$)heterocyclyl($C_1$-$C_{20}$)alkyl, ($C_{10}$-$C_{13}$)alkyleneO-COCH$_3$, ($C_1$-$C_8$)alkylene($C_1$-$C_6$)alkylamino($C_1$-$C_6$)alkynyl, ($C_1$-$C_8$)alkyleneamino($C_1$-$C_{20}$)alkanol, or ($C_1$-$C_8$)alkyleneamino($C_1$-$C_{20}$)alkanol($C_1$-$C_8$)alkylene substituted ($C_3$-$C_{20}$)heteroaryl.

16. A method for improving learning and/or memory in Alzheimer's disease, or treating, brain traumatic injury, and/or spinal cord injury, comprising administering to a subject in need thereof a therapeutically effective amount of the compound of claim 14 or a pharmaceutically acceptable salt thereof, and a pharmaceutically acceptable vehicle or carrier.

17. A method of improving learning and/or memory performance in a patient of Alzheimer's disease, comprising administering to the patient of Alzheimer's disease a therapeutically effective amount of the compound of claim 14 or a pharmaceutically acceptable salt thereof, and a pharmaceutically acceptable vehicle or carrier.

18. A method for improving learning and/or memory performance in a patient of Alzheimer's disease, or treating brain traumatic injury, and/or spinal cord injury, comprising administering to a subject in need thereof a therapeutically effective amount of the compound of claim 15 or a pharmaceutically acceptable salt thereof, and a pharmaceutically acceptable vehicle or carrier.

19. A method of improving learning and/or memory performance in a patient of Alzheimer's disease, comprising, administering to the patient of Alzheimer's disease a therapeutically effective amount of the compound of claim 15 or a pharmaceutically acceptable salt thereof, and a pharmaceutically acceptable vehicle or carrier.

* * * * *